(12) United States Patent
Addington et al.

(10) Patent No.: US 9,452,270 B2
(45) Date of Patent: Sep. 27, 2016

(54) NEBULIZER HAVING REPLACEABLE NOZZLE ASSEMBLY AND SUCTION LINE

(71) Applicant: PNEUMOFLEX SYSTEMS, LLC, Melbourne, FL (US)

(72) Inventors: W. Robert Addington, Melbourne Beach, FL (US); Stuart P. Miller, Indialantic, FL (US); Robert E. Stephens, Parkville, MO (US)

(73) Assignee: Pneumoflex Systems, LLC, Melbourne, FL (US)

(*) Notice: Subject to any disclaimer, the term of this patent is extended or adjusted under 35 U.S.C. 154(b) by 0 days.

(21) Appl. No.: 14/195,933

(22) Filed: Mar. 4, 2014

(65) Prior Publication Data

US 2014/0174435 A1    Jun. 26, 2014

Related U.S. Application Data

(63) Continuation-in-part of application No. 13/799,196, filed on Mar. 13, 2013, now abandoned, which is a continuation-in-part of application No. 13/353,611, filed on Jan. 19, 2012, now Pat. No. 8,671,934.

(60) Provisional application No. 61/434,613, filed on Jan. 20, 2011.

(51) Int. Cl.
*A61M 11/00* (2006.01)
*A61M 11/02* (2006.01)
(Continued)

(52) U.S. Cl.
CPC ............. *A61M 11/06* (2013.01); *A61B 5/0823* (2013.01); *A61B 5/4839* (2013.01);
(Continued)

(58) Field of Classification Search
CPC .... A61M 11/00; A61M 11/02; A61M 11/08; A61M 11/06; A61M 15/0086; A61M 16/14; A61M 2205/8225; A61M 2206/14; A61M 15/009; A61M 16/147; A61J 17/006

USPC ............. 128/200.21; 239/338, 370; 261/78.1
See application file for complete search history.

(56) References Cited

U.S. PATENT DOCUMENTS 341,712 A    5/1886 Wilson
2,245,872 A *    6/1941 Pitts ........................ 128/200.18
(Continued)

FOREIGN PATENT DOCUMENTS

EP    0667168    2/1994
WO    2011006184    1/2011

OTHER PUBLICATIONS

Joseph L. Rau, 2004 Philip Kittredge Memorial Lecture, The Inhalation of Drugs: Advantages and Problems, Respiratory Care, Mar. 2005, vol. 50, No. 3, pp. 367-382. ***See Priority U.S. Appl. No. 13/353,611; filed Jan. 19, 2012.
(Continued)

*Primary Examiner* — Peter S Vasat
(74) *Attorney, Agent, or Firm* — Allen, Dyer, Doppelt, Milbrath & Gilchrist, P.A.

(57) ABSTRACT

A medication reservoir is formed in the lower portion of a nebulizer body and covered to form an enclosed medication reservoir. A nozzle assembly is supported by a reservoir cover and includes an air line having an inlet at one end and an outlet and a venturi nozzle and venturi outlet. The air line, venturi nozzle and discharge outlet are horizontally oriented when in use and the venturi nozzle is located within a patient's oral cavity when the nebulizer is in use. Medication is drawn upward through a suction line and mixed with air passing through the venturi nozzle and nebulized for discharge through the nebulizer outlet. The venturi nozzle and suction line are formed together and replaceable as one unit.

14 Claims, 37 Drawing Sheets

Figure 1:
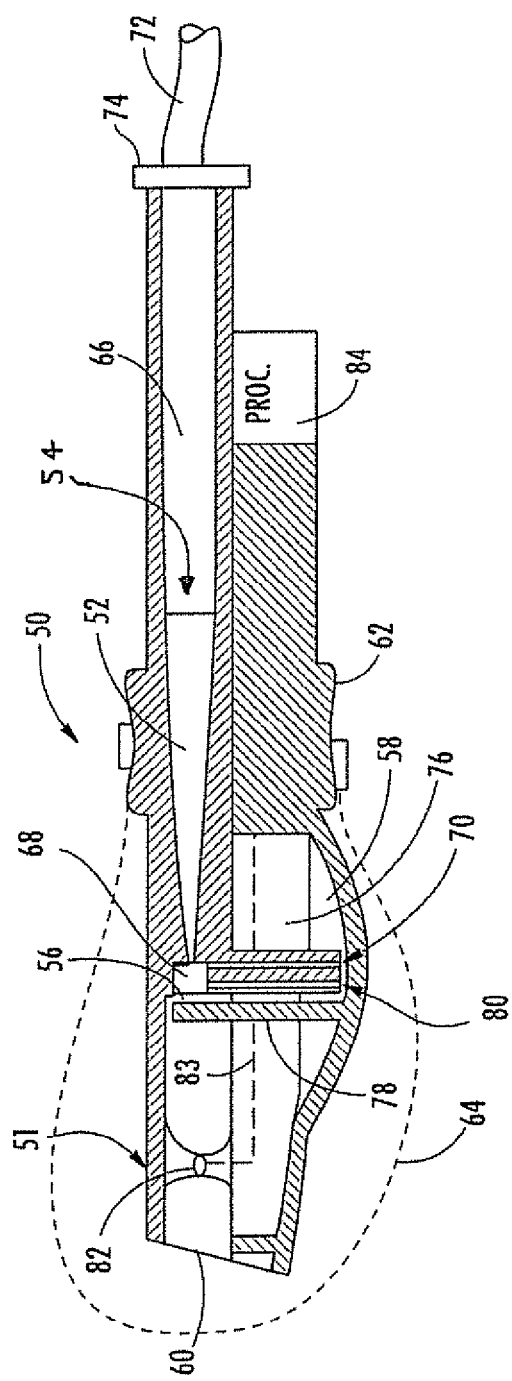

(51) Int. Cl.

| | |
|---|---|
| *A61M 11/06* | (2006.01) |
| *A61B 5/08* | (2006.01) |
| *A61B 5/00* | (2006.01) |
| *A61M 16/00* | (2006.01) |
| *A61M 16/14* | (2006.01) |
| *A61M 15/00* | (2006.01) |

(52) U.S. Cl.
CPC ....... *A61B 5/7282* (2013.01); *A61M 15/0036* (2014.02); *A61M 15/0086* (2013.01); *A61M 15/0091* (2013.01); *A61M 16/0051* (2013.01); *A61M 16/14* (2013.01); *A61J 17/006* (2015.05); *A61M 2016/0027* (2013.01); *A61M 2016/0039* (2013.01); *A61M 2205/13* (2013.01); *A61M 2205/3569* (2013.01); *A61M 2205/3592* (2013.01); *A61M 2205/502* (2013.01); *A61M 2205/8225* (2013.01); *A61M 2206/14* (2013.01)

(56) References Cited

U.S. PATENT DOCUMENTS

| | | |
|---|---|---|
| 2,280,050 A | 4/1942 | Alexander et al. |
| 3,097,645 A | 7/1963 | Lester |
| 3,664,337 A * | 5/1972 | Lindsey et al. .......... 128/200.18 |
| 3,888,253 A | 6/1975 | Watt et al. |
| 3,998,226 A | 12/1976 | Harris |
| 4,253,468 A | 3/1981 | Lehmbeck |
| 4,318,397 A | 3/1982 | Kobayashi |
| 4,333,450 A | 6/1982 | Lester |
| 4,792,097 A | 12/1988 | Kremer, Jr. et al. |
| 4,809,706 A | 3/1989 | Watson et al. |
| 4,852,582 A | 8/1989 | Pell |
| 4,884,460 A | 12/1989 | Nowacki et al. |
| 4,951,661 A | 8/1990 | Sladek |
| RE33,717 E | 10/1991 | Svoboda |
| 5,186,166 A | 2/1993 | Riggs et al. |
| 5,301,666 A | 4/1994 | Lerk et al. |
| 5,312,046 A | 5/1994 | Knoch et al. |
| 5,411,208 A | 5/1995 | Burgener |
| 5,598,838 A | 2/1997 | Servidio et al. |
| 5,649,530 A | 7/1997 | Ballini |
| 5,666,946 A | 9/1997 | Langenback |
| 5,676,132 A | 10/1997 | Tillotson et al. |
| 5,678,563 A | 10/1997 | Addington et al. |
| 5,685,291 A | 11/1997 | Marsh |
| 5,823,187 A | 10/1998 | Estes et al. |
| 5,839,430 A | 11/1998 | Cama |
| 5,904,140 A | 5/1999 | McGoogan |
| 6,004,268 A | 12/1999 | Addington et al. |
| 6,029,660 A | 2/2000 | Calluaud et al. |
| 6,044,841 A | 4/2000 | Verdun et al. |
| 6,050,953 A | 4/2000 | Warwick et al. |
| 6,085,741 A | 7/2000 | Becker |
| 6,183,423 B1 | 2/2001 | Gaumond et al. |
| 6,223,745 B1 | 5/2001 | Hammarlund et al. |
| 6,267,006 B1 | 7/2001 | Bugli et al. |
| 6,328,030 B1 | 12/2001 | Kidwell et al. |
| 6,398,728 B1 | 6/2002 | Bardy |
| 6,411,843 B1 | 6/2002 | Zarychta |
| 6,568,387 B2 | 5/2003 | Davenport et al. |
| 6,598,602 B1 | 7/2003 | Sjoholm |
| 6,615,826 B1 | 9/2003 | Gabrio et al. |
| 6,655,376 B2 | 12/2003 | Addington et al. |
| 6,679,250 B2 | 1/2004 | Walker et al. |
| 6,698,422 B2 | 3/2004 | Fugelsang et al. |
| 6,729,327 B2 | 5/2004 | McFarland |
| 6,735,471 B2 | 5/2004 | Hill et al. |
| 6,848,443 B2 | 2/2005 | Schmidt et al. |
| 7,013,894 B2 | 3/2006 | McFarland |
| 7,080,643 B2 | 7/2006 | Grychowski et al. |
| 7,191,780 B2 | 3/2007 | Faram |
| 7,264,179 B2 | 9/2007 | Robbins |
| 7,270,123 B2 | 9/2007 | Grychowski et al. |
| 7,290,541 B2 | 11/2007 | Irvi et al. |
| 7,322,349 B2 | 1/2008 | Power |
| 7,568,480 B2 | 8/2009 | Foley et al. |
| 7,614,280 B1 | 11/2009 | Gardner et al. |
| 7,634,995 B2 | 12/2009 | Grychowski et al. |
| 7,712,466 B2 | 5/2010 | Addington et al. |
| 7,721,729 B2 | 5/2010 | Von Hollen et al. |
| 7,726,306 B2 | 6/2010 | Addington et al. |
| 7,841,335 B2 | 11/2010 | Harrington et al. |
| 7,841,336 B2 | 11/2010 | Rivera et al. |
| 7,870,857 B2 | 1/2011 | Dhuper et al. |
| 7,971,588 B2 | 7/2011 | Fink et al. |
| 8,109,266 B2 | 2/2012 | Addington et al. |
| 8,245,708 B2 | 8/2012 | Smaldone et al. |
| 8,371,299 B2 | 2/2013 | Denyer et al. |
| 8,408,200 B2 | 4/2013 | Clark et al. |
| 8,597,184 B2 | 12/2013 | Addington et al. |
| 8,671,934 B2 | 3/2014 | Addington et al. |
| 2001/0037807 A1* | 11/2001 | Kong ...................... 128/200.21 |
| 2001/0050086 A1 | 12/2001 | Addington et al. |
| 2002/0121275 A1 | 9/2002 | Johnson et al. |
| 2003/0079742 A1 | 5/2003 | Giroux |
| 2003/0121517 A1 | 7/2003 | McFarland |
| 2003/0136399 A1 | 7/2003 | Foley et al. |
| 2003/0205229 A1 | 11/2003 | Crockford et al. |
| 2004/0172010 A1 | 9/2004 | Addington et al. |
| 2004/0181161 A1 | 9/2004 | Addington et al. |
| 2004/0187864 A1 | 9/2004 | Adams |
| 2004/0206351 A1 | 10/2004 | McFarland, Jr. |
| 2005/0028816 A1* | 2/2005 | Fishman et al. ......... 128/200.24 |
| 2005/0081844 A1 | 4/2005 | Grychowski et al. |
| 2007/0135736 A1 | 6/2007 | Addington et al. |
| 2007/0137648 A1 | 6/2007 | Addington et al. |
| 2007/0163572 A1 | 7/2007 | Addington et al. |
| 2007/0255090 A1 | 11/2007 | Addington et al. |
| 2008/0004540 A1 | 1/2008 | Nakao et al. |
| 2008/0283049 A1* | 11/2008 | Mahoney et al. ....... 128/200.14 |
| 2009/0025718 A1 | 1/2009 | Denyer et al. |
| 2009/0050141 A1 | 2/2009 | King et al. |
| 2009/0062855 A1 | 3/2009 | Lemery et al. |
| 2010/0137736 A1 | 6/2010 | Addington et al. |
| 2010/0137737 A1 | 6/2010 | Addington et al. |
| 2010/0147298 A1 | 6/2010 | Loescher et al. |
| 2010/0204602 A1* | 8/2010 | Addington et al. .......... 600/538 |
| 2011/0040157 A1 | 2/2011 | Addington et al. |
| 2011/0040211 A1 | 2/2011 | Addington et al. |
| 2011/0046653 A1 | 2/2011 | Addington et al. |
| 2012/0053482 A1 | 3/2012 | Addington et al. |
| 2012/0145153 A1 | 6/2012 | Bassin et al. |
| 2012/0186582 A1 | 7/2012 | Addington et al. |
| 2012/0190999 A1 | 7/2012 | Addington et al. |
| 2013/0081617 A1 | 4/2013 | Cavendish |
| 2013/0192594 A1 | 8/2013 | Addington et al. |

OTHER PUBLICATIONS

Cates et al., "Holding Chambers Versus Nebulisers for Inhaled Steroids in Chronic Asthma (Review)," The Cochrane Collaboration, The Cochrane Database of Systematic Reviews 2006, Issue 1, Art No. CD001491, pub 2, 23 pages. ***See Priority U.S. Appl. No. 13/353,611; filed Jan. 19, 2012.

Lasserson et al. "Differences in Motor Activation of Voluntary and Reflex Cough in Humans" PubMed: Thorax. Aug. 2006; 61(8): 699-705. ***See Priority U.S. Appl. No. 13/353,611; filed Jan. 19, 2012.

"Battle of the MDI an DPI Patent Trends" Sep. 27, 2009; pp. 1-7: http://www.inhalationreport.com/2009/09/27/battle-of-the-mdi-and-dpi-patent-trends ***See Priority U.S. Appl. No. 13/353,611; filed Jan. 19, 2012.

"Inhaler 2.0—What's the Future of Inhalation Devices?" Jan. 25, 2010; 2 pgs. http://www/inhalationreport.com/2010/01/25/inhaler-2-0-whats-the-future-of-inhalation-devices/ ***See Priority U.S. Appl. No. 13/353,611; filed Jan. 19, 2012.

Adi et al. "Co-deposition of a triple therapy drug formulation for the treatment of chronic obstructive pulmonary disease using solution-based pressurised metered dose inhalers" J. Pharm Pharmacol. Sep. 2012; 64(9) 1245-53. (Abstract Only). ***See Priority U.S. Appl. No. 13/353,611; filed Jan. 19, 2012.

(56) References Cited

OTHER PUBLICATIONS

Coleman et al. "Therapeutic aerosol delivery during mechanical ventilation" http://www.ncbi.nlm.nih.gov/pubmed/8792952?report=abstract: Printed Jul. 2, 2013: (Abstract Only). ***See Priority U.S. Appl. No. 13/353,611; filed Jan. 19, 2012.

Berlinski et al. "Albuteral delivery by 4 different nebulizers placed in 4 different positions in a pediatric ventilator in vitro model" Respiratory Care: Jul. 2013; vol. 58, No. 7. pp. 1124-1133. ***See Priority U.S. Appl. No. 13/353,611; filed Jan. 19, 2012.

Ari et al. "Evaluation of aerosol generator devices at 3 locations in humidified and non-humidified circuits during adult mechanical ventilation" Respiratory Care: Jul. 2010; vol. 55, No. 7. pp. 837-844. ***See Priority U.S. Appl. No. 13/353,611; filed Jan. 19, 2012.

Leung et al. "Comparison of breath-enhanced to breath-actuated nebulizers for rate, consistency, and efficiently*" http://jounal.publications.chestnet.org/article.aspl?articleid=1082940: printed Jul. 3, 2010; pp. 1-10. ***See Priority U.S. Appl. No. 13/353,611; filed Jan. 19, 2012.

Barlow et al. "Frequency Modulation and Spatiotemporal Stability of the sCPC in Preterm Infants with RDS" Hindawi Publishing Corp. International Journal of Pediatrics: vol. 2012, Article ID 581538; 9 pgs. May 29, 2012.

Doherty et al. "Nebuliser Therapy in the Intensive Care Unit" Thorax 1997;52(Suppl2) pp. S56-S59.

Sakalidis et al. "Oxygen saturation and suck-swallow-breathe coordination of term infants during breastfeeding and feeding from a teat releasing mil only with vacuum" International Journal of Pediatrics; vol. 2012, article ID 130769, 10 pgs. accepted date Apr. 25, 2012.

Tomori et al. "Reversal of functional disorders by aspiration, expiration, and cough reflexes and their voluntary counterparts" www.frontiersin.org; Dec. 2012; vol. 3, article 467, 14 pgs.

Uldry et al. "Maximal values of sniff nasal inspiratory pressure in healthy subjects" thorax.bmj.com 1995;50: pp. 371-375 printed Apr. 16, 2014.

Amirav et al. "Lung aerosol deposition in suckling infants" Arch Dis Child 2012;97: pp. 497-501; printed May 19, 2012.

Patel et al. "Recovery from poststroke urinary incontinence: associated factors and impact on outcome" J Am Geriatr Soc. Sep. 2001;49(9) Abstract only.

Bean et al. "Influence of poststroke urinary incontinence on disability: the nursing home setting" Am J Phys Med Rehabil. Mar. 2003; 82(3) Abstract only.

Heritier et al. "Sniff nasal inspiratory pressure. A noninvasive assessment of inspiratory muscle strength" www.atsjournals.org/doi/abs/10.1164/ajrccm.150.6.7952632?journalcode=ajrcem; printed Oct. 1, 2013 Abstract only.

* cited by examiner

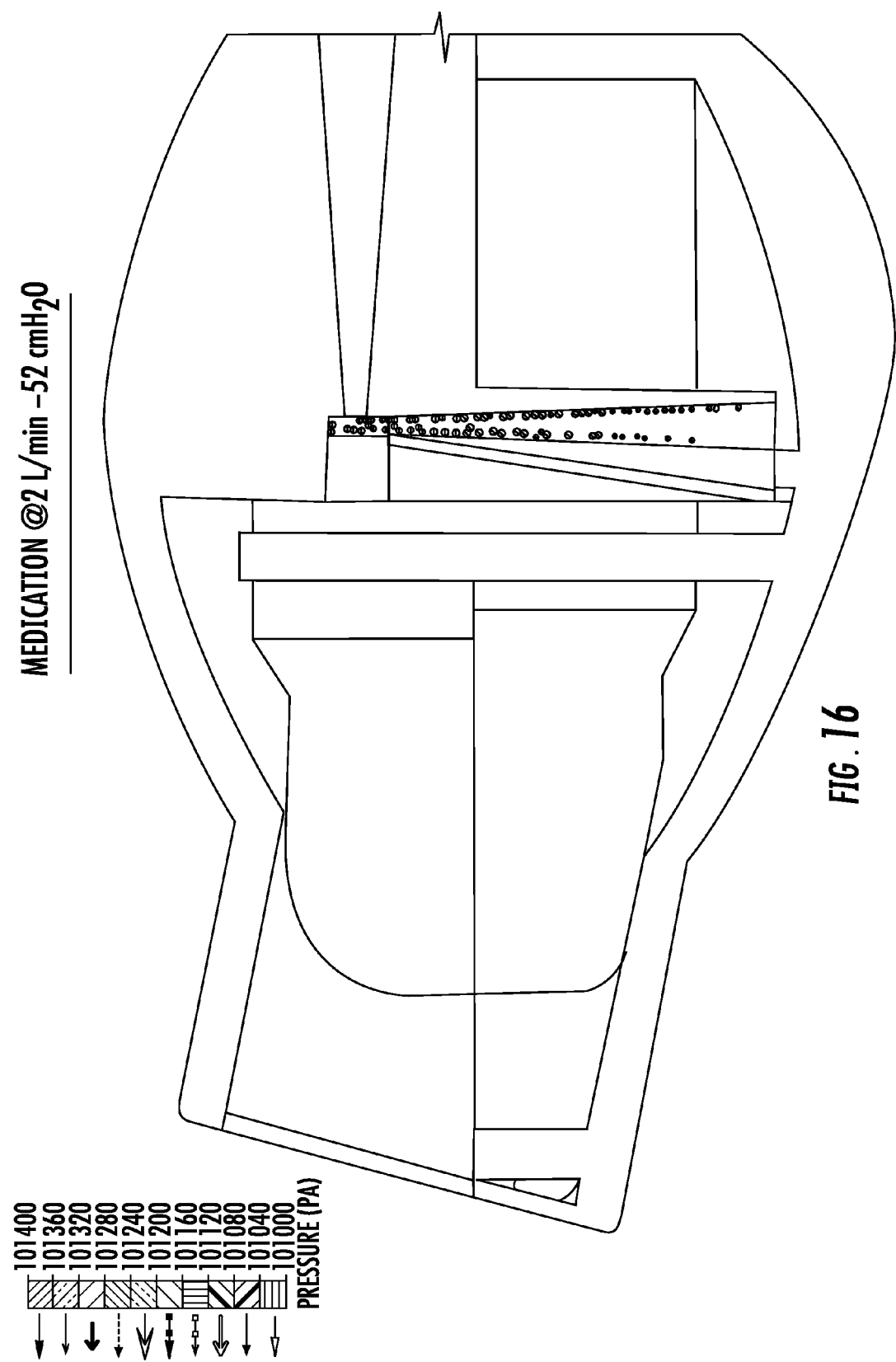

RESPIRATORY PRESSURES

TABLE 2– MEASURED AND PREDICTED MIP AND MEP FOR MALES AND FEMALES

| AGE BRACKET YEARS | MIP, cmH$_2$O | | MEP, cmH$_2$O | |
|---|---|---|---|---|
| | MEASURED | PREDICTED | MEASURED | PREDICTED |
| MEN | | | | |
| 20-29 | -113.5 ± 18.11 | -136.72 ± 2.53 * | 148 ± 29.46 | 146.43 ± 2.65 |
| 30-39 | -120 ± 16.16 | -129.14 ± 1.81 * | 135.5 ± 31.92 | 138.81 ± 1.83 |
| 40-49 | -100.42 ± 16.44 | -119.97 ± 2.38 * | 127.08 ± 19.59 | 129.53 ± 2.41 |
| 50-59 | -86 ± 26.23 | -114.46 ± 10.85 * | 112.5 ± 27.21 | 120.91 ± 2.75 |
| 60-69 | -85.00 ± 22.61 | -104.34 ± 2.10 * | 104.00 ± 22.09 | 113.70 ± 2.13 |
| 70-80 | -53 ± 19.18 | -93.7 ± 2.23 * | 74.5 ± 22.79 | 102.93 ± 2.26 |
| WOMEN | | | | |
| 20-29 | -80.50 ± 20.06 | -99.42 ± 1.25 * | 100.00 ± 18.41 | 101.94 ± 1.55 |
| 30-39 | -82.5 ± 22.88 | -93.64 ± 1.69 * | 94 ± 17.61 | 95.29 ± 1.77 |
| 40-49 | -78.6 ± 20.94 | -88.50 ± 1.44 * | 105.5 ± 25.54 | 88.27 ± 1.70 |
| 50-59 | -69 ± 19.41 | -83.84 ± 1.61 * | 88.5 ± 21.35 | 82.54 ± 2.01 |
| 60-69 | -63.5 ± 13.55 | -78.70 ± 1.88 * | 71 ± 9.07 | 76.13 ± 2.34 |
| 70-80 | -52 ± 11.83 | -73.31 ± 1.55 * | 66.5 ± 14.15 | 69.42 ± 1.93 |

* VALUES EXPRESSED AS MEAN ± SD; EACH AGE BRACKET COMPRISED 10 SUBJECTS. *P ≤ 0.05 VS MEASURED VALUES FROM THE CORRESPONDING AGE BRACKET (SHAPIRO-WILK TEST; STUDENT T-TEST;WILCOXON TEST).

FIG. 17

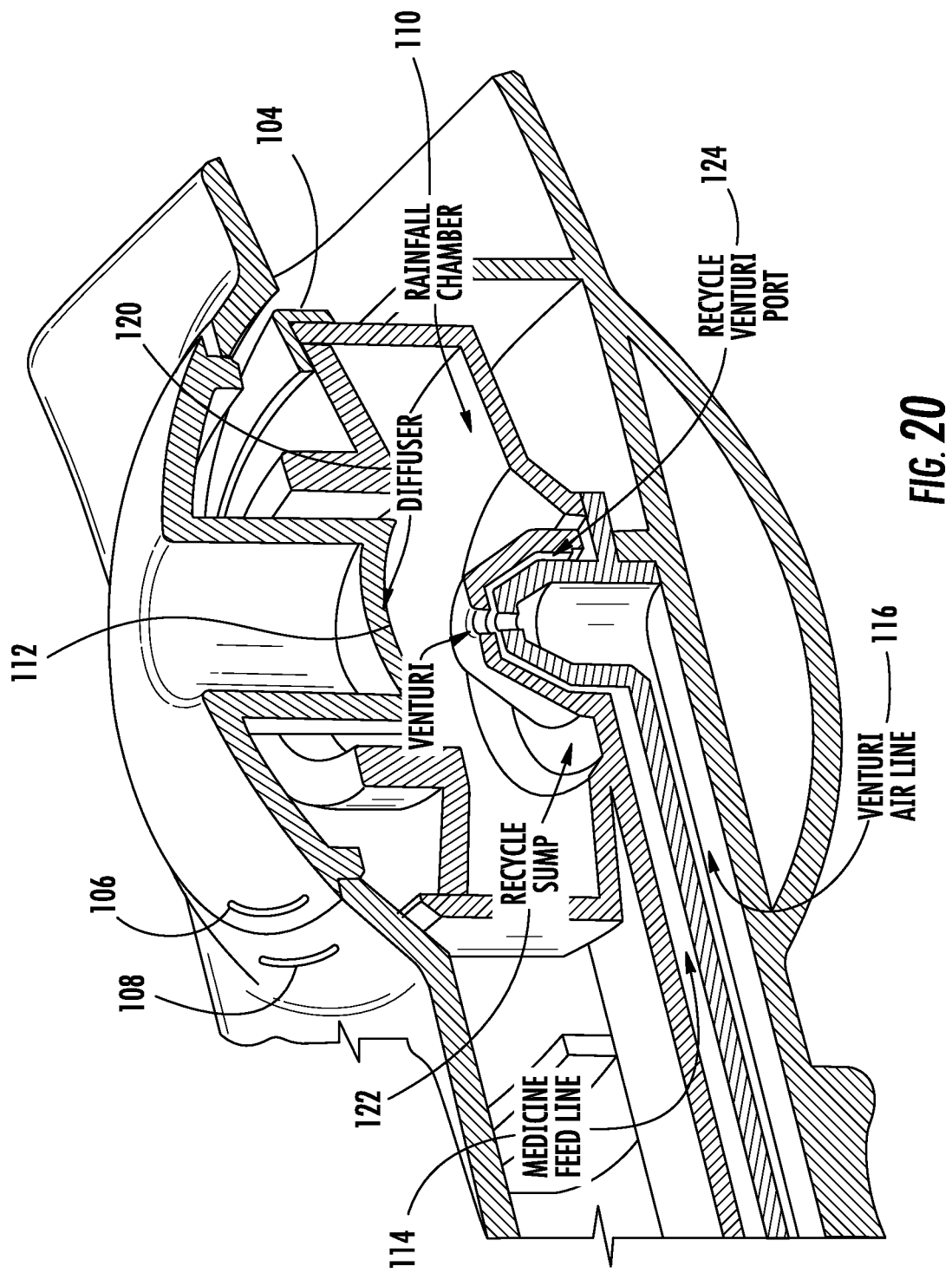

NEBULIZER HAVING REPLACEABLE NOZZLE ASSEMBLY AND SUCTION LINE

PRIORITY APPLICATION(S)

This is a continuation-in-part application of Ser. No. 13/799,196 filed Mar. 13, 2013, which is a continuation-in-part application of Ser. No. 13/353,611 filed Jan. 19, 2012, which claims priority to U.S. provisional application Ser. No. 61/434,613, filed Jan. 20, 2011; the disclosures which are hereby incorporated herein by reference in their entirety.

FIELD OF THE INVENTION

The present invention relates to the field of nebulizers, and more particularly, this invention relates to nebulizers having a venturi. The present invention also relates to the field of nebulizers configured for pediatric use and nebulizers having a flow meter function.

BACKGROUND OF THE INVENTION

Inhalation is a very old method of drug delivery. In the twentieth century it became a mainstay of respiratory care and was known as aerosol therapy. Use of inhaled epinephrine for relief of asthma was reported as early as 1929, in England. Dry powder inhalers have been used to administer penicillin dust to treat respiratory infections. In 1956, the first metered dosed inhaler was approved for clinical use.

The scientific basis for aerosol therapy developed relatively late, following the 1974 Sugar Loaf conference on the scientific basis of respiratory therapy. A more complete history of the development of aerosol therapy and the modern nebulizer is described in the 2004 Phillip Kitridge Memorial Lecture entitled, "The Inhalation of Drugs: Advantages and Problems by Joseph L. Row; printed in the March 2005 issue of Respiratory Care, vol. 50, no. 3.

Table 8 of the Respiratory Care article, referred to above, page 381, lists the characteristics of an ideal aerosol inhaler as follows:

TABLE 8

Dose reliability and reproducibility
High lung-deposition efficiency (target lung deposition of 100% of nominal dose)
Production of the fine particles ≤5 μm diameter, with correspondingly low mass median diameter
Simple to use and handle
Short treatment time
Small size and easy to carry
Multiple-dose capability
Resistance to bacterial contamination
Durable
Cost-effective
No drug released to ambient-air
Efficient (small particle size, high lung deposition) for the specific drug being aerosolized
Liked by patients and health care personnel Standard nebulizers typically fail to achieve a number of these characteristics because they waste medication during exhalation. Further, the particle size is often too large to reach the bottom of the lungs where the medication may be most needed. There is difficulty in estimating the dose of the drug being given to a patient and there is difficulty in reproducing that dose. There is a possibility of contamination when opening the initially sterile kit, pouring medication into the cup, and assembling the pieces for use by a patient. There is also considerable inefficiency in the medication delivery, with much of it being deposited in the throat, rather than in the lungs.

Commonly assigned U.S. patent application Ser. No. 12/724,785 filed Mar. 16, 2010, and published as 2010/0204602, the disclosure which is hereby incorporated by reference in its entirety, discloses a nebulizer having a flow meter function that is applied to venturi type intra-oral nebulizers as disclosed in commonly assigned U.S. Pat. Nos. 7,712,466 and 7,726,306 and U.S. patent application Ser. No. 11/611,425 and published as U.S. Patent Publication No. 2007/0137648, the disclosures which are hereby incorporated by reference in their entirety. These nebulizers are horizontally configured and include a venturi at a rainfall chamber.

SUMMARY OF THE INVENTION

A nebulizer includes a body having an air channel section and a nebulizer outlet configured to be received within an oral cavity of a patient. The body is formed from upper and lower portions. A medication reservoir is formed in the lower portion. A reservoir cover is supported by the lower portion of the body and covers the medication reservoir to form an enclosed medication reservoir in which the medication is contained and held. A nozzle assembly is supported by the reservoir cover and includes an air line having an inlet at one end and extending through the air channel section and having an outlet and a venturi nozzle at the outlet and having a venturi outlet. The air line, venturi nozzle and discharge outlet are horizontally oriented when in use and the venturi nozzle is located within a patient's oral cavity when the nebulizer is in use. A primary suction line extends from the medication reservoir to the venturi outlet through which medication is drawn upward and mixed with air passing through the venturi nozzle and nebulized for discharge through the nebulizer outlet. The venturi nozzle and suction line are formed together and replaceable as one unit.

The reservoir cover includes an upper extending diffuser located proximal or in front of the venturi nozzle to which nebulized medication and air from the venturi nozzle impact to aid in nebulization. The diffuser includes a vertical slot opening through which nebulized medication and gas pass. The diffuser includes a horizontal lock member and the outlet of the air line includes a top clip member adjacent the venturi nozzle and forms a locking slot that receives the horizontal lock member of the diffuser to snap lock the nozzle assembly and reservoir cover together. The lower body portion and reservoir cover includes snap fit members configured to snap fit the reservoir cover to the lower body portion.

In another example, the air line provides continuous pressure between the input end and outlet end of the air line. No medication is drawn upward through the suction line for nebulization and discharge through the nebulizer outlet until a predetermined negative inspiratory pressure is created from inhalation by a user to begin air flow through the venturi nozzle. At that time, medication is drawn upward through the suction line and nebulized by air flowing through the venturi nozzle to be discharged through the nebulizer outlet. The nebulization begins at a negative inspiratory pressure from about −3 cmH$_2$O to about −52 cmH$_2$O.

In another example, the medication reservoir is located within a patient's oral cavity when the nebulizer is in use.

The upper and lower portions of the body, the reservoir cover and nozzle assembly are formed from a plastic material.

In another example, an air flow sensor is positioned within the air channel section and configured to generate signals indicative of air flow generated by a patient's involuntary cough event occurring at nebulization. A processor is configured to receive signals from the air flow sensor and to evaluate the involuntary cough event.

BRIEF DESCRIPTION OF THE DRAWINGS

Other objects, features and advantages of the present invention will become apparent from the detailed description of the invention which follows, when considered in light of the accompanying drawings in which:

FIG. 1 is cross-sectional view of a nebulizer in accordance with a non-limiting example that is activated by negative inspiratory pressure and can be configured as a pediatric nebulizer in one non-limiting example and include in one embodiment a flow meter function.

FIGS. 2-3 are sectional views of the nebulizer shown in FIG. 1 and showing a flow diagram of the airflow at 2 L/min at standard temperature and pressure (STP).

FIGS. 4-5 are flow diagrams showing the airflow through the nebulizer of FIG. 1 at 2 L/min at −3 $cmH_2O$.

FIGS. 6-7 are flow diagrams showing the airflow through the nebulizer of FIG. 1 with 2 L/min at −15 $cmH_2O$.

FIGS. 8-9 are flow diagrams showing the airflow through the nebulizer of FIG. 1 with 2 L/min at −52 $cmH_2O$.

FIG. 10 is a diagram showing the pressure gradient in the nebulizer of FIG. 1 at standard temperature and pressure.

FIG. 11 is a diagram of the nebulizer of FIG. 1 showing the pressure gradient at −3 $cmH_2O$.

FIG. 12 is a sectional view of the nebulizer of FIG. 1 showing the pressure gradient at −15 $cmH_2O$.

FIG. 13 is a sectional view of the nebulizer of FIG. 1 showing the pressure gradient at −52 $cmH_2O$.

FIG. 14 is a sectional view of the nebulizer of FIG. 1 showing the medication flow upward at 2 L/min −3 $cmH_2O$.

FIG. 15 is a sectional view of the nebulizer of FIG. 1 showing the medication flow upward at 2 L/min −15 $cmH_2O$.

FIG. 16 is a sectional view of the nebulizer of FIG. 1 showing the medication flow upward at 2 L/min −52 $cmH_2O$.

FIG. 17 is a table showing respiratory pressures for the measured and predicted MIP and MEP for males and females.

FIG. 18 is a general environmental view of a child sucking on a pediatric nebulizer such as disclosed in FIGS. 19-22 in accordance with non-limiting examples.

FIG. 19 is a general environmental view of a pediatric nebulizer used by the infant shown in FIG. 18 in accordance with non-limiting examples.

FIG. 20 is a side sectional view in isometric of the pediatric nebulizer shown in FIG. 19 that engages the patient's mouth.

FIG. 20A is a more detailed view of the pediatric nebulizer body with the rainfall chamber, which includes an airflow sensor in accordance with non-limiting examples.

FIG. 21 is another side sectional view of a pediatric nebulizer in accordance with non-limiting examples.

FIG. 22 is another side sectional view of a different embodiment of a pediatric nebulizer in accordance with the non-limiting example.

FIG. 23 is a sectional view of another embodiment of the nebulizer in accordance with a non-limiting example and showing an airflow sensor such as a spinning fan wheel and associated with the main body, and a wireless module that includes a processor and transceiver that can receive measured airflow and wirelessly transmit data containing measured airflow to a separate device such as a handheld processing device in accordance with the non-limiting example.

FIG. 24 is a plan view of the nebulizer of FIG. 23 and showing an air flow sensor mounted within the air channel section of that nebulizer.

FIG. 25 is a cross-section view of another nebulizer configuration that provides air curtains and showing an air flow sensor mounted at the mixing end of the nebulizer in accordance with the non-limiting example.

FIG. 26 is a fragmentary plan view of a handheld processing device that can be used in conjunction with the nebulizers having the airflow sensors and which can be configured to wirelessly receive data containing air flow measurements, such as for measuring and processing data regarding the involuntary cough event.

FIG. 27 is a block diagram showing example components of a hand held processing device such as shown in FIG. 26, which can receive data from a nebulizer containing air flow measurements.

FIG. 28 is a side elevation view of the nebulizer shown in FIGS. 1-16.

FIG. 29 is an end elevation view of the nebulizer shown in FIG. 28.

FIG. 30 is a plan view of the nebulizer shown in FIG. 28.

FIG. 31 is a phantom diagram showing internal components of a portion of the nebulizer body that includes the air channel section, air line and vent in accordance with a non-limiting example.

FIG. 32 is a perspective view in partial cut-away of the nebulizer body showing components of the nebulizer body.

FIG. 33 is a top plan view of a portion of the nebulizer body shown in FIG. 32 and showing details of the vent in accordance with a non-limiting example.

FIG. 34 is another top plan view of the vent of FIG. 33.

FIG. 35 is a partial, sectional view of the nebulizer of FIG. 28 in accordance with a non-limiting example.

FIG. 36 is a perspective view of another embodiment of the nebulizer in accordance with a non-limiting example.

FIG. 37 is a partial fragmentary view of the nebulizer shown in FIG. 36 and showing the upper portion of the body removed and showing the reservoir cover and the nozzle assembly supported by the reservoir cover and snap fit together.

FIG. 38 is a sectional view of the nebulizer taken along line 38-38 of FIG. 36.

FIG. 39 is a perspective view of the nozzle assembly and showing the suction line connected to the venturi nozzle and formed together and replaceable as one unit in accordance with a non-limiting example.

DETAILED DESCRIPTION OF THE PREFERRED EMBODIMENTS

Different embodiments will now be described more fully hereinafter with reference to the accompanying drawings, in which preferred embodiments are shown. Many different forms can be set forth and described embodiments should not be construed as limited to the embodiments set forth herein. Rather, these embodiments are provided so that this disclosure will be thorough and complete, and will fully convey the scope to those skilled in the art.

In accordance with a non-limiting example, the nebulizer uses a vent that is formed in the nebulizer body and communicates with the air channel section and medication reservoir to vent the air channel section and medication reservoir to outside ambient air. A primary suction line extends from the medication reservoir to the low pressure mixing chamber through which medication is drawn upward and mixed with air passing through the venturi nozzle and nebulized for discharge through the nebulizer outlet. This vent is configured to vent the air channel section and medication reservoir to atmospheric pressure such that at standard temperature and pressure (STP), a differential pressure results between the venturi nozzle and medication reservoir such that no medication is drawn upward through the primary suction line for nebulization and discharge through the nebulizer outlet into a negative inspiratory pressure is created from inhalation by a user. The air line extends through the air channel section and includes the venturi nozzle and is configured at its end to form the low pressure mixing chamber. Air is continually pressurized in the air line from an air source, but at a low pressure that works in conjunction with the vent such that at standard temperature and pressure (STP), the differential pressure resulting between the venturi nozzle and medication reservoir is such that no medication is drawn upward through the primary suction line for nebulization and discharge. The various pressure flow diagrams in FIGS. 2-16 show the various applied pressures and suction and when medication is drawn upward through the primary suction line and nebulization occurs and the forces involved, such as through inhalation.

In accordance with a non-limiting example, the nebulizer initiates nebulization upon inhalation. The nebulizer is configured as an intra-oral nebulizer and run with half liter air flow using the low pressure air source. Nebulization is activated by a patient breathing and inhaling. Micro amounts of medication are released only when required during inspiration and will not flow into the gut because of the low velocity and the configuration of the nebulizer as an intra-oral nebulizer. This is also aided because the venturi nozzle is positioned intra-orally. Because most dosages of the nebulized medication go into the lungs upon inhalation, if dangerous drugs are being inhaled during nebulization, it is not likely that they will be released into the ambient and surrounding air to harm others.

There are various mechanics of jet nebulizers that should be understood. A jet nebulizer is a device that is used to deliver medication to the respiratory system using a supplied air source. Traditional nebulizers have a vertical column of air passing through a reservoir of medication, which has a separation at the top of the nozzle allowing the air and medication to mix. This mixture accounts for the initial medication droplet formation due to the drastic change in surface area and aerodynamic effects of the mixture region. This initial droplet formation can be estimated from a linear stability analysis and an aerodynamic loading analysis using parameters such as the Reynolds number, Mach number, and Weber number. This initial droplet formation in this region is normally not sufficient for the desired deposition of the medication in the respiratory tract. To further reduce the droplet size, these droplets travel at high speed and collide with a baffle. This impact energy greatly reduces the droplet size to an acceptable level for deposition of medicine.

This traditional approach has several draw backs. One of the primary factors is that additional medication is required to deliver the proper dose to the desired region of the respiratory tract. Droplet formation occurs outside of the mouth in traditional devices and then has to travel through tubes, masks and the mouth. This additional travel period allows more particle to particle interaction. These particle collisions allow for particle combining, creating a larger diameter. Deposition will not occur with these larger diameter droplets, and therefore waste occurs.

Reducing these particle interactions is possible using the nebulizer as shown in FIG. 1. This nebulizer operates to nebulize in the mouth and operate as a horizontal nebulizer just outside of the mouth to allow for smaller droplet sizes for deposition at a lower zone in the respiratory tract and use less medication, resulting in less waste.

The illustrated nebulizer operates such that the differential pressures result with the nebulizer operating at a flow condition when at standard atmospheric pressure. Nebulization does not occur. As pressure decreases within the nebulizer due to inhalation, the differential pressures result in medication as fluid to flow up the nozzle.

Figure 2:
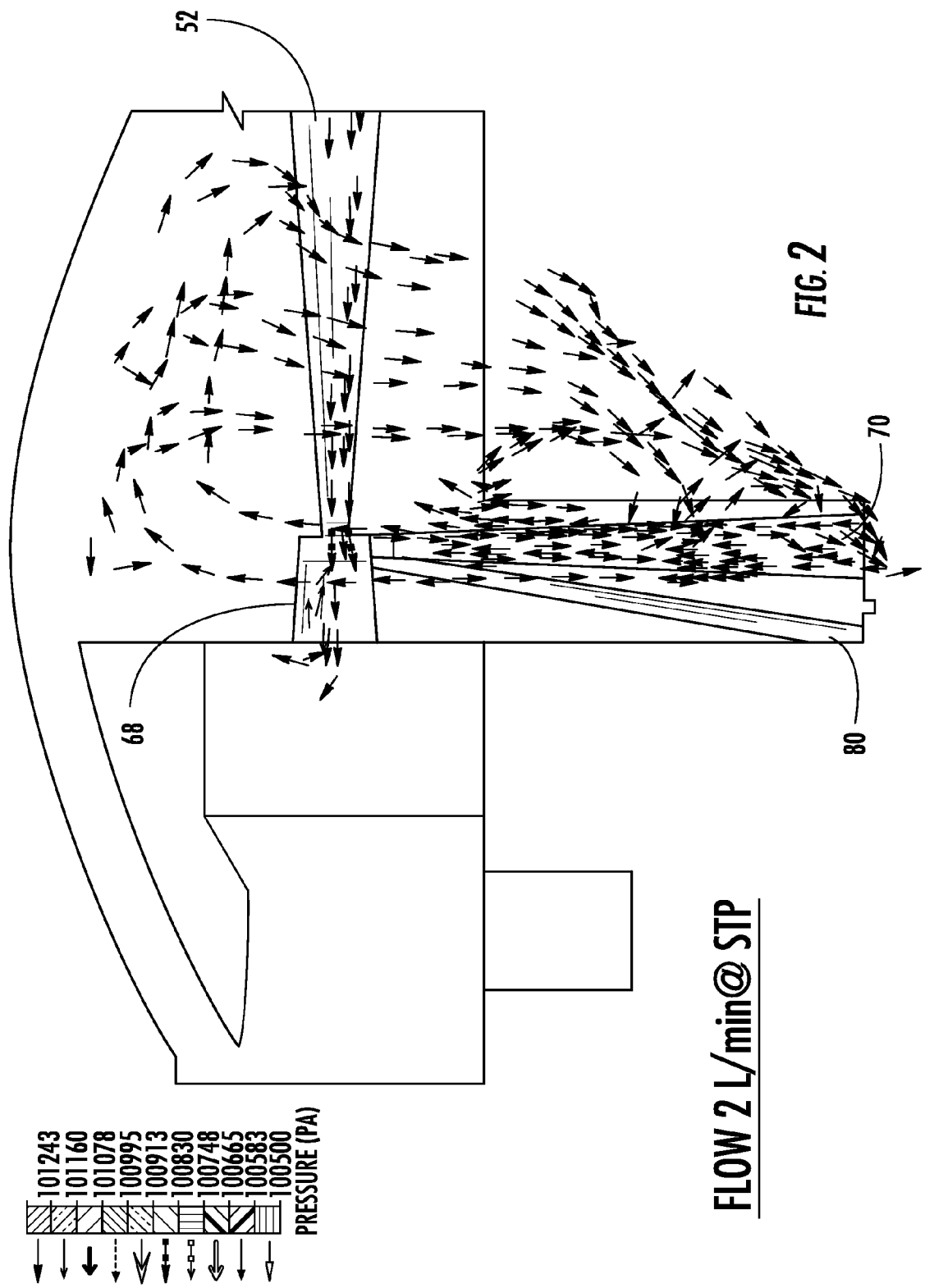
Figure 3:
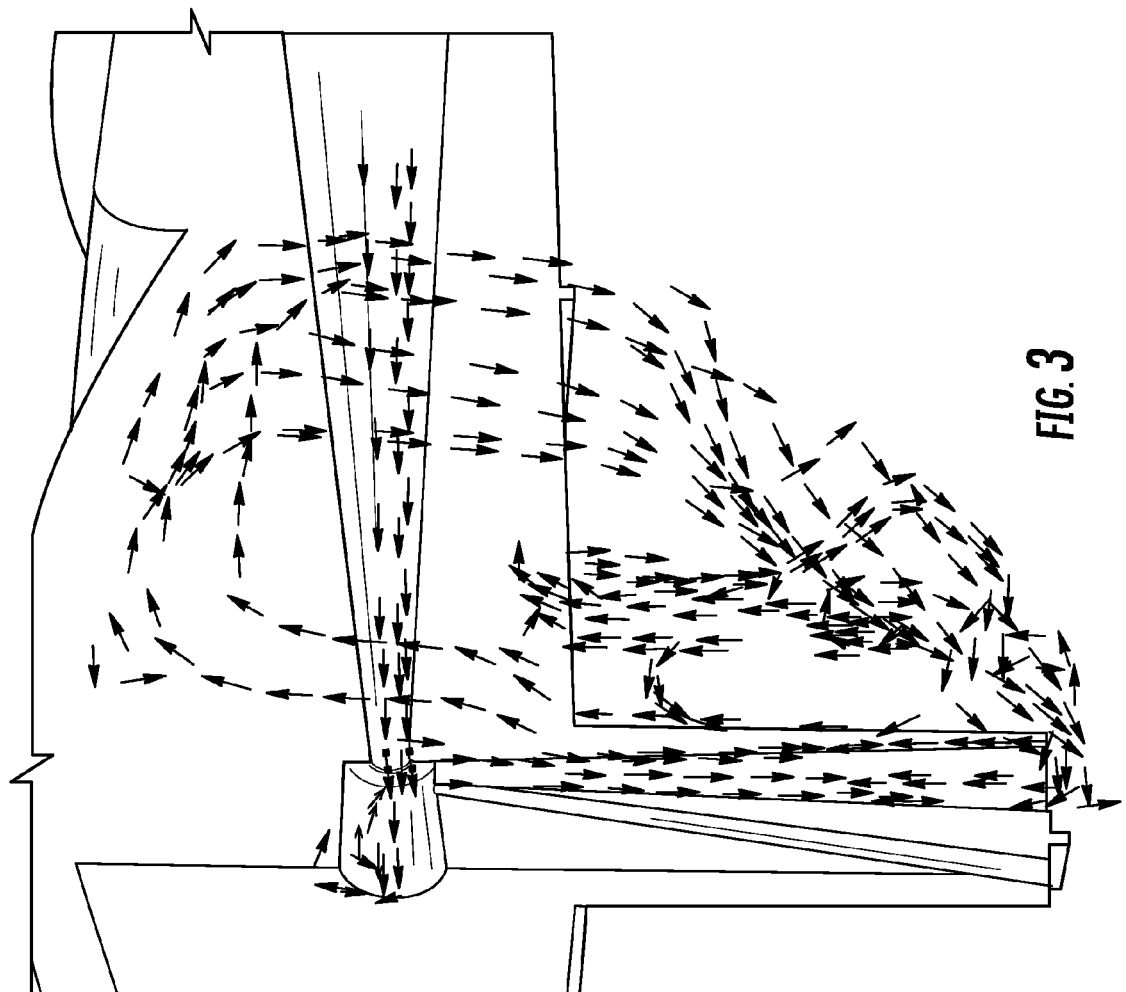
Figure 4:
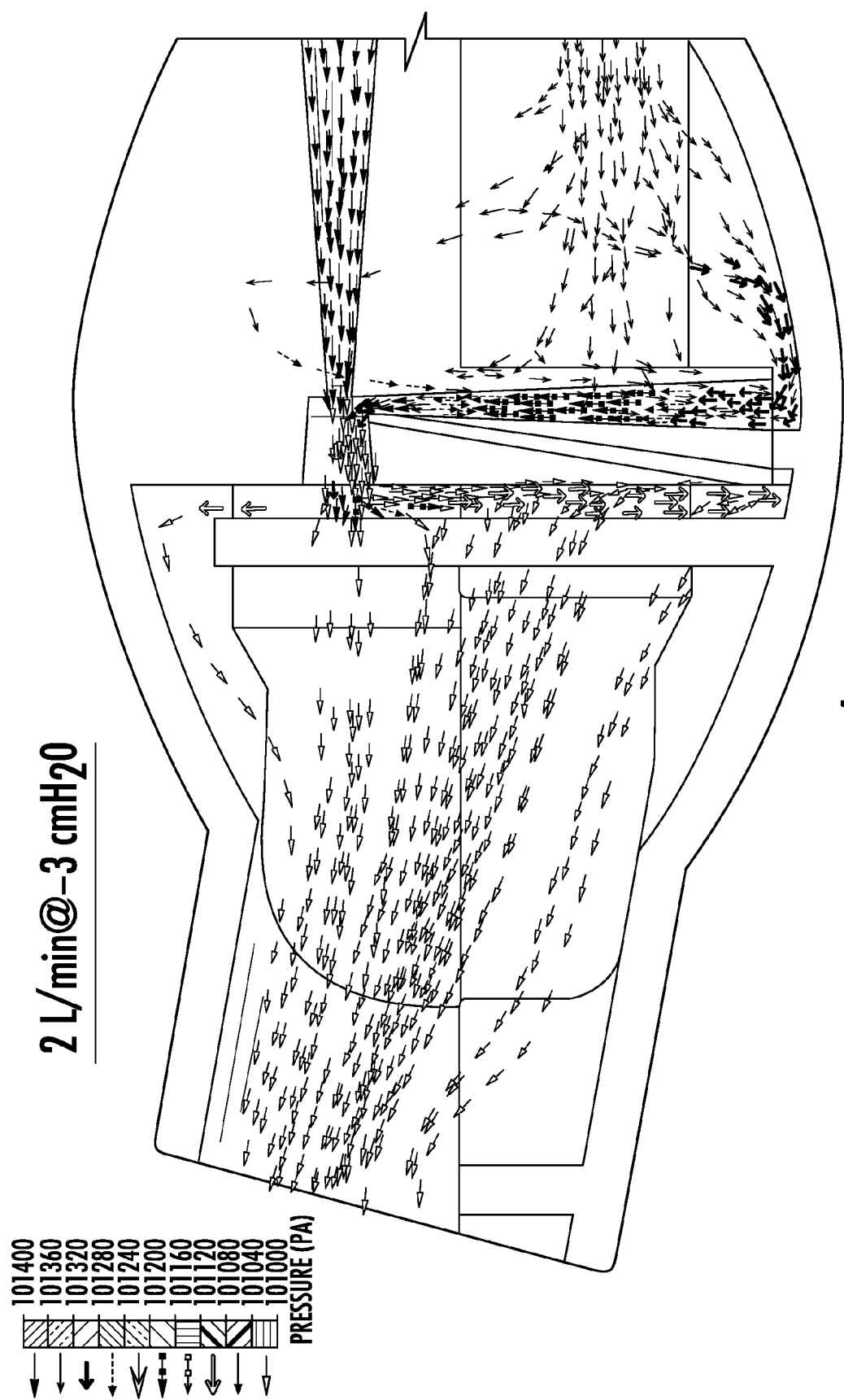
Figure 5:
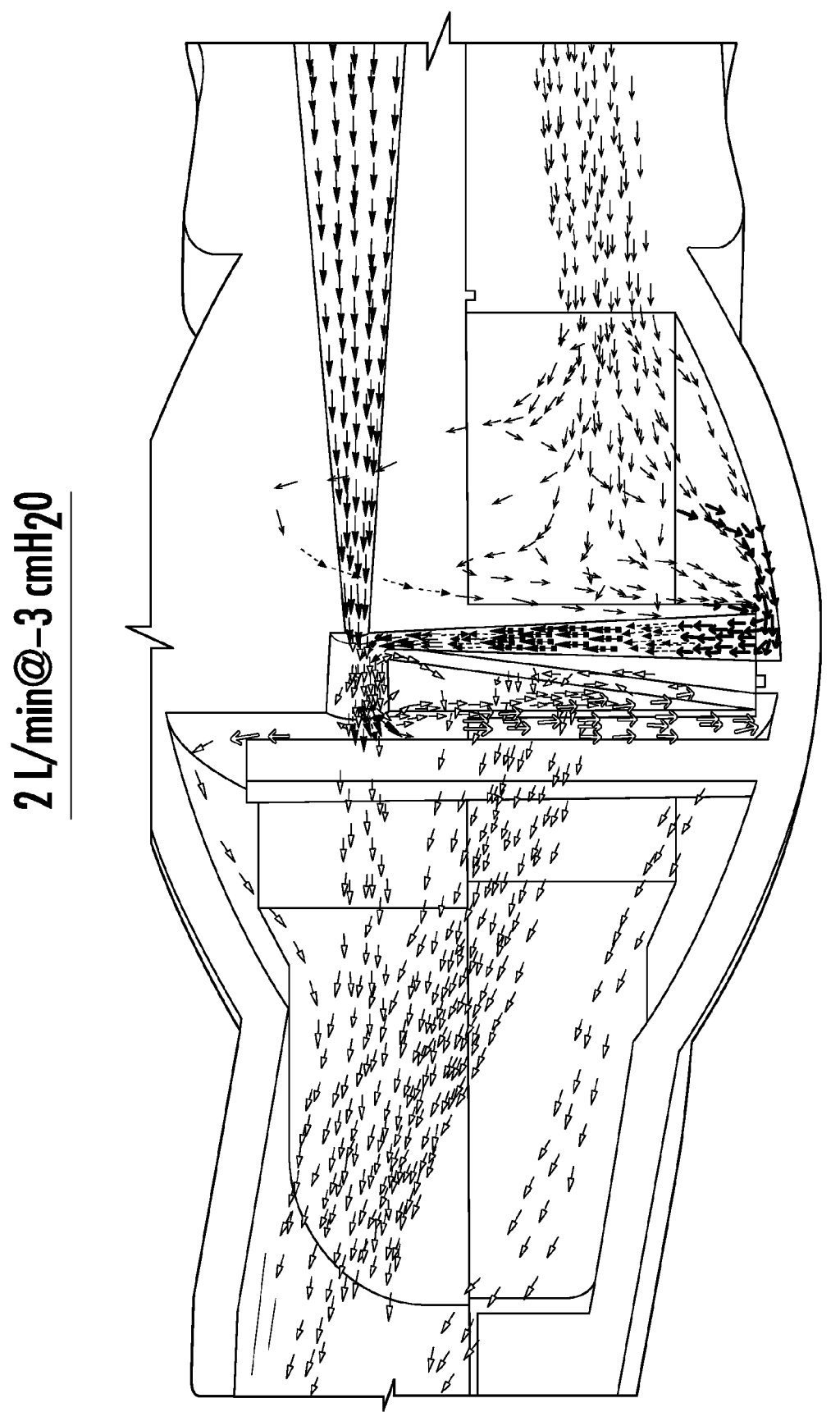
Figure 6:
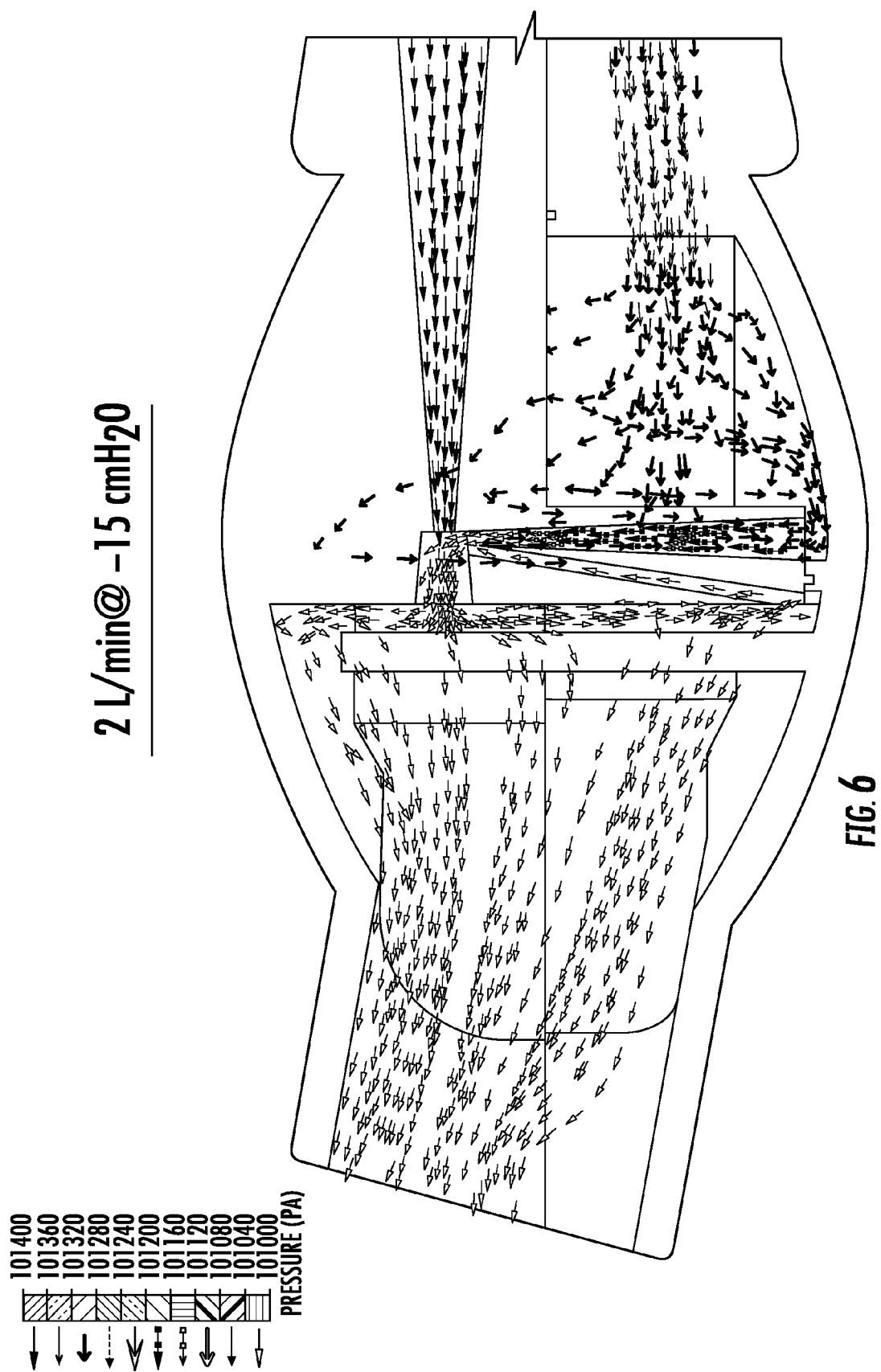
Figure 7:
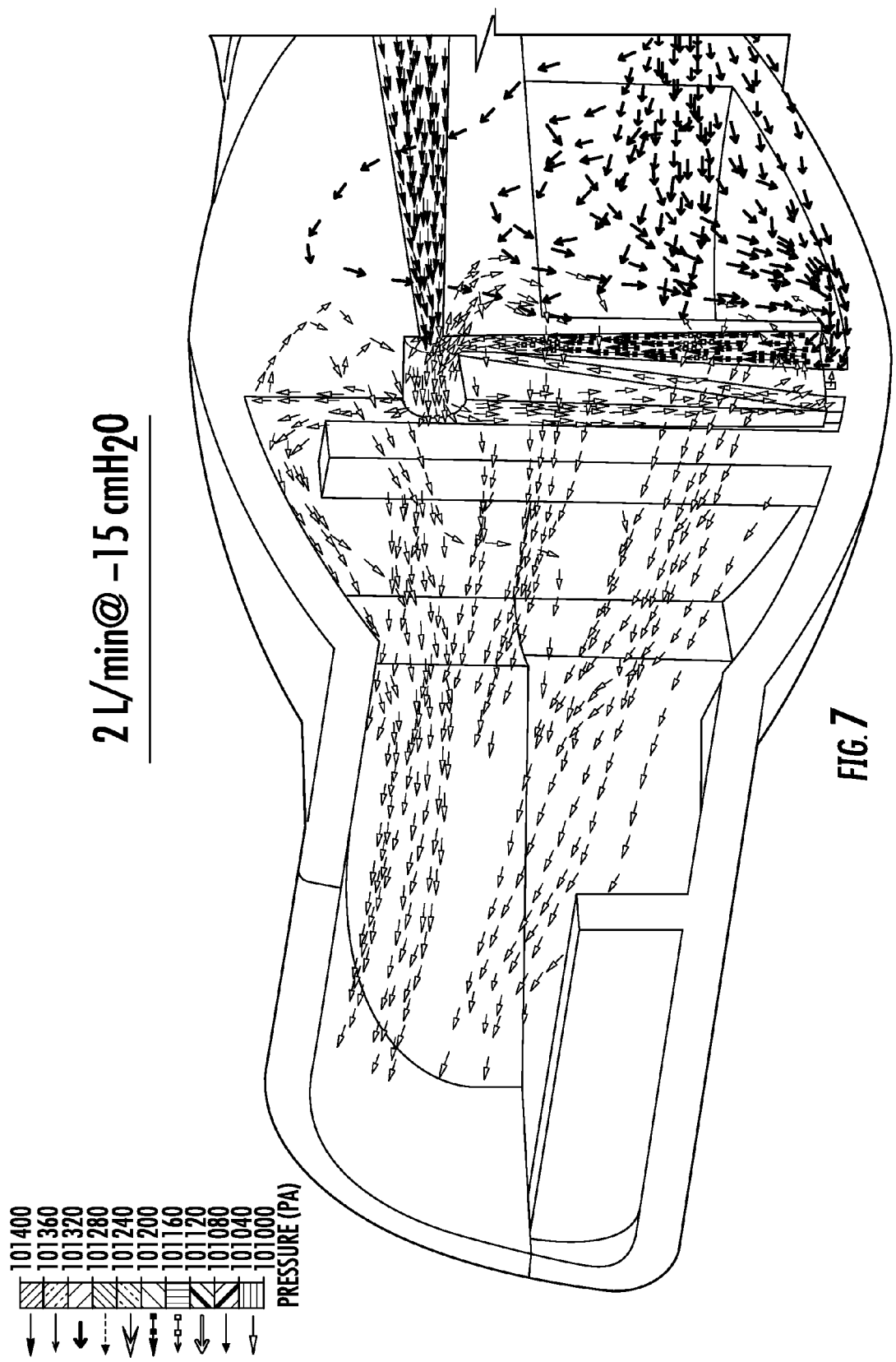
Figure 8:
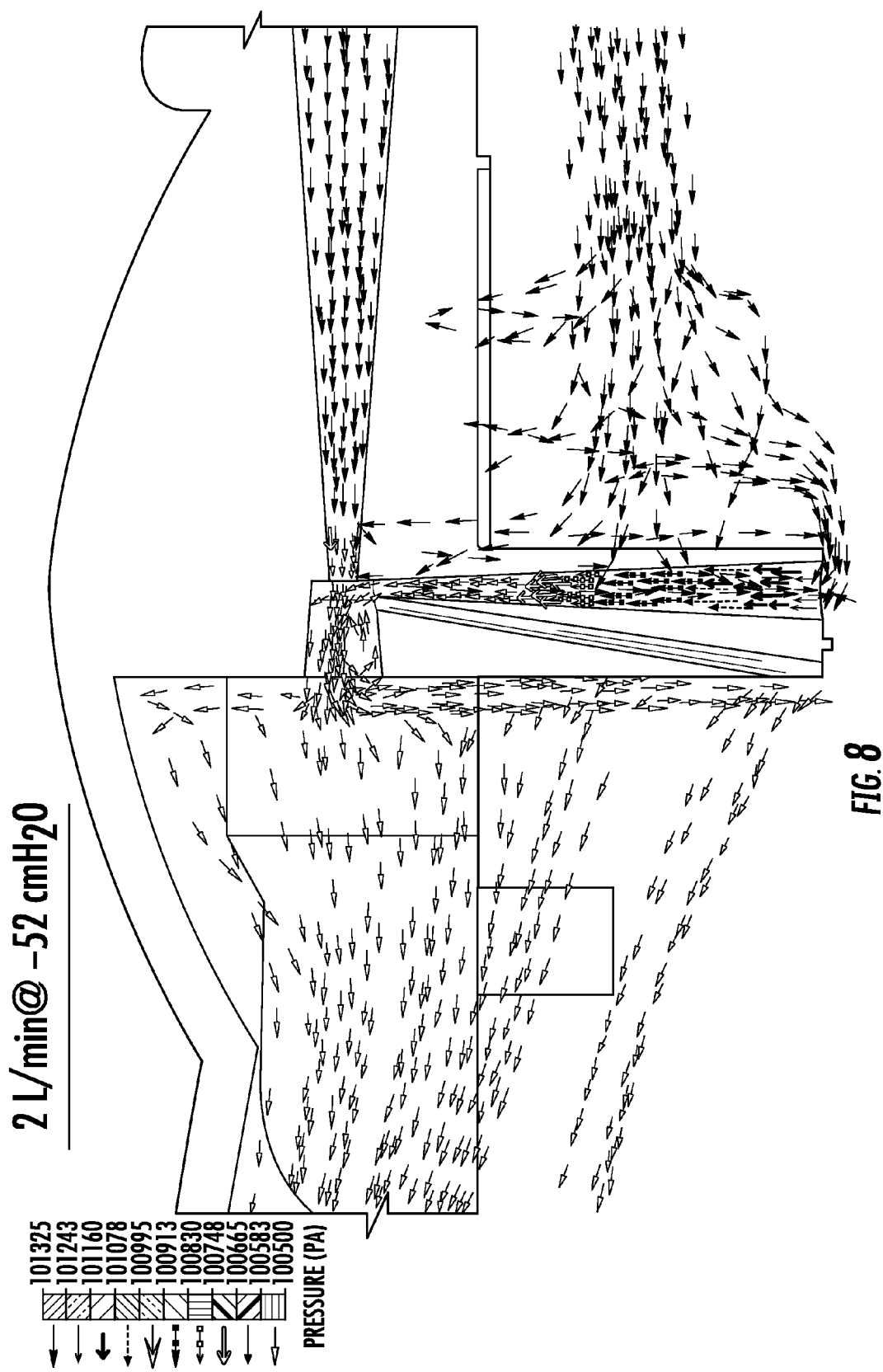
Figure 9:
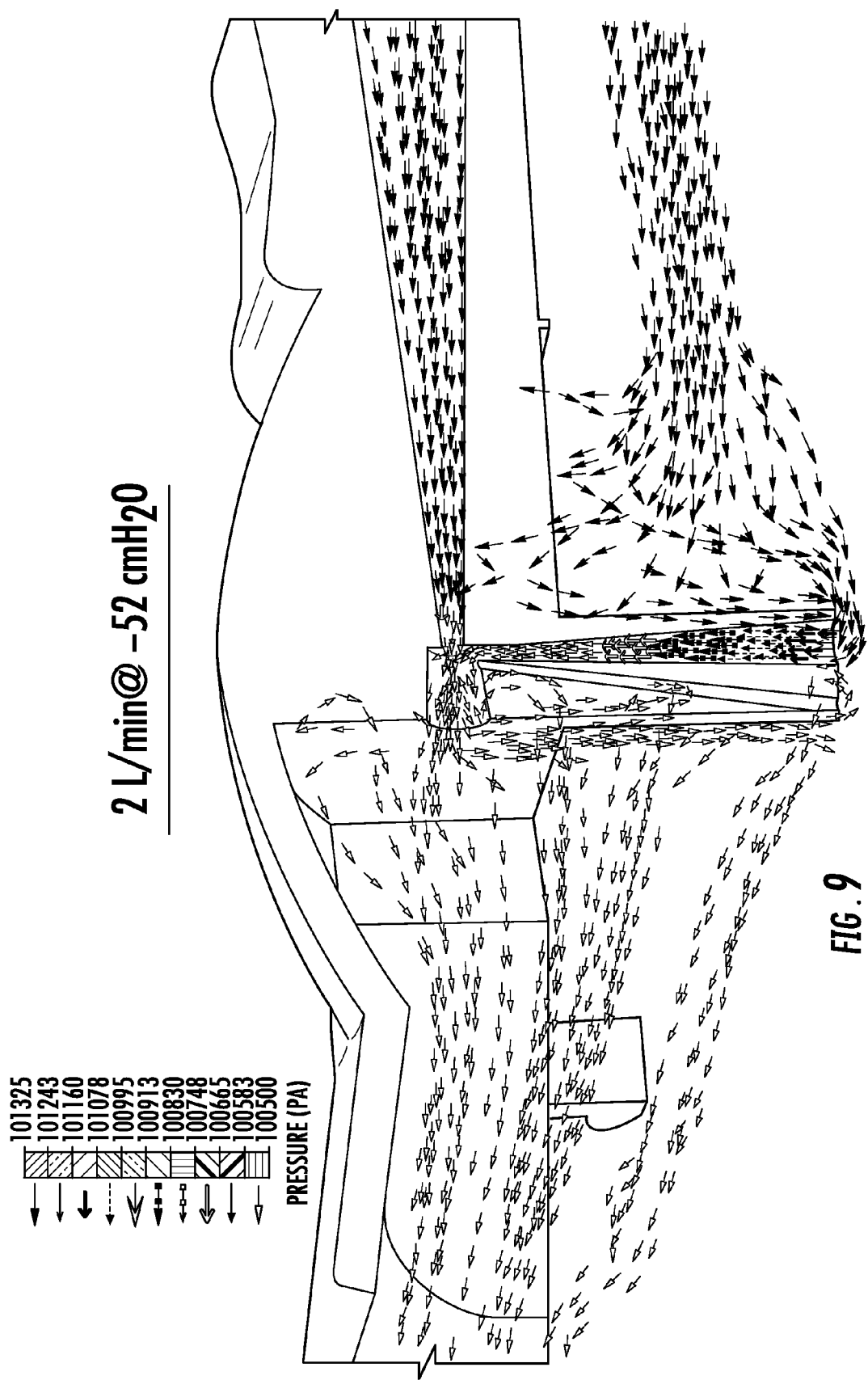
Figure 10:
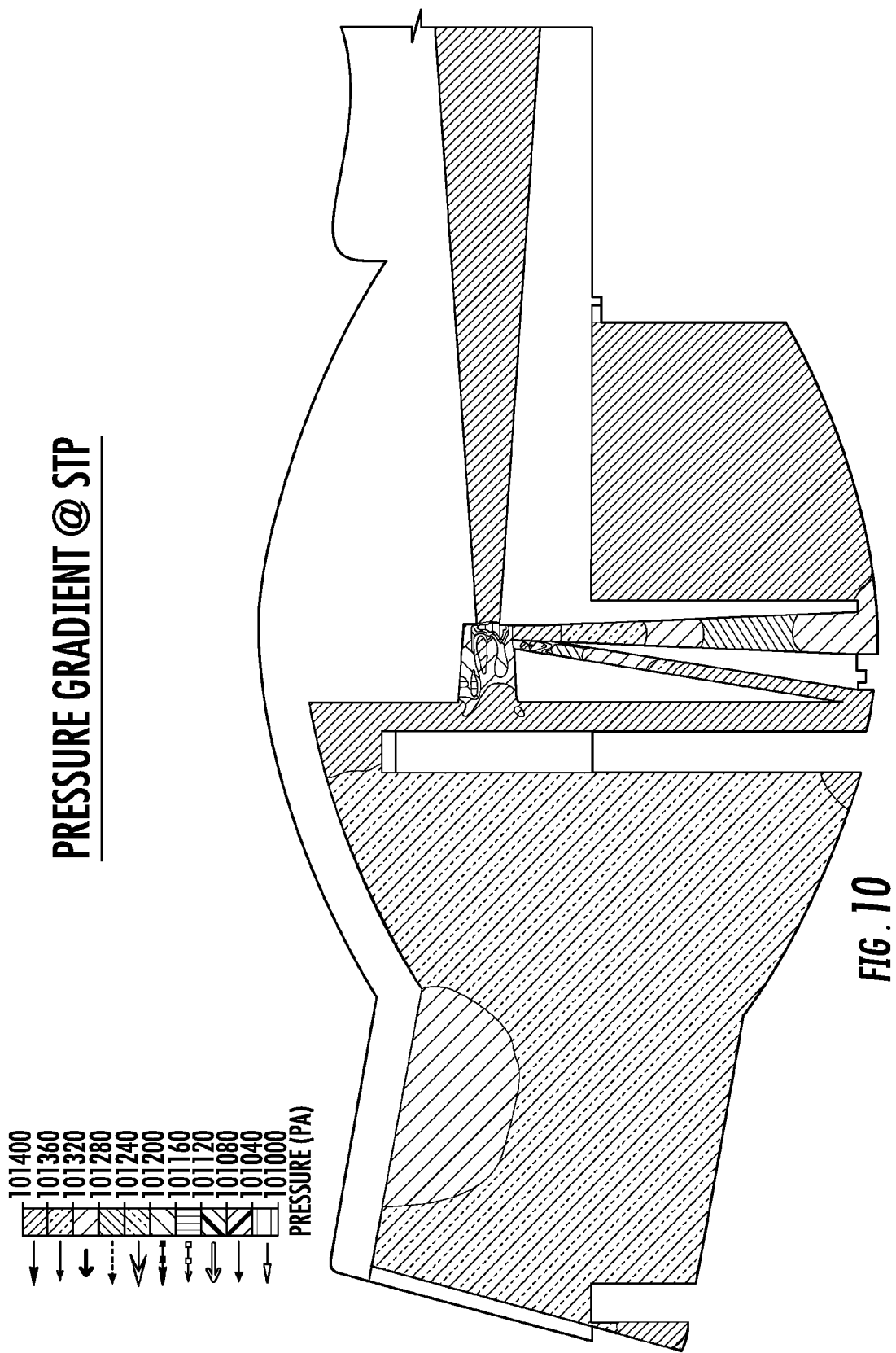
Figure 11:
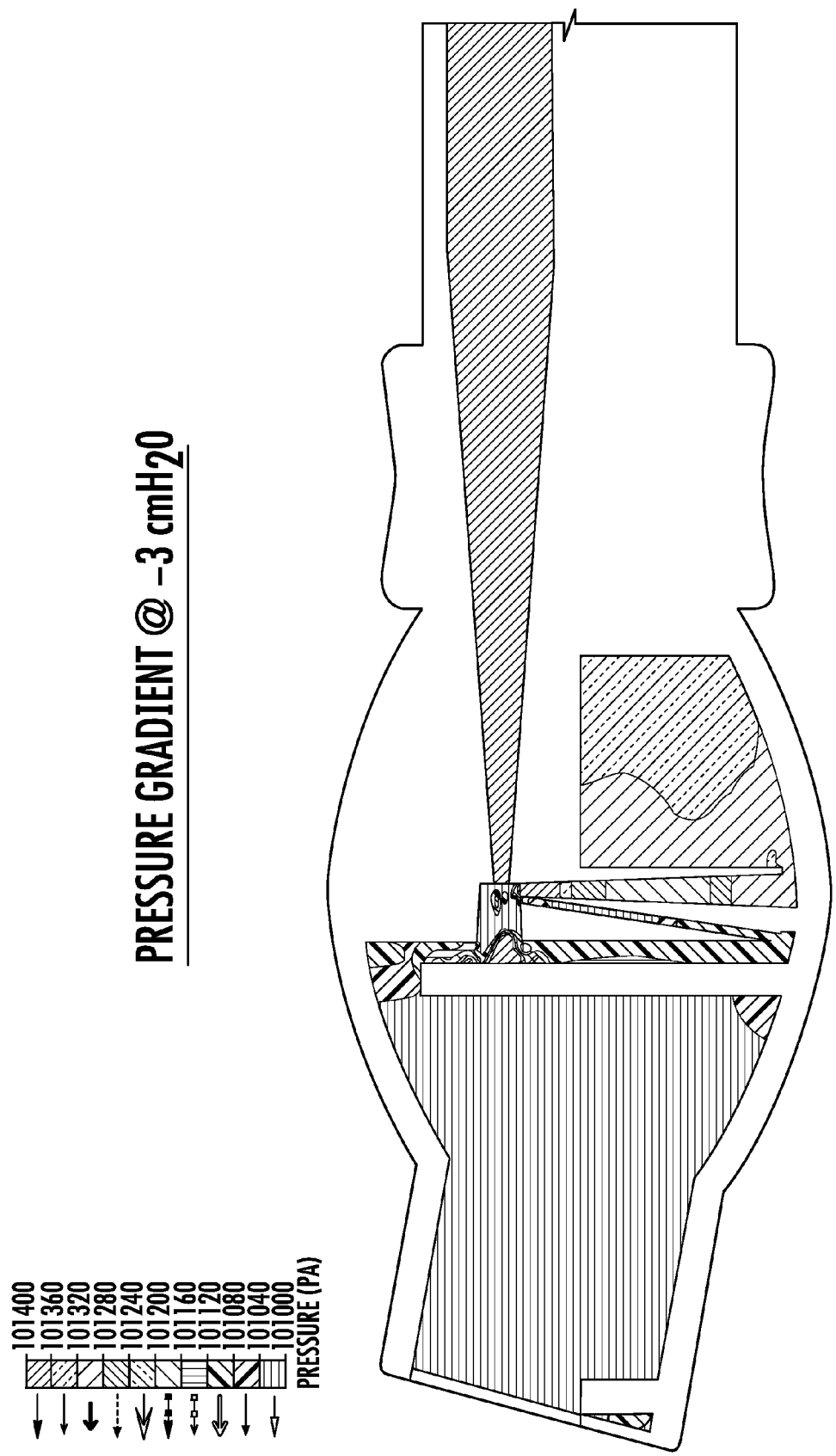
Figure 12:
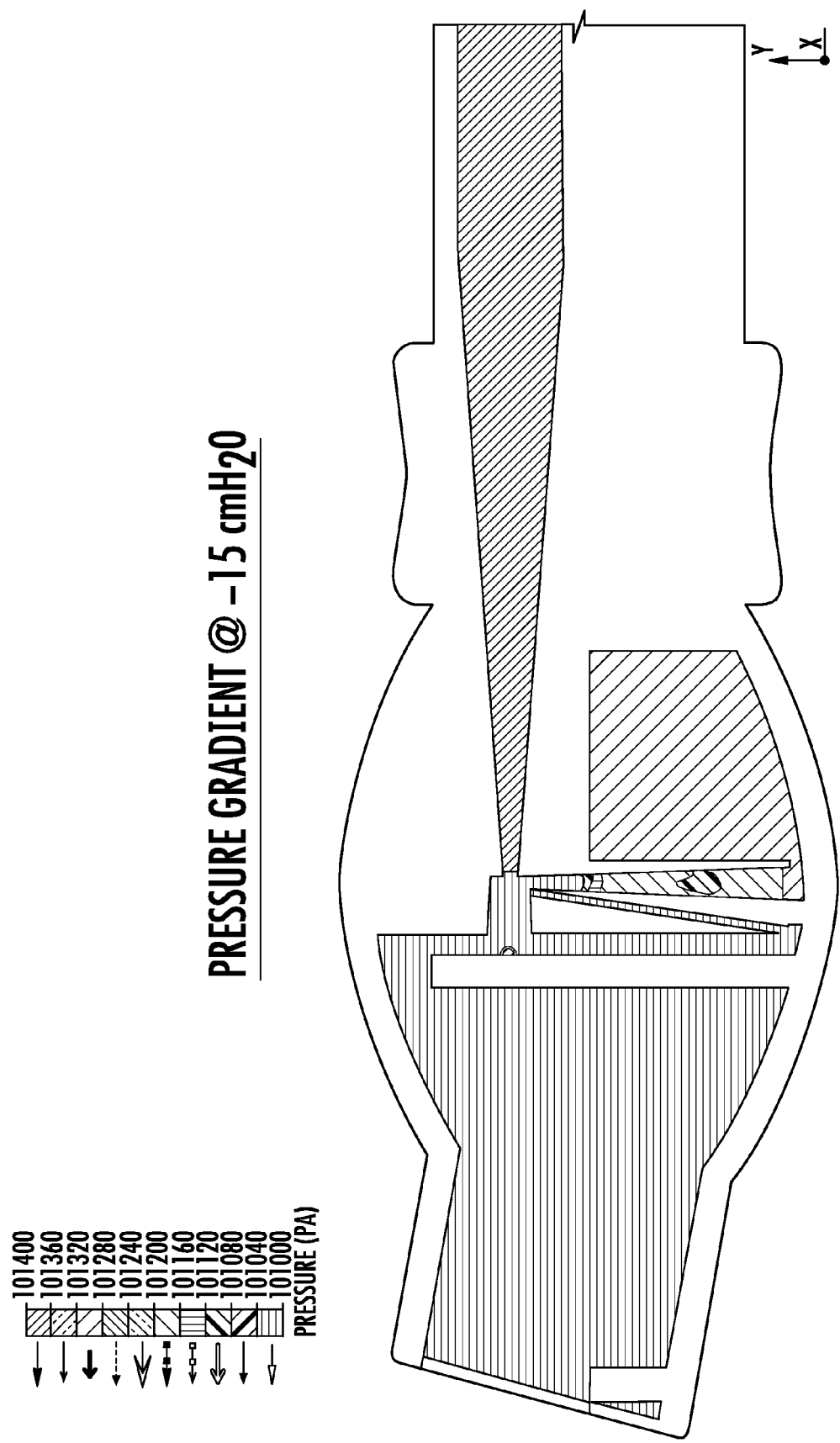
Figure 13:
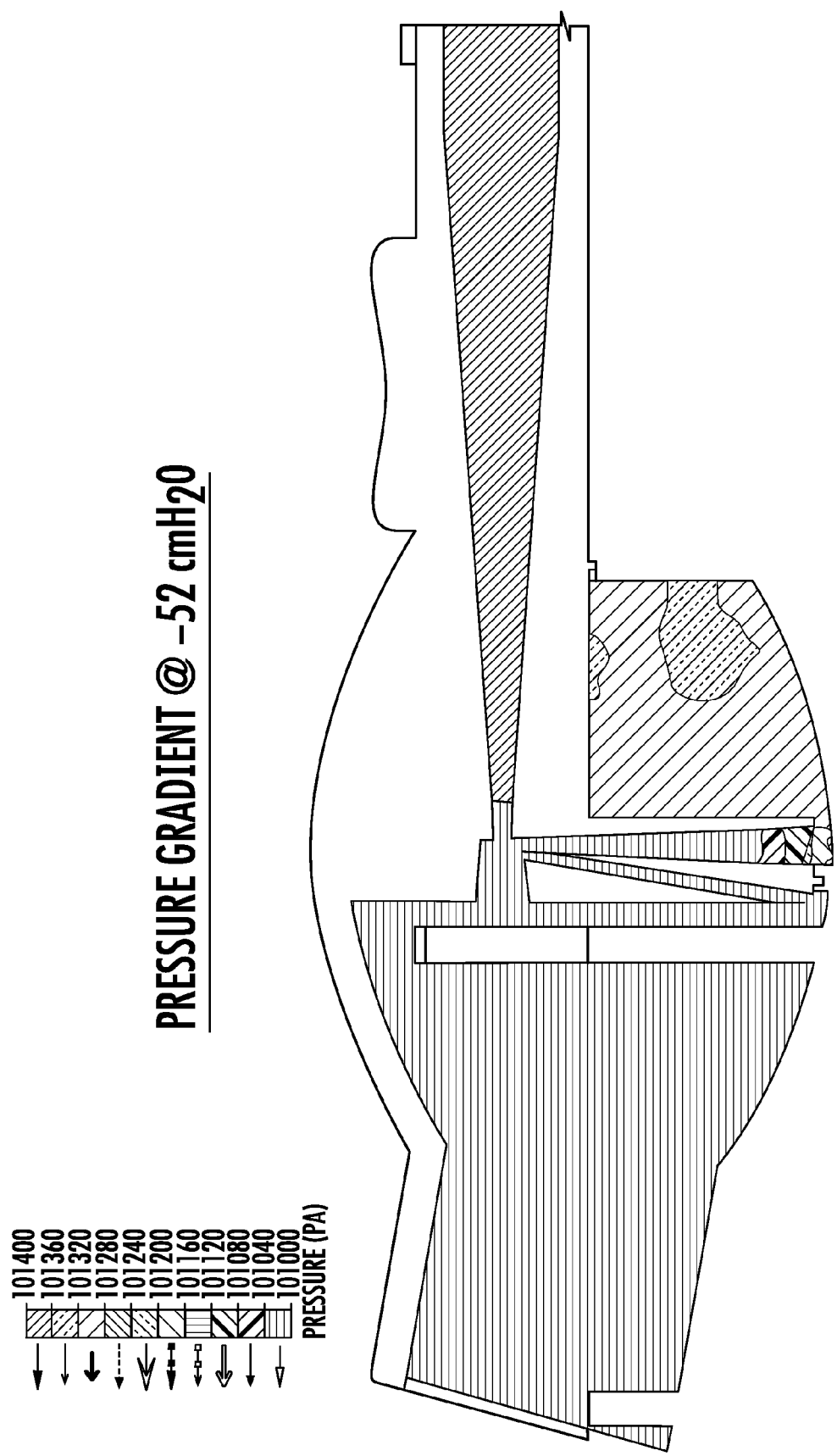
Figure 14:
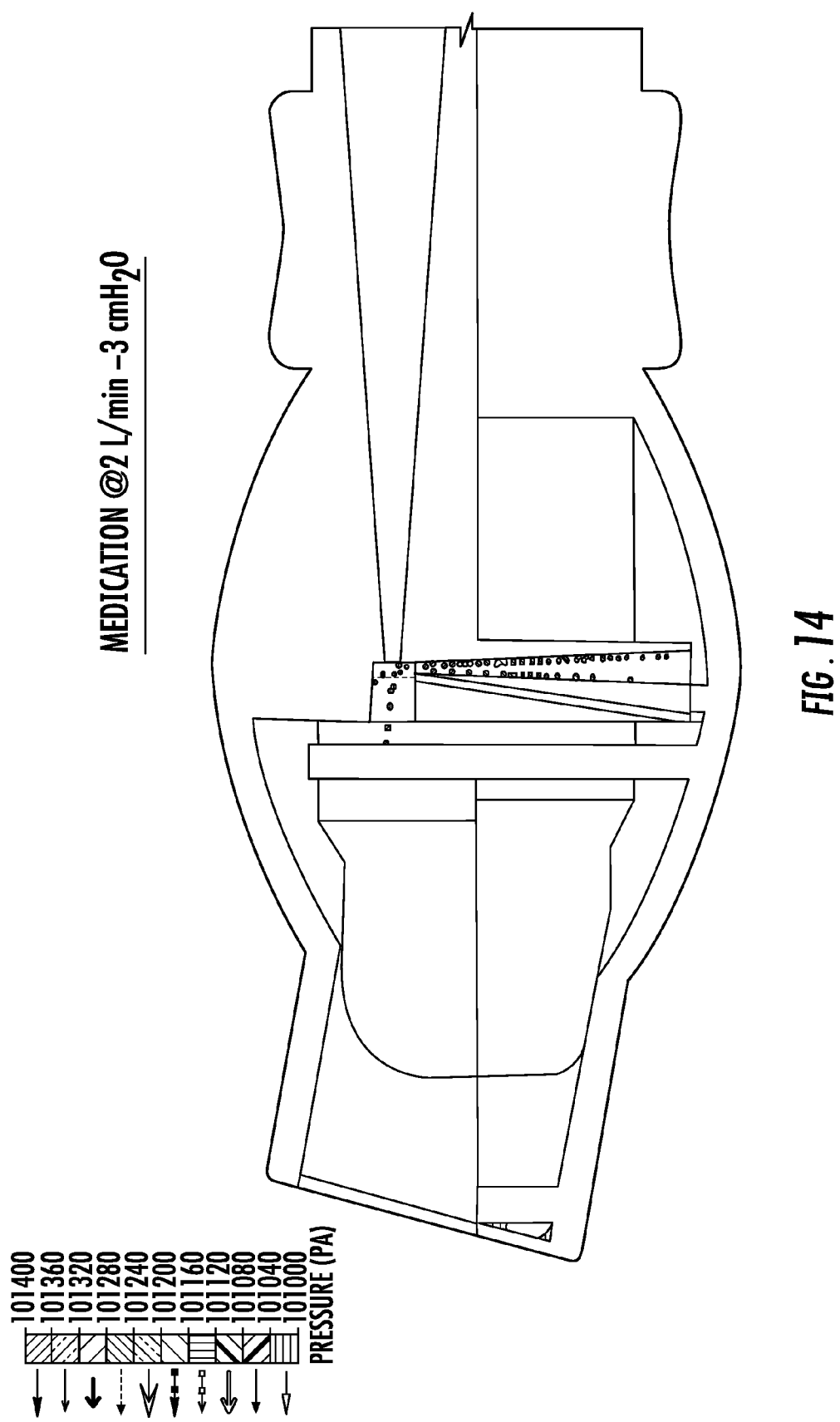

Referring now to FIG. 1, there is disclosed an improved horizontal nebulizer 50 having a nebulizer body 51 with a breath activated venturi nozzle 52 that together with other components creates the differential pressure between the venturi nozzle 52 and the medication reservoir 58 when air is passed through the venturi nozzle 52. The nebulizer body 51 includes an air channel section 54 and medication reservoir 58 and a nebulizer outlet 60 configured to be received within an oral cavity of the patient. The nebulizer body is generally horizontally configured and includes a mouthpiece portion 62. In one embodiment, a pacifier housing 64 is added as shown by the dashed line, to form a pacifier or lollipop configuration at the nebulizer outlet. An air line 66 extends into the air channel section and includes the venturi nozzle 52 that is configured with the air channel section to form at its end a low pressure mixing chamber 68. FIGS. 2 and 3 show in greater detail the air line 66 and venturi nozzle 52 that are configured with the air channel section to form that low pressure mixing chamber, which is somewhat conically shaped.

A primary suction line 70 extends from the medication reservoir 58 to the low pressure mixing chamber 68 through which medication is drawn upward and mixed with air from the venturi nozzle 52 and nebulized for discharge through the nebulizer outlet 60. A compressed air line 72 can connect to the end of the body via an appropriate fitting 74. The venturi nozzle 52, low pressure mixing chamber 68 and air channel section 54 are configured such that at standard temperature and pressure (STP), a differential pressure results in no medication that is drawn upward through the primary suction line 70 for atomization, and none discharged through the nebulizer outlet, until a negative inspiratory pressure is created from inhalation by a user.

Figure 26:

As explained below, nebulization begins at a negative expiratory pressure from about −3 cmH$_2$O to about −52 cmH$_2$O. The venturi nozzle 52 is positioned at a location to be placed within a patient's oral cavity when the nebulizer in use and received in the mouth of the user. As illustrated, a rainfall chamber 76 is formed within the body 51 at the air channel section 54 into which the venturi nozzle 52 and low pressure mixing chamber are formed. As further illustrated, a diffuser 78 acts an impactor upon which the nebulized medication and air exiting the venturi nozzle and low pressure mixing chamber impacts to aid in nebulization. A secondary suction line 80 is formed within the rainfall chamber 76 and draws nebulized medication that had dropped down after impacting the diffuser or impactor. A better view of the secondary suction line is shown in FIGS. 2 and 3. In another example, an airflow sensor 82 can be positioned within the air channel section at the nebulizer outlet and configured to generate signals 83 indicative of air flow generated by a patient's involuntary cough event occurring at nebulization. A processor 84 could be associated with the nebulizer or a separate unit such as a handheld unit as shown in FIG. 26. This processor can receive signals and evaluate the involuntary cough event as explained in greater detail below.

The dashed lines in FIG. 1 show that the nebulizer outlet can be configured as a infant pacifier and be formed as a housing or lollipop. In another example, it is possible for a housing to enclose the body and have an end adjacent to the nebulizer outlet configured as an infant pacifier such as shown relative to FIGS. 21 and 22.

When the nebulizer is operating at a flow condition and at standard atmospheric pressure (STP), the differential pressures cause no fluid flow from the medication reservoir upward through the primary suction line into the low pressure mixing chamber. As the pressure decreases within the nebulizer due to inhalation, i.e., resulting from the negative inspiratory pressure, the differential pressure results in medication flowing up into the low pressure mixing chamber and air flowing through the venturi nozzle.

There is illustrated the medication reservoir 58 that includes the primary suction line where the medication is drawn up into the low pressure mixing chamber and air flows through the venturi nozzle. The nebulizer includes a breath activated venturi. Although the venturi is positioned for intra-oral use, it is not necessary to be in that position and can be located outside the oral cavity. The medication is released during breath activation as a horizontal nebulizer compared to an updraft style. Various medications could be mixed during the intake cycle. The nebulizer in accordance with a non-limiting example is an improvement over those prior art nebulizers that are actuated by pressing a valve for a user regulator while nebulizing.

In the nebulizer shown in FIG. 1, the flow through the venturi nozzle 52 is not activated until there is a negative inspiratory pressure, such as created from inhalation by the patient. In this nebulizer, air pressure is continuous, but nebulization is not. The rainfall chamber 76 is provided, but at STP, there is no flow of medication. At about −3 cm negative pressure, the negative suction actuates air flow and medication to be drawn upward through the primary suction line. When this occurs, the nebulized solution extends from the low pressure mixing chamber 68 and impacts the diffuser 78, i.e., impactor and some droplets fall to be picked up by the secondary suction line 80. There are no residual drops, condensation or agglomeration of nebulized medication that forms in front of the rain chamber, which could result in poor nebulization and air being drawn in by the patient. It is recirculated as a true nebulized medication.

In one example, the average pressure begins nebulizer operation at −52 cm with a 2 liter a minute flow rate. It is possible to begin flow at −3 cm negative pressure, but that has been found to be too sensitive. In another example, the nebulizer is configured to begin flow at −15 cm corresponding to −1 bar. The venturi nozzle and other components of the nebulizer as shown in FIG. 1 can be designed to begin flow from −3 to −100 cm within the venturi nozzle. The nebulizer is a jet nebulizer that requires the negative inspiratory pressure to allow the venturi to begin operating. The medicine fluid will not pass into the airstream until the flow begins through the venturi nozzle. Air is blowing at rest, but no venturi operation with flow occurs until a negative inspiratory pressure is supplied in front of the venturi nozzle at the air channel section to initiate the venturi effect and draw the medication up into the jet stream at the low pressure mixing chamber. As long as the negative inspiratory pressure is applied, there will be flow. If the negative inspiratory pressure stops, there is no flow. One nebulizer configuration is for a 5 liter per minute air flow, but the nebulizer can be configured for 2 liter up to 15 liter air flow. When the venturi nozzle begins operation, the medication hits the diffuser or impactor and some droplets fall downward and are drawn up by the secondary suction line.

The nebulizer shown in FIG. 1 operates when there is negative inspiratory pressure that activates the air flow through the venturi nozzle and into the low pressure mixing chamber. It does not matter if the venturi nozzle is inside or outside the mouth. It is also not a timed type of nebulizer such as with processor monitored breathing or arranging nebulization based on breathing cycles and valves. With the nebulizer shown in FIG. 1, the patient inhales at a certain amount of pressure and the air flow through the venturi nozzle. In one example, it is one bar corresponding to −15 cm of water. The average may be −53 cm and the first −15 cm could activates flow through the venturi nozzle. When inhalation pressure drops below −15 cm, then flow through a venturi nozzle ceases.

FIG. 17 is a chart showing respiratory pressures for measured and predicted MIP (maximal inspiratory pressure) and MEP (maximal expiratory pressure), as an example with the nebulizer shown in FIG. 1.

FIGS. 2-16 are sectional views of the nebulizer of FIG. 1 and showing the air flow through the nebulizer of FIG. 1 at STP and different pressures as showing the variations in pressure and air flow. A flow of 2 L/min is illustrated in most of the diagrams and pressure gradients are shown at STP and other pressures. These figures also show the pressure gradients and medication flow upward through the primary suction line at different inspiratory pressures.

Figure 28:
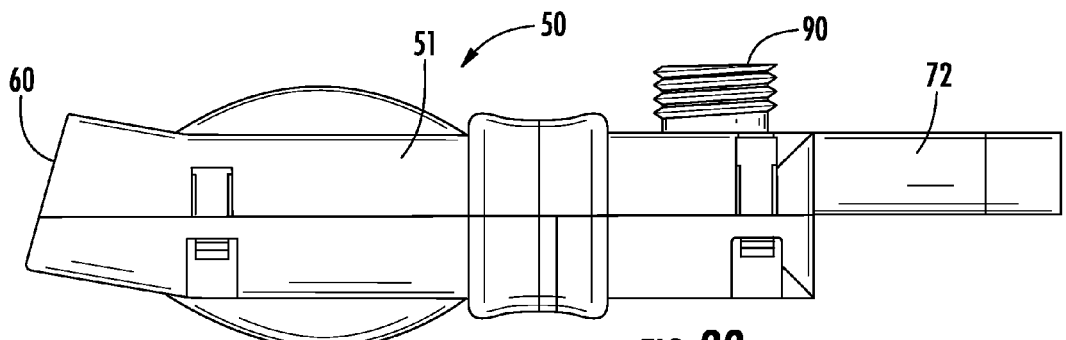

FIGS. 28-35 are other views of the nebulizer 50 such as described at FIGS. 1-16. FIG. 28 shows a side elevation view of the nebulizer 50 with a top screw fitting 90 on the nebulizer body 51 that receives a medication reservoir such as a vial or medicine container that may be screwed onto the fitting 90. Other types of fittings may be used. An internal member (not shown) pierces any medicine container to allow medication from the medicine container to flow into the reservoir.

Figure 29:
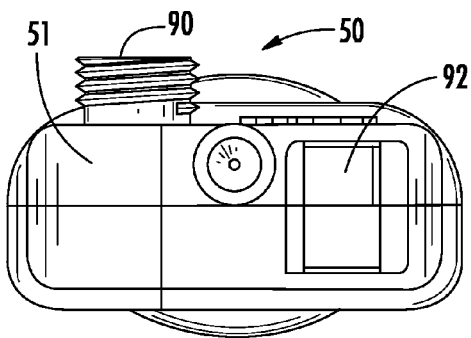
Figure 30:
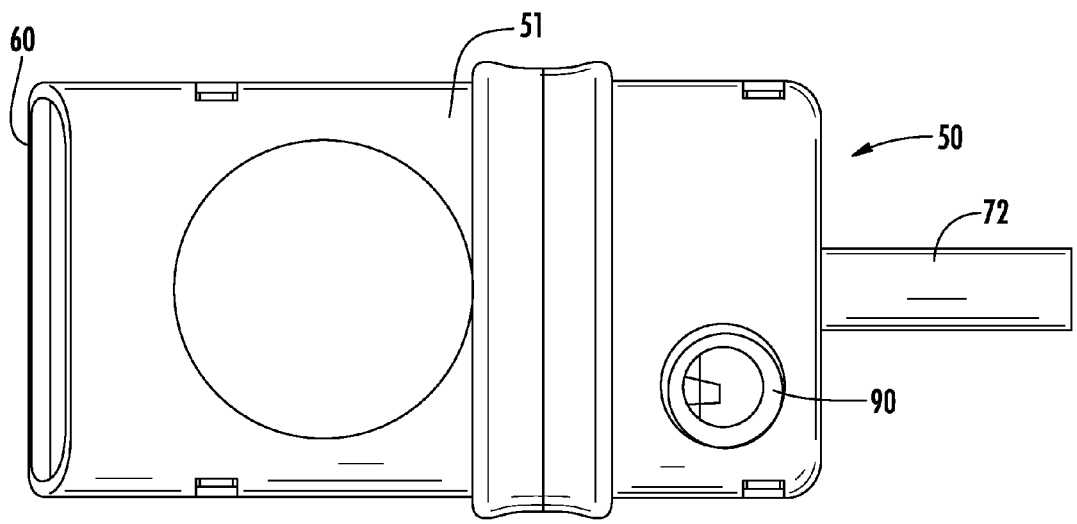

FIG. 29 is an end elevation view of the nebulizer 50 showing the air line 66 and the vent 92 formed in the nebulizer body 51 that communicates with the air channel section 54 and medication reservoir 58 to vent the air channel section 54 and medication reservoir 58 to outside ambient air. The vent may be formed as a valve. The air line 66 receives continuous pressurized air, but it is low pressure. The vent allows balancing of pressures at STP and with the pressurized air so that upon inhalation of the nebulizer, medicine is nebulized.

Figure 31:
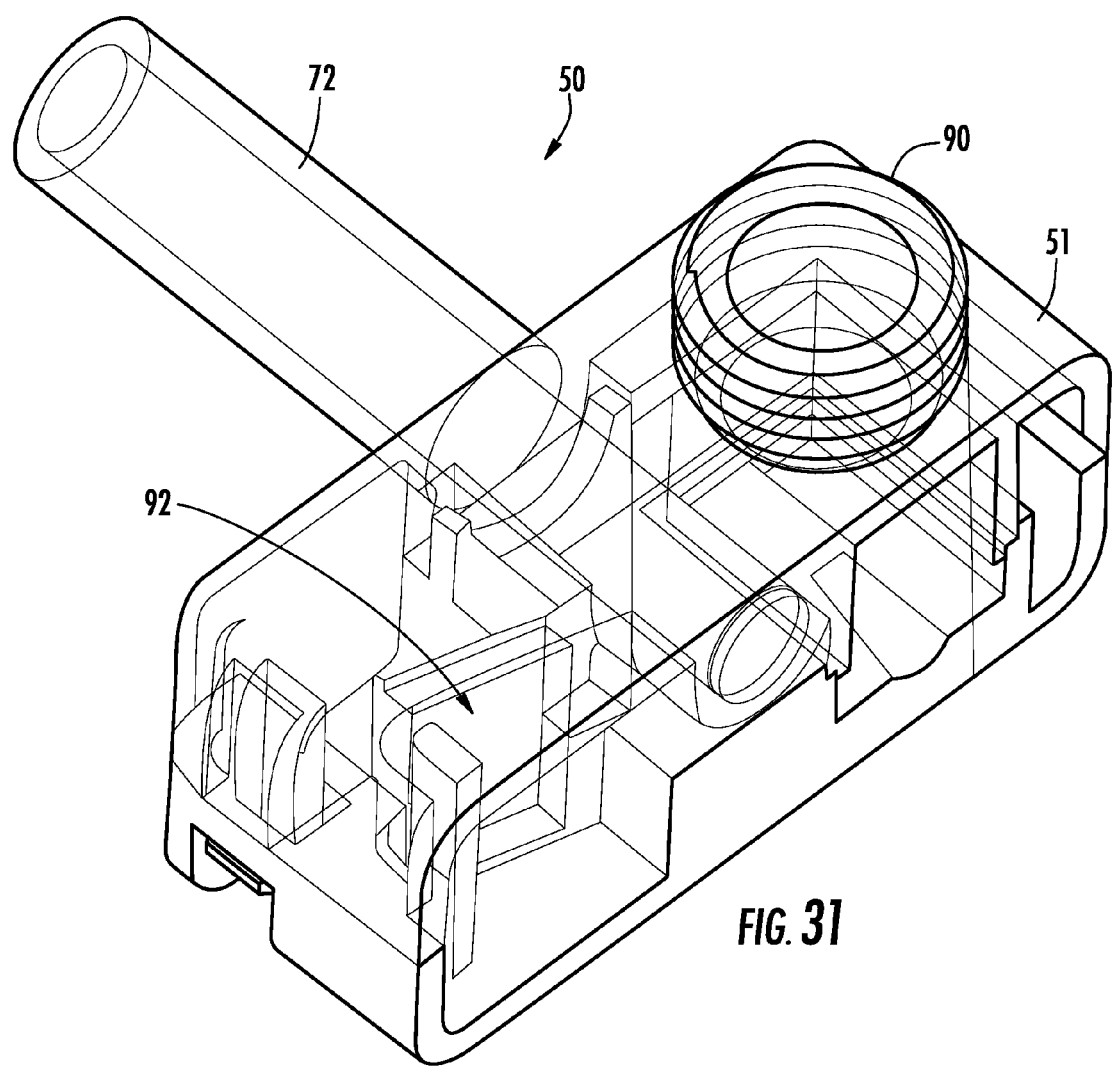

FIG. 31 is a fragmentary phantom view of a portion of the nebulizer body 51 showing the vent 92 formed in the nebulizer body and communicating with the air channel section 54 and medication reservoir 58 to vent the air channel section and medication reservoir to outside ambient air. Different vent configurations may be used besides the illustrated example. The communication between the sections in the nebulizer body could be by air channels and similar techniques.

Figure 32:
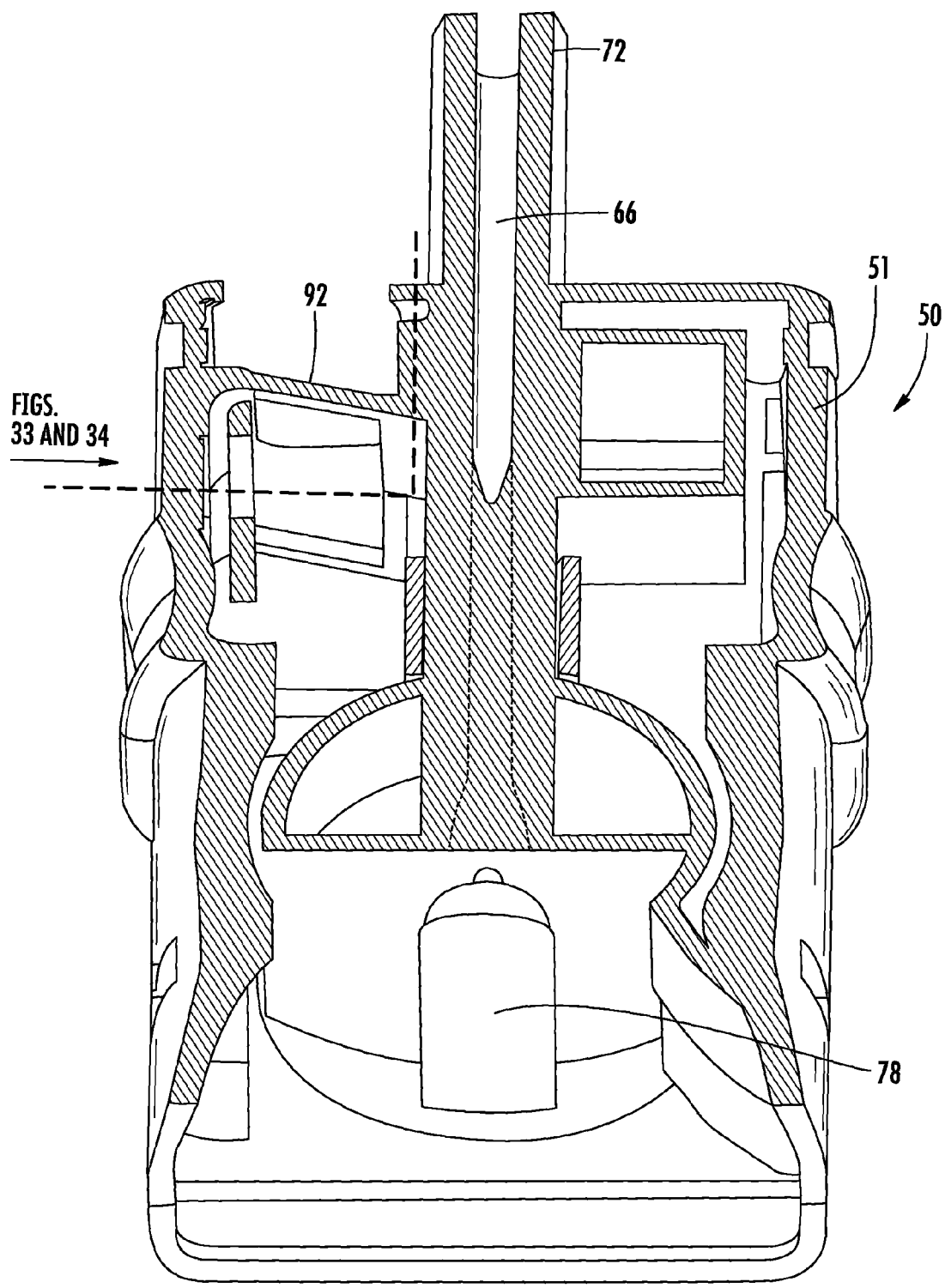
Figure 33:
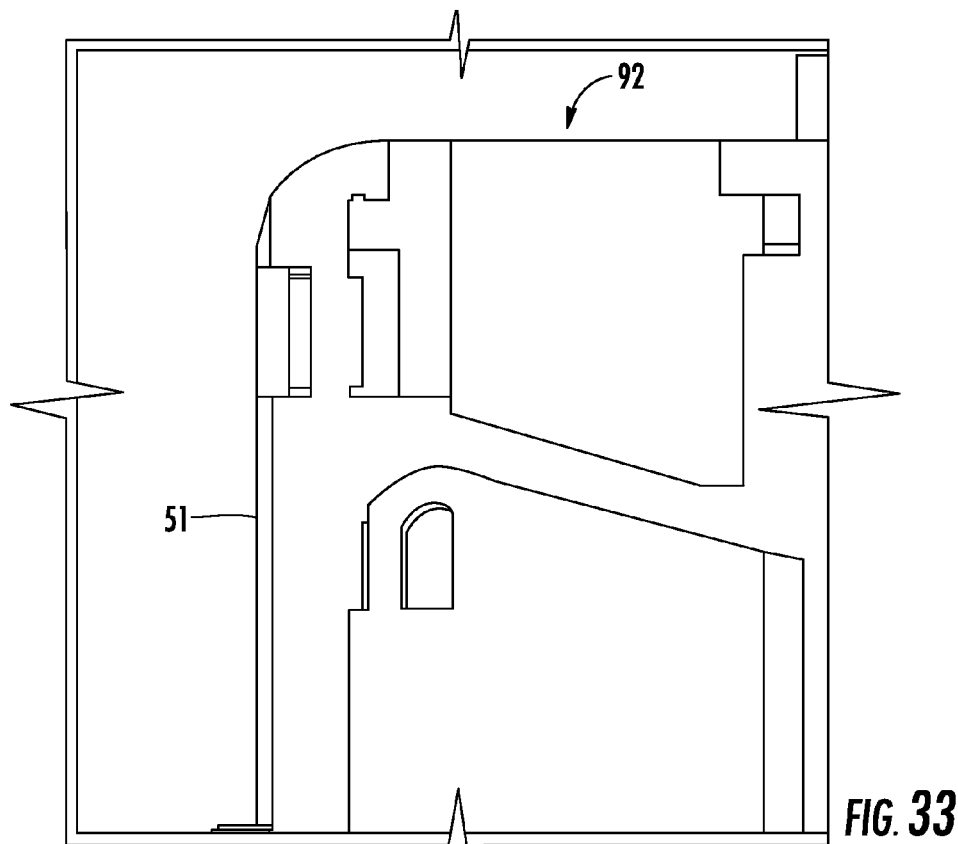
Figure 34:
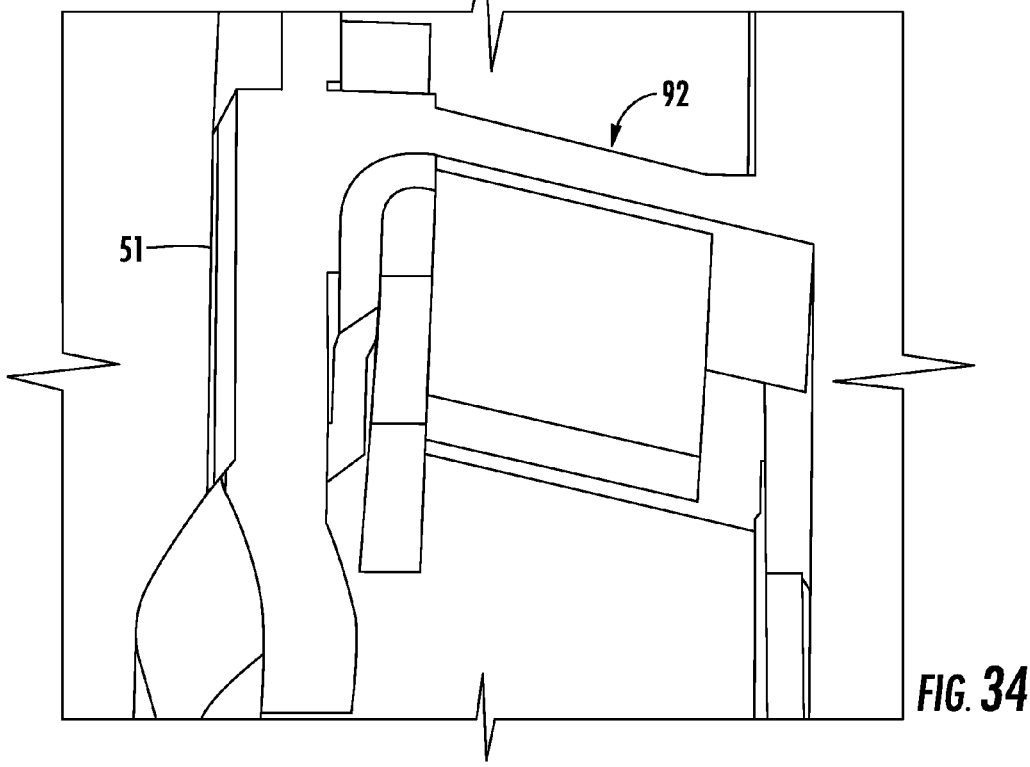
Figure 35:
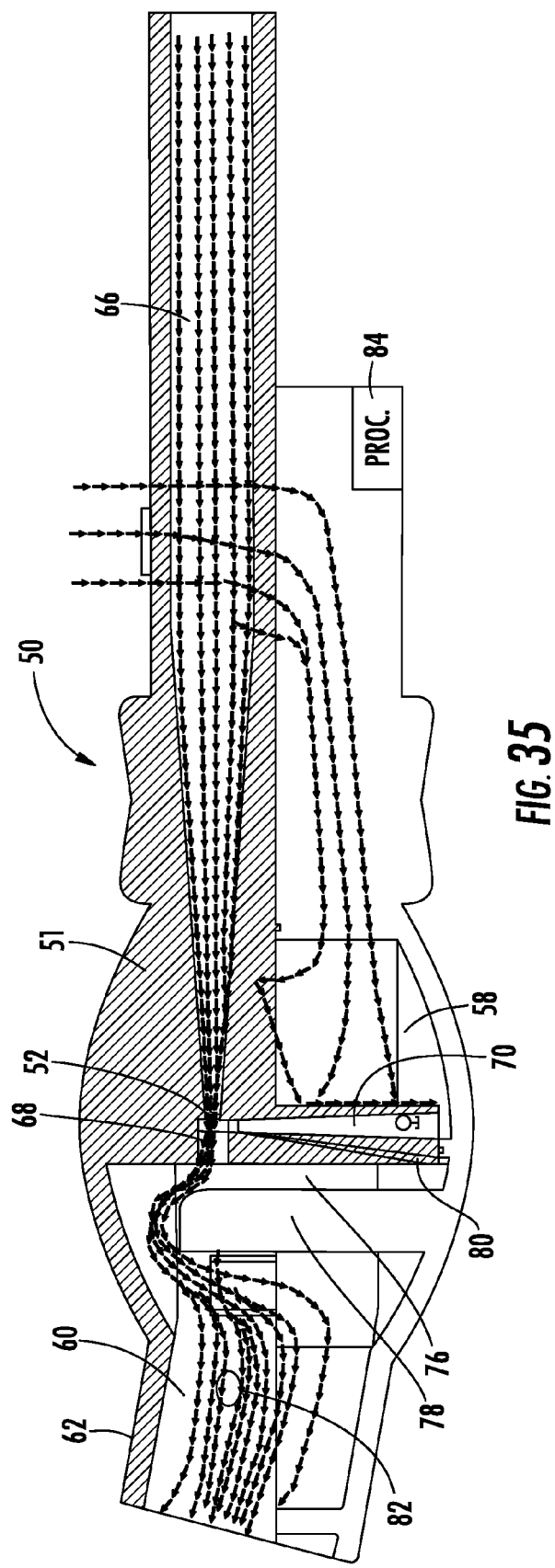

FIG. 32 is a more detailed partial cut-away plan view of the nebulizer body 51 showing the air line 66 extending through the air channel section 54 and including the venturi nozzle 56 and its end configured to form a low pressure mixing chamber 68 and the vent 92 formed in the body and communicating with the air channel section 54 and medication reservoir 58. The rainfall chamber 76 is illustrated such that the vent 92 is configured to vent the air channel section 54 and medication reservoir 58 to atmospheric pressure such that at standard temperature and pressure, a differential pressure results between the venturi nozzle 52 and medication reservoir 58. No medication is drawn upward through the primary suction line for nebulization and discharge through the nebulizer outlet until a negative inspiratory pressure is created from inhalation by a user. FIG. 32 also shows a diffuser or baffle 78 upon which the nebulized medication and air exiting the venturi nozzle and low pressure mixing chamber impacts to aid nebulization at the rainfall chamber. FIGS. 33 and 34 show greater details.

FIGS. 36-39 disclose a nebulizer in accordance with an embodiment that includes snap fit components and a nozzle assembly and suction line that are formed together and replaceable as one unit. For purposes of description, components that are common between this embodiment shown in FIGS. 36-39 and the previous embodiments shown in FIGS. 2-35 are given common reference numerals, but using the prime notation series.

Figure 36:
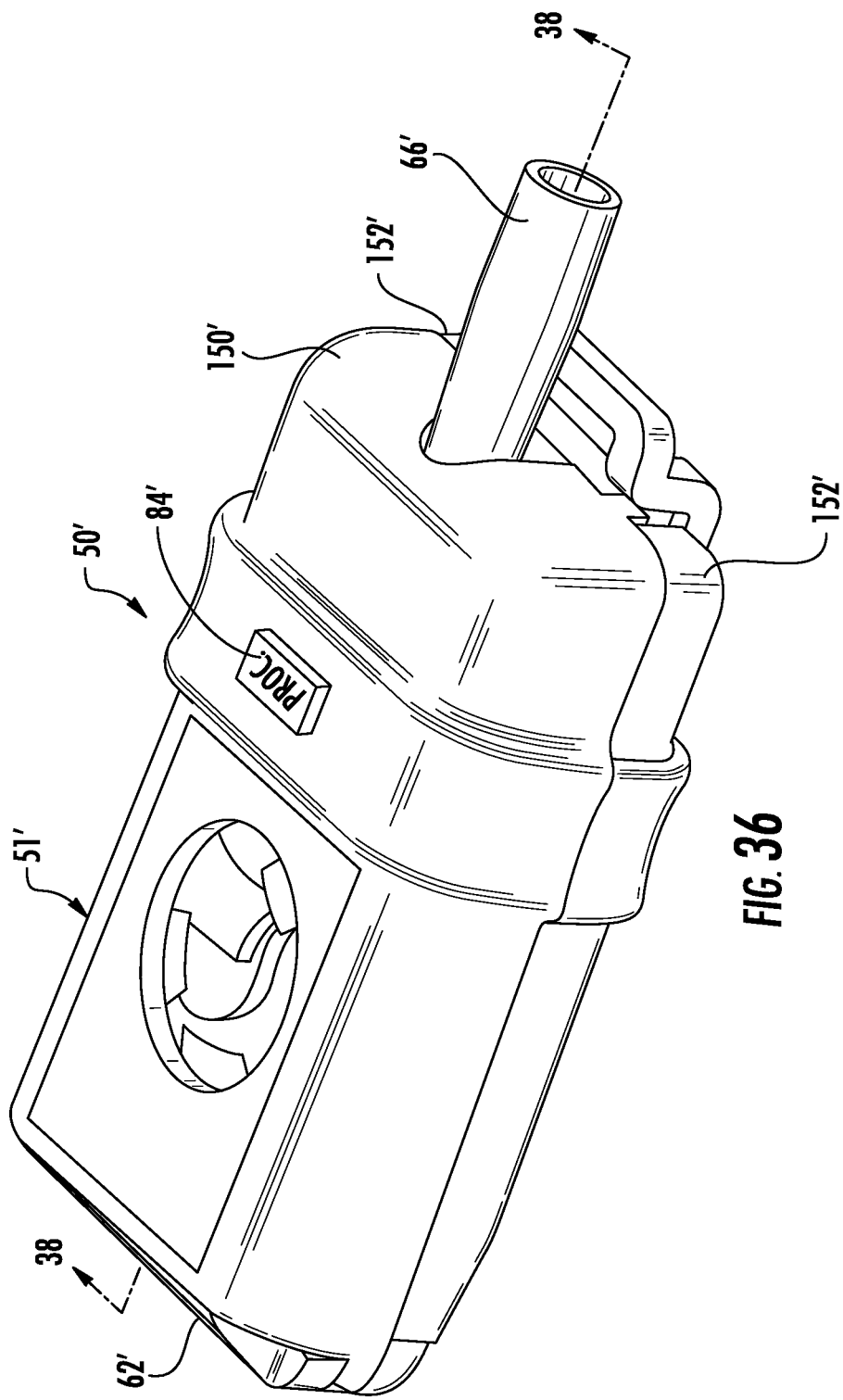
Figure 38:
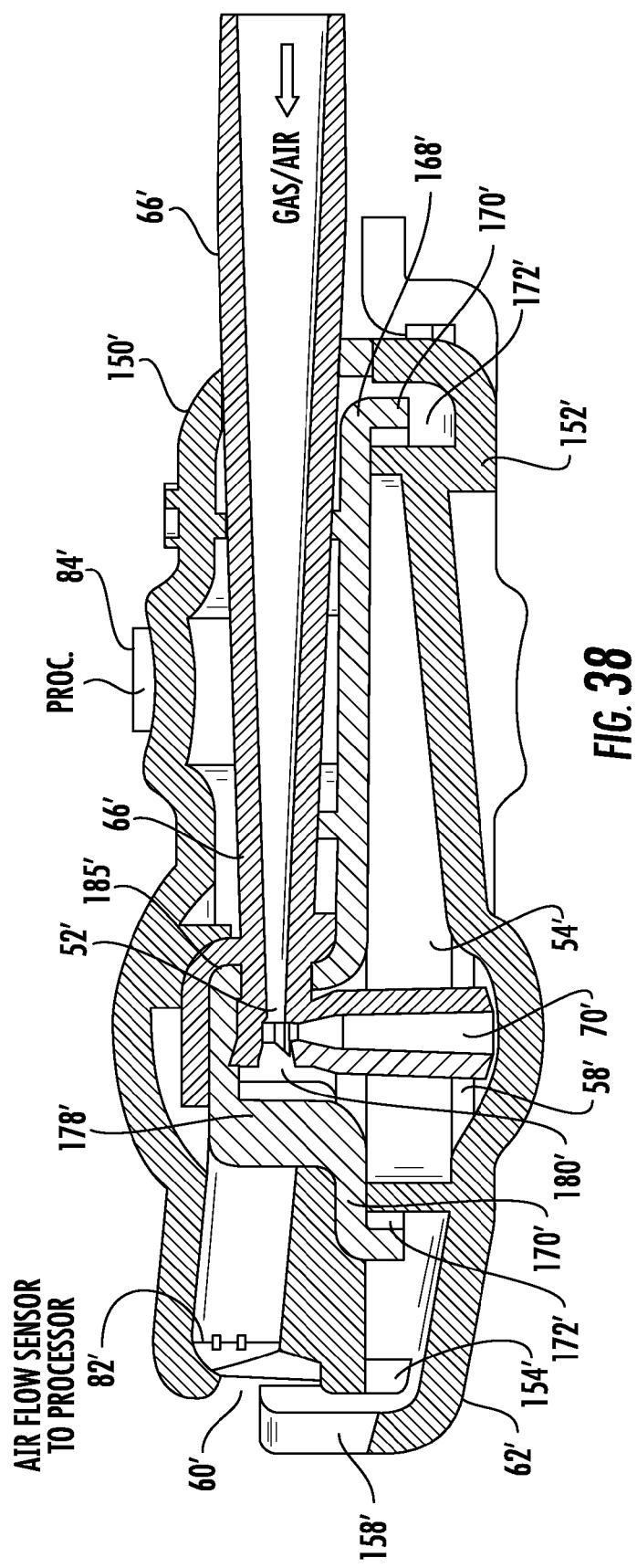

The nebulizer 50' includes a substantially rectangular nebulizer body 51' as illustrated in FIG. 36 and includes an air channel section 54' and a nebulizer outlet 60' as shown in FIG. 38 and configured as a mouthpiece portion 62' and configured to be received within an oral cavity of a patient. The nebulizer body 51' is formed from an upper portion 150' and a lower portion 152'. A medication reservoir 58' is formed in the lower portion 152' as shown in FIG. 38. These two components of the body forming the upper and lower portions 150', 152' may be injection molded plastic pieces that include respective upper and lower snap fit members 154', 156' that allow the two body members as upper and lower portions to snap fit together or be connected by other means. A reservoir cover 168' is supported by the lower portion 152' of the nebulizer body 51' and covers the medication reservoir 58' to form an enclosed medication reservoir in which medication is contained and held as best shown in FIG. 38. The lower body portion 152' and reservoir cover 168' each include respective snap fit members 170', 172' that allow the reservoir cover 168' to be snap fit to the lower body portion 152'.

Figure 37:
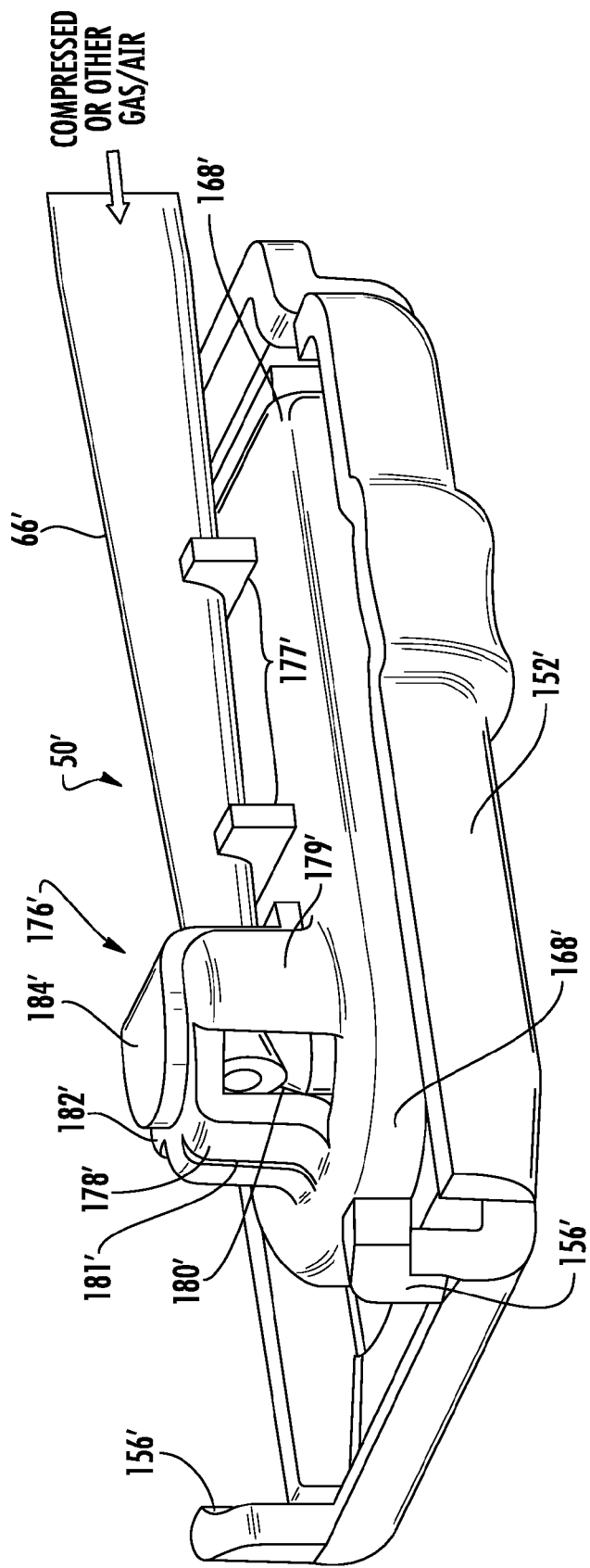

A nozzle assembly 176' is supported by the reservoir cover 168' and includes an air line 66' having an inlet at one end and extending through the air channel section 54' and having an outlet and a venturi nozzle 52' at the outlet and having a venturi outlet. The air line 66' is supported on two air line supports 177' mounted on the top of the reservoir cover 168' as shown in FIG. 37. The air line 66', venturi nozzle 52' and nebulizer outlet 60' are horizontally oriented when the nebulizer is in use and the venturi nozzle 52' is located within a patient's oral cavity when the nebulizer 50' is in use. It should be understood that the venturi nozzle can be configured to be proximal or close to the patient's oral cavity when in use.

Figure 39:
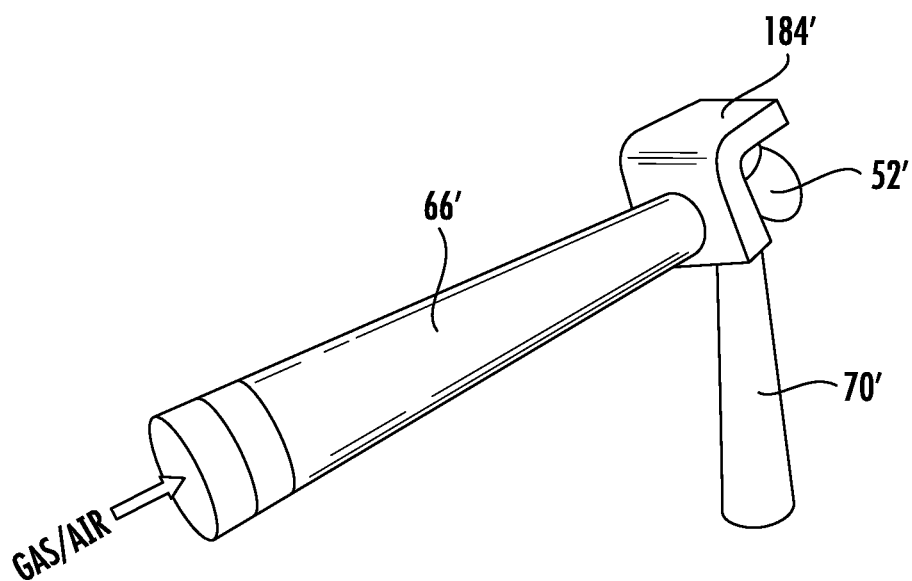

A suction line 70' extends from the medication reservoir 58' to the venturi outlet at the venturi nozzle 52' through which medication is drawn upward and mixed with air passing through the venturi nozzle and nebulized for discharge through the nebulizer outlet. The venturi nozzle 52' and suction line 70' are formed together as an integrated one-piece unit and replaceable as one unit as shown in FIG. 39. For example, the components could be injection molded as one unit to form an integrated unit that is readily replaceable. The nozzle assembly 176' formed by the air line 66', venturi nozzle 52' and suction line 70' may be formed from other techniques besides injection molded plastic components.

As best shown in FIG. 37, the reservoir cover 168' includes an upward extending diffuser 178' acting as a baffle and located proximal or in front of the venturi nozzle 52' to which the nebulized medication and air from the venturi nozzle impact to aid nebulization. The diffuser 178' is part of a cylindrical extension 179' extending upward from the reservoir cover 168' and covers the outlet and venturi nozzle 52' at the venturi outlet to form a low pressure mixing chamber 180' in which nebulized medication and air or other gas flowing through the air line are mixed and nebulized. The diffuser 178' includes a vertical slot opening 181' through which nebulized medication and gas pass. Based on the type of medications being used and other possible end uses for the nebulizer 50', the configuration of a slot opening 181' may be varied in length and width for different medications and different uses and types of nebulization. Because the reservoir cover 168' is easily replaceable, different reservoir covers may be used with different slot opening configurations and diffuser 178' configurations. The diffuser 178' includes a horizontal lock member 182' and the outlet of the air line 66' includes a top clip member 184' adjacent the venturi nozzle 52' and forms a locking slot 185' that receives the horizontal lock member 182' of the diffuser 178' to snap lock the nozzle assembly 176' and reservoir cover together. Other lock configurations may be used. The medication reservoir 58' is also located within a patient's oral cavity when the nebulizer 50' is in use.

All components may be formed from injection molded plastic in one non-limiting example and easily replaceable. It is possible to form the nebulizer 50' as illustrated as a one-time use, throw away nebulizer unit. A patient uses the nebulizer 52' one time and then discards it since it may be formed of injection molded plastic material parts that are readily mass produced in a non-limiting example. The medication is pre-stored in the nebulizer before use in an amount equivalent to one dosage in a non-limiting example. Other multiple dosages could be stored, however.

As illustrated, the air line 66' is tapered internally along much of its length to form a long venturi that terminates at a venturi outlet and forms an enlarged portion at the venturi outlet, which is configured to form a low pressure mixing chamber 180' as explained before. The air line 66' provides continuous pressure between the input and an outlet end of the air line, and in one example, no medication is drawn upward through the suction line for nebulization and discharge through the nebulizer outlet until a predetermined negative inspiratory pressure is created from inhalation by a user to begin air flow through the venturi nozzle 52'. At that time, medication is drawn upward through the suction line 70' and nebulized by air flowing through the venturi nozzle to be discharged through the nebulizer outlet 60'.

As illustrated, the suction line 66' is tapered similar to a venturi and intersects with the venturi nozzle 52' at its venturi outlet and at the low pressure the mixing chamber 180'. The configuration of the venturi within the air line and the configuration of the tapered suction line that are both formed similar to a venturi, and together with the pressure supplied through the air line, permits in one example nebulization to begin at a negative inspiratory pressure depending on the configuration used and air pressure of from about −3 cmH$_2$O to about −52 cmH$_2$O. The configuration can be similar to the configuration and tapers as shown in FIGS.

2-16 and the chart shown in FIG. 17 to provide actuation of the nebulizer under a specific and desired negative inspiratory pressure.

In the example shown in FIG. 38, an air flow sensor 82' is positioned within the air channel section 54' and at the nebulizer outlet 60' and configured to generate signals indicative of air flow generated by a patient's involuntary cough occurring at nebulization. A processor 84 is positioned in one example at the upper body portion and is configured to receive signals from the air flow sensor and evaluate the involuntary cough event as explained in further detail relative to other figures. The processor 84' is shown on the nebulizer, but the processor could be a separate device such as part of a handheld device. The air flow sensor could be located at other locations on the nebulizer and generate wireless signals to the example handheld device. Although the embodiments shown in FIGS. 36-39 are illustrative examples, it should be understood that different components and sizes may be used as understood to those skilled in the art.

Referring again to FIG. 1, the nebulizer described in that figure can advantageously be used for pediatric patients, such as young children and infants. FIGS. 18 and 19 show a nebulizer 100 in a pacifier configuration in which a rainfall chamber design as disclosed in the commonly assigned and incorporated by reference '306 patent includes an outer housing or body 102 that is configured similar to a pacifier or can be configured similar to a lollipop.

This nebulizer in one example could be designed similar to the nebulizer show in FIG. 1 and be activated by negative inspiratory pressure. In another example such as shown in FIG. 20 of the nebulizer, a pressure sensor 104 positioned at the nebulizer outlet senses negative inspiratory pressure. Upon sensing the negative inhibitory pressure, a signal is transferred back to a processor or controller or switch to operate the nebulizer. In a preferred example, however, the nebulizer shown in FIG. 1 is used, and there is no need to use a sensor with the associated processor. If the configuration of FIG. 1 is used, the negative inspiratory pressure begins the flow through the venturi nozzle and initiates medicine flow and nebulization.

The outer portion of the housing or body of the pacifier section of the nebulizer such as shown in FIGS. 19 and 20 includes a section that has a flavoring 106 and the position sensor 108 to indicate the infant's mouth position. This flavoring section is advantageous for sensor placement when an infant sucks on the pacifier or lollipop configured nebulizer. The infant or child will naturally suck on those areas of the pacifier that have the flavoring, indicative that the infant has positioned the pacifier nebulizer in its mouth in the proper position to allow nebulization to occur. When the infant or child has received the pacifier nebulizer in its the proper position as indicated by the sensor indicating this position, the lips or other portion of the infant's mouth covers the position sensor to indicate the proper mouth position. The position sensor sends a signal back to a controller, for example, to activate the nebulizer for operation. Operation in one example occurs only when the pressure sensor senses the negative inspiratory pressure. In the venturi nozzle design of FIG. 1, however, the negative inspiratory pressure itself begins the air flow through the venturi nozzle and medication to be draw upward.

As illustrated, if a nebulizer other than that shown in FIG. 1 is used, the flavoring on the outer portion of the pacifier allows an infant or child to position the pacifier nebulizer in its proper position in its mouth to allow nebulizer operation since the infant or child will naturally position the pacifier in a position where it can sense the flavor. A sugar-free flavoring can be used.

When this occurs, the infant will activate the position sensor that indicates the pacifier is in the proper position in the mouth for full nebulization and it effects. This activates the nebulizer for operation. The other pressure sensor within the intake would sense the negative inspiratory pressure, which then would send a signal back to a processor or controller or switch that is connected to any valves and/or medicine reservoirs and air lines to operate the nebulizer. Valves could open to allow operation in this example.

FIG. 18 shows a configuration in which the pacifier is received within an infant's mouth. The rainfall chamber portion is contained within the nebulizer or lollipop configured body or housing as a nebulizer suction member formed from a flexible material, as shown in FIGS. 19 and 20, while the other sections of the nebulizer in the '306, patent such as the medicine reservoir and any other type of medicine containers are contained in a separate housing or body that could be configured similar to a choo-choo train or other infant toy.

Also, the use of more than one medicine container with different medicines can allow simultaneous treatment or delivery of different medicines, actually creating a new drug based upon the combination. It is possible to change the combination depending on infant and child needs. Thus, with the configuration of FIG. 1 an infant can inhale creating the negative inspiratory force to activate the nebulizer, which becomes breath activated in this example. Other configurations can be used where inhalation can cause the nebulizer to open with different valves depending on the design.

FIG. 20 shows a nebulizer configuration such as described in the incorporated by reference '306 patent in which the nebulizer includes the rainfall chamber 110 and venturi 112 and medicine feed lines 114. Although not illustrated, the nebulizer could include a reservoir of medicine and would include at a distal end beyond a medicine port an air intake for an air line feeding the venturi inside the nebulization rainfall chamber. The medicine for the nebulizer can be filled directly into the reservoir or the nebulizer can come preloaded with the medicine. A venturi air line 116 could include a patient air intake port that allows air to be taken in at that port and fed through the body of the nebulizer. A cap could cover a medicine reservoir and be screwed on, snapped on, or otherwise locked on. The cap could be constructed so medicine could be injected into the reservoir through the cap.

FIG. 20 shows the side sectional view of the end of the pediatric nebulizer that engages the patient's mouth in accordance with one aspect of the invention, showing in more detail the rainfall chamber 110 and the venturi 112 and medicine feed lines 114. The venturi nozzle is approximately in the center of the illustration. Right beneath the venturi nozzle is a chamber which is fed by a venturi air line, indicated at the lower portion of the figure to the left of the venturi chamber. Parallel to the venturi air line and located somewhat displaced above the venturi air line is the medicine feed line 114. Medicine from the reservoir flows through the medicine feed line and through a relatively small opening just prior to the venturi in order to dispense medication into the air flow of the venturi. The venturi effect causes a reduction in pressure which causes the medicine to flow from the reservoir through the medicine feed line and into the venturi space where it is mixed with the air in traditional venturi fashion. The medicine that is nebulized by action of the venturi is expelled from the venturi port in an upward direction toward the diffuser 120. The diffuser in this case, is shown as textured. It is not necessary that it be textured but texturing may facilitate the break up of the droplets from the venturi into smaller sizes. As the droplets from the venturi bounce off the diffuser and break up, the sizes may not be totally uniform. The air pressure, the feed rate, the velocity with which droplets impact the diffuser and other well known factors can facilitate production of droplets of desired sizes. In fact, droplets can be generated utilizing this arrangement in sizes less than 0.1 microns. Nevertheless, larger droplets may coalesce as they diffuse throughout the rainfall chamber space. As droplets coalesce, they become larger and fall toward the bottom of the chamber where medication that is not utilized is gathered in a recycle sump 122. Medication found in the recycle sump, is recycled through the recycle venturi port 124 to the proximity with the venturi intake to be reutilized. In this manner, very little medication is wasted and the amount of medication delivered to the patient can be tightly controlled.

When the infant places his mouth on the patient inhale port, air from the infant inhale air path will circulate over the rainfall chamber and around the diffuser causing the extraction of droplets from the rainfall chamber for delivery to the patient. The patient inhale air path may go not only over the rainfall chamber, but around it to either side with the actual sizing depending upon the need for the amount of air flow to be delivered to the patient during administration of medication.

Dose reliability and reproducibility is enhanced by using unit dose medicine containers. High lung-deposition efficiency is vastly improved over the prior art because the venturi is located near or preferably inside the oral cavity. Very fine particles can be produced in accordance with the invention.

Figure 20A:
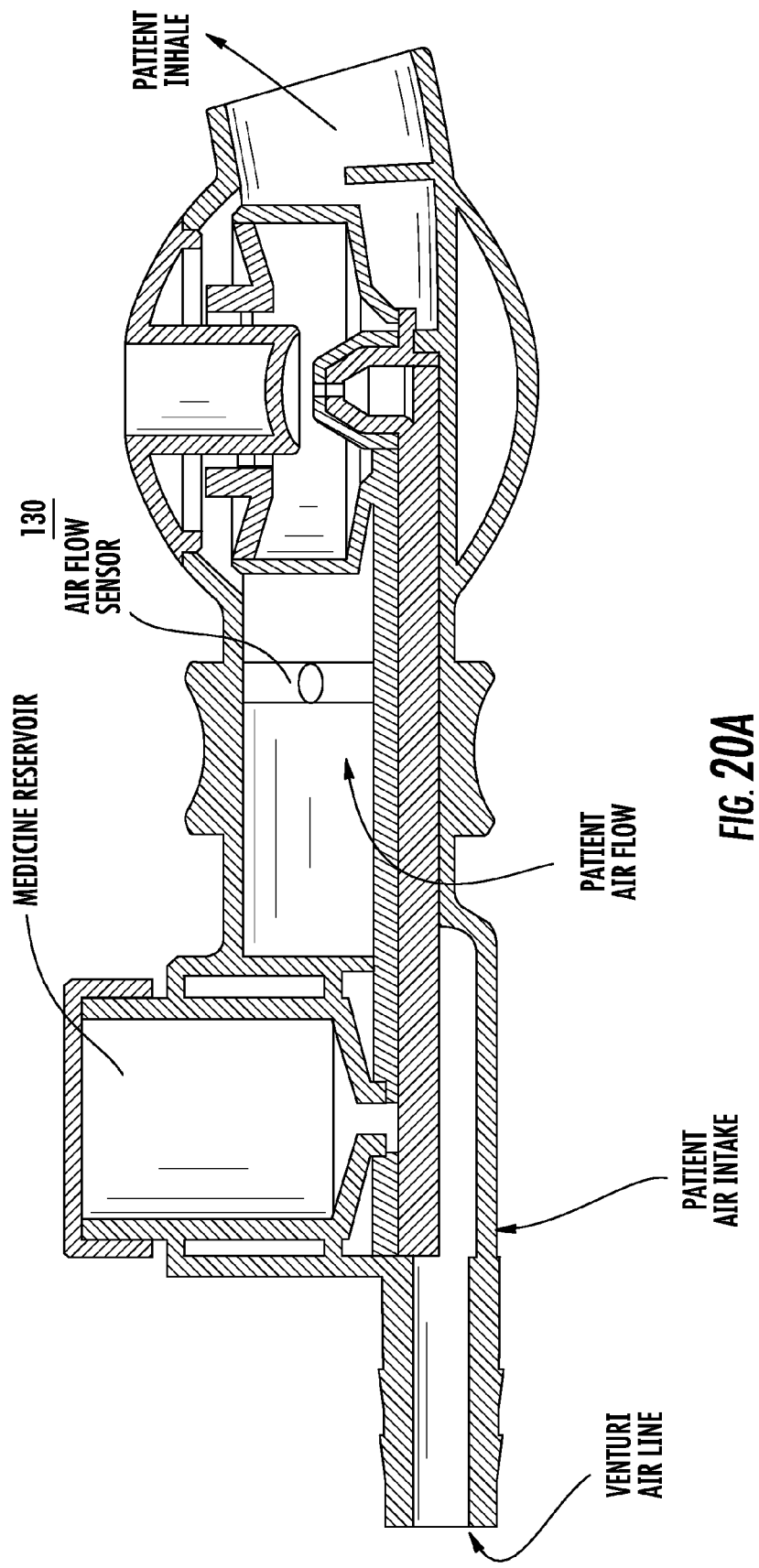
Figure 23:
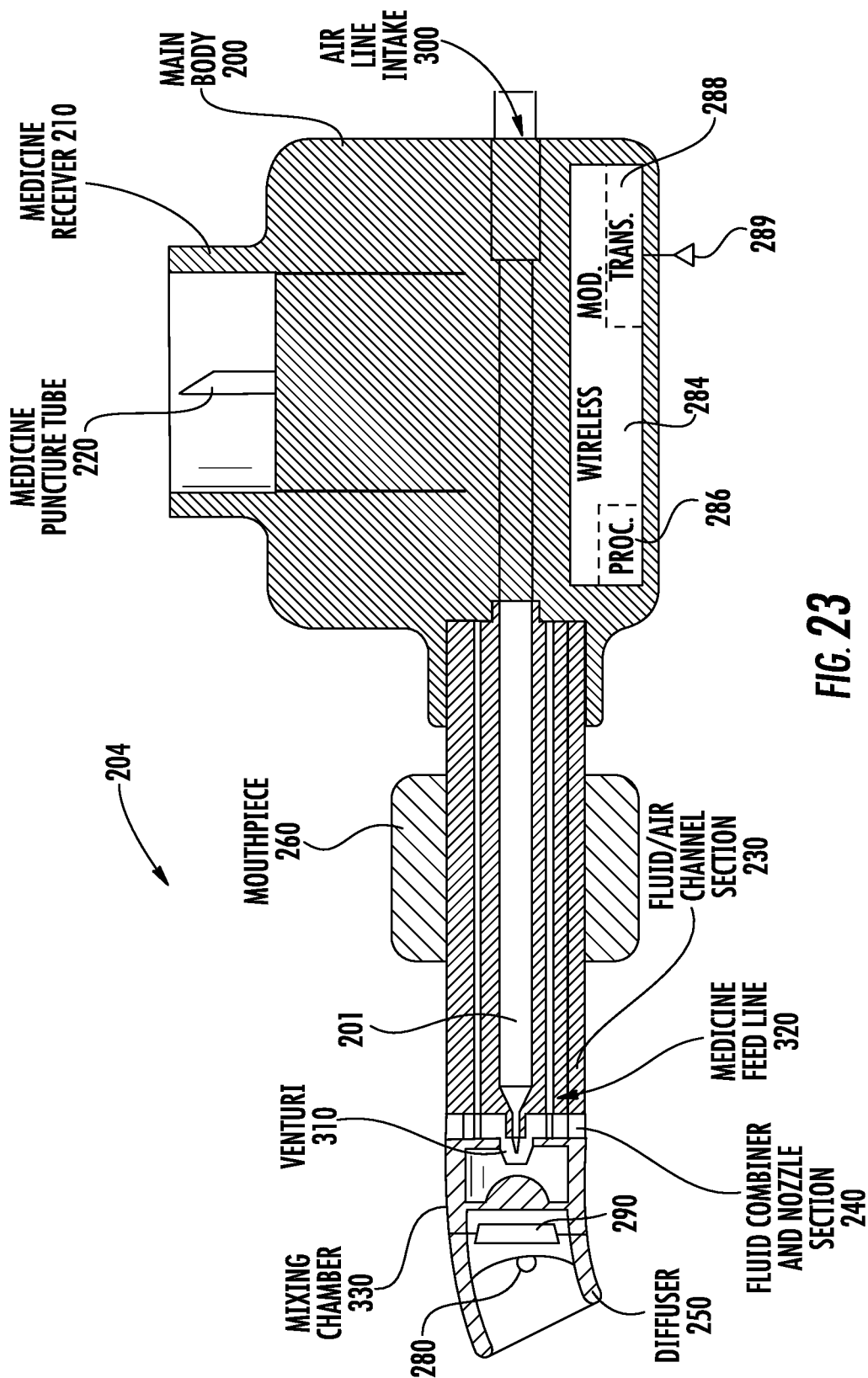

FIG. 20A shows a more complete view of the nebulizer as shown in FIG. 20, which also includes an air flow sensor 130 within the patient air flow channel. The pediatric nebulizer that incorporates this design could include air flow sensing ability to determine the capabilities of the infant as to one capacity and other details, but also give an indication of response, if necessary, to an involuntary reflex cough test. The air flow sensor could be connected by a wireless interface with a processor and transceiver such as shown in FIG. 23 and described below. Thus, functional components as shown relative to FIG. 23 can also be included in the nebulizer such as shown at FIG. 20A.

Figure 21:
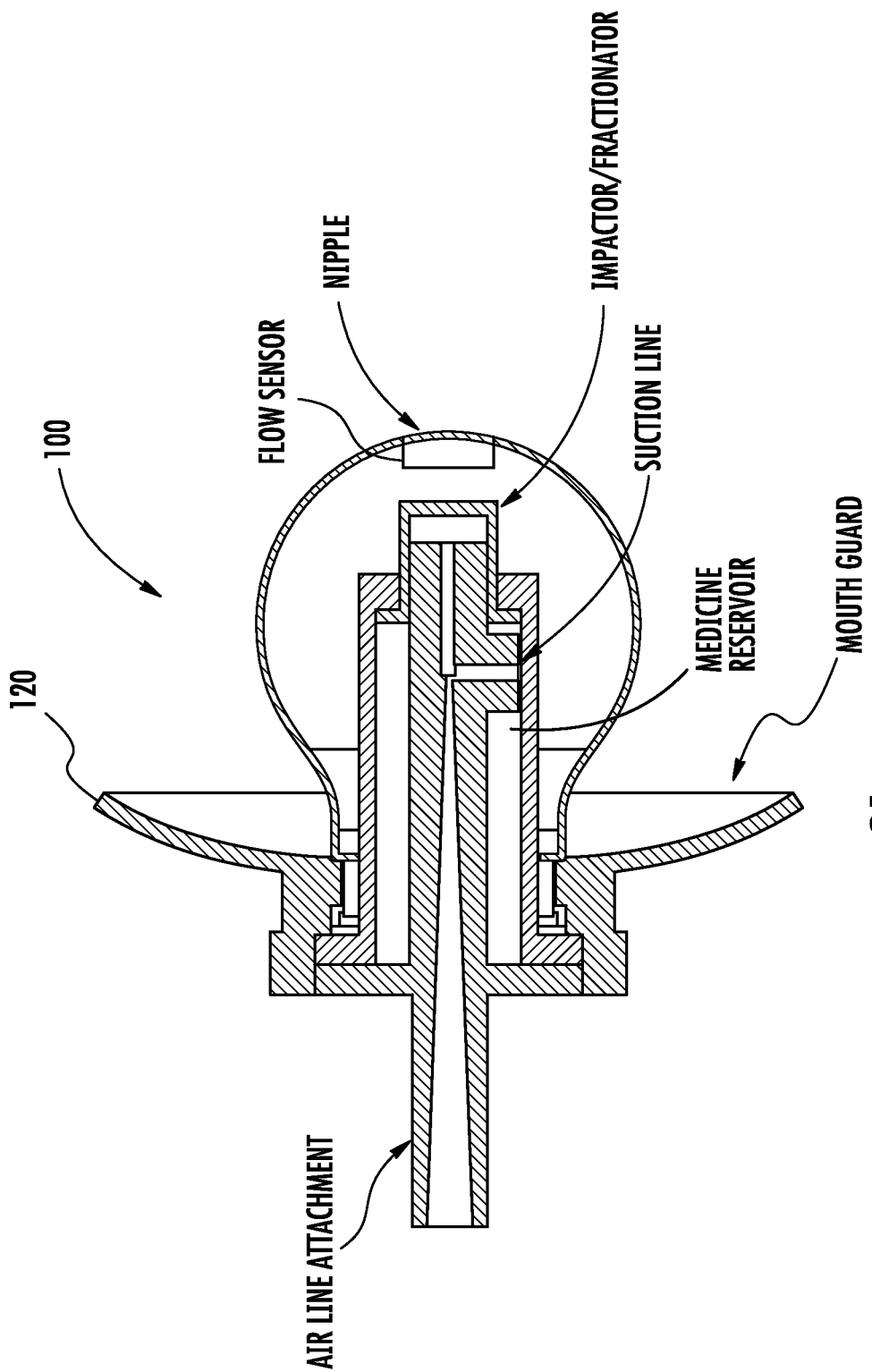
Figure 22:
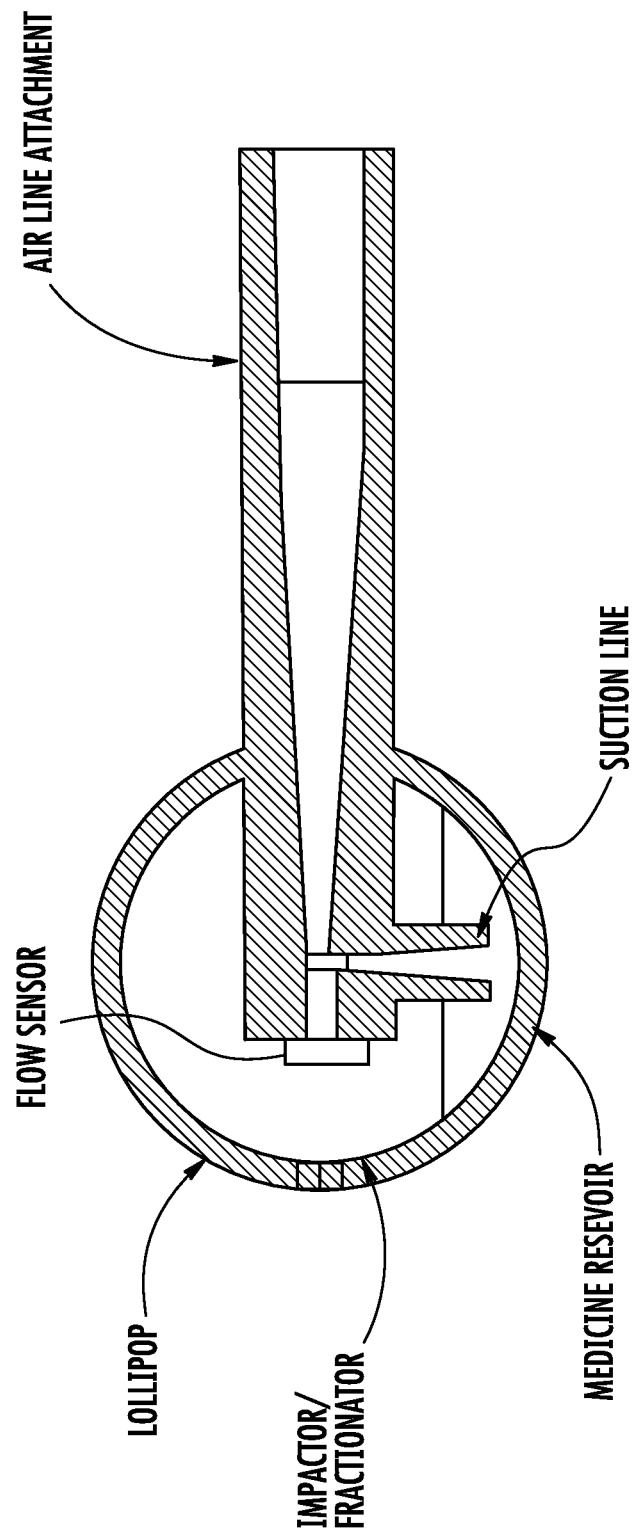

FIGS. 21 and 22 show other nebulizers configured for pediatric use. The venturi can be designed for breath activation as described before. Although the suction line is illustrated as a primary suction line, it should be understood that a secondary suction line can be used. FIG. 21 shows a nipple configuration and FIG. 22 shows a lollipop configuration.

FIG. 21 shows a different configuration for the nebulizer 100 that includes a mouth guard 110 and a suction line with the air line attachment. A different type of impactor/fractionator is disclosed and the nebulized medicine will impact against the impactor/fractionator and be discharged though the orifice at the nipple. The drops are spread throughout the open area defined by the pacifier housing. In another example, the nebulizer can operate in timed sequence to permit nebulization at specified times. A mouth guard is also illustrated.

FIG. 22 shows a modified lollipop configuration in which the air line attachment is shown in the primary suction line with the interior surface of the lollipop housing forming the impactor/fractionators to create greater fractionation. It is possible to insert a flow meter device such as a fan wheel that can operate to determine air flow for testing purposes. The air flow sensor could be connected to a small processor or communicate with a plug-in in which a handheld device such as shown in FIG. 23 can be plugged into the rear of the lollipop configured nebulizer.

Figure 15:
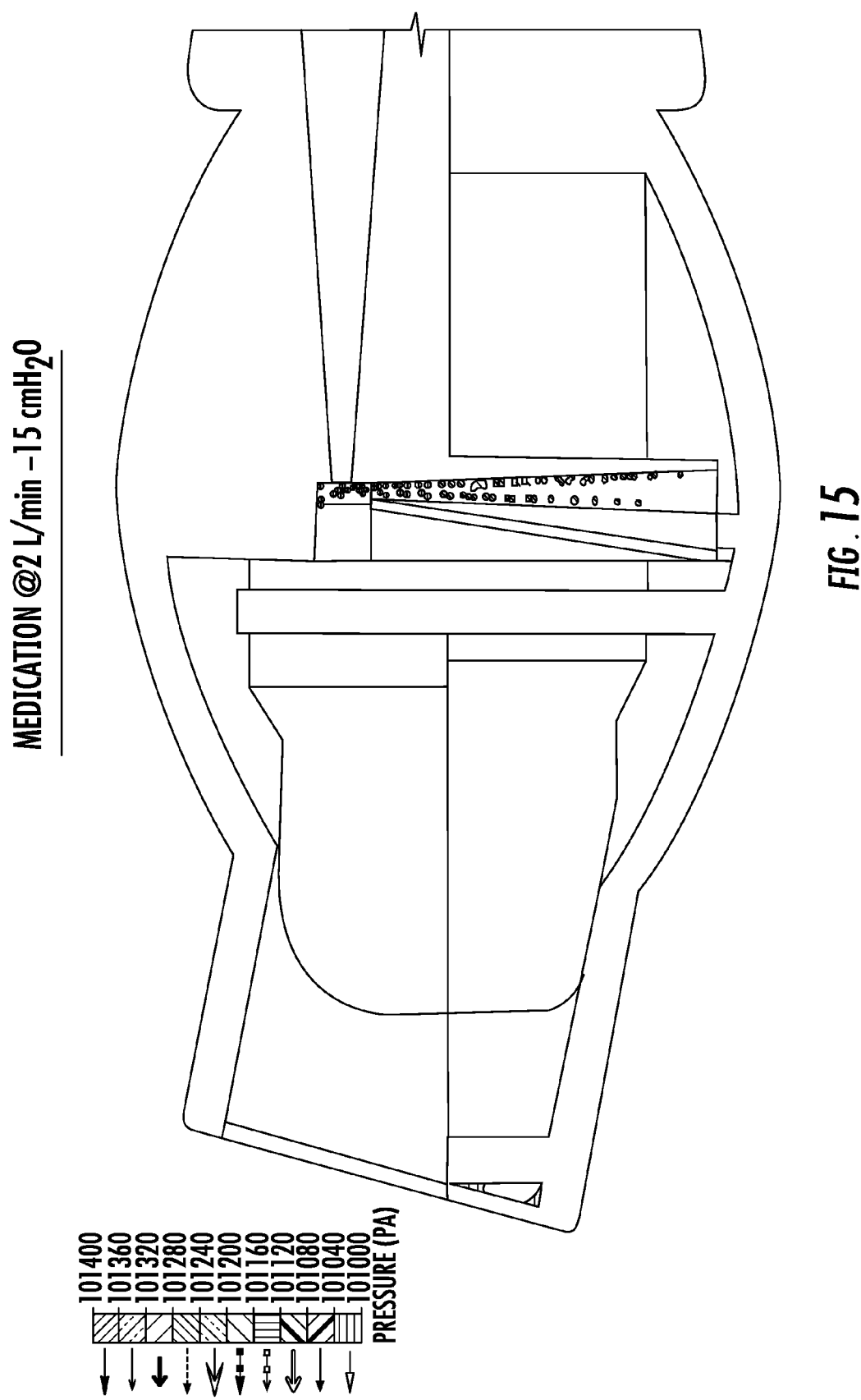
Figure 18:
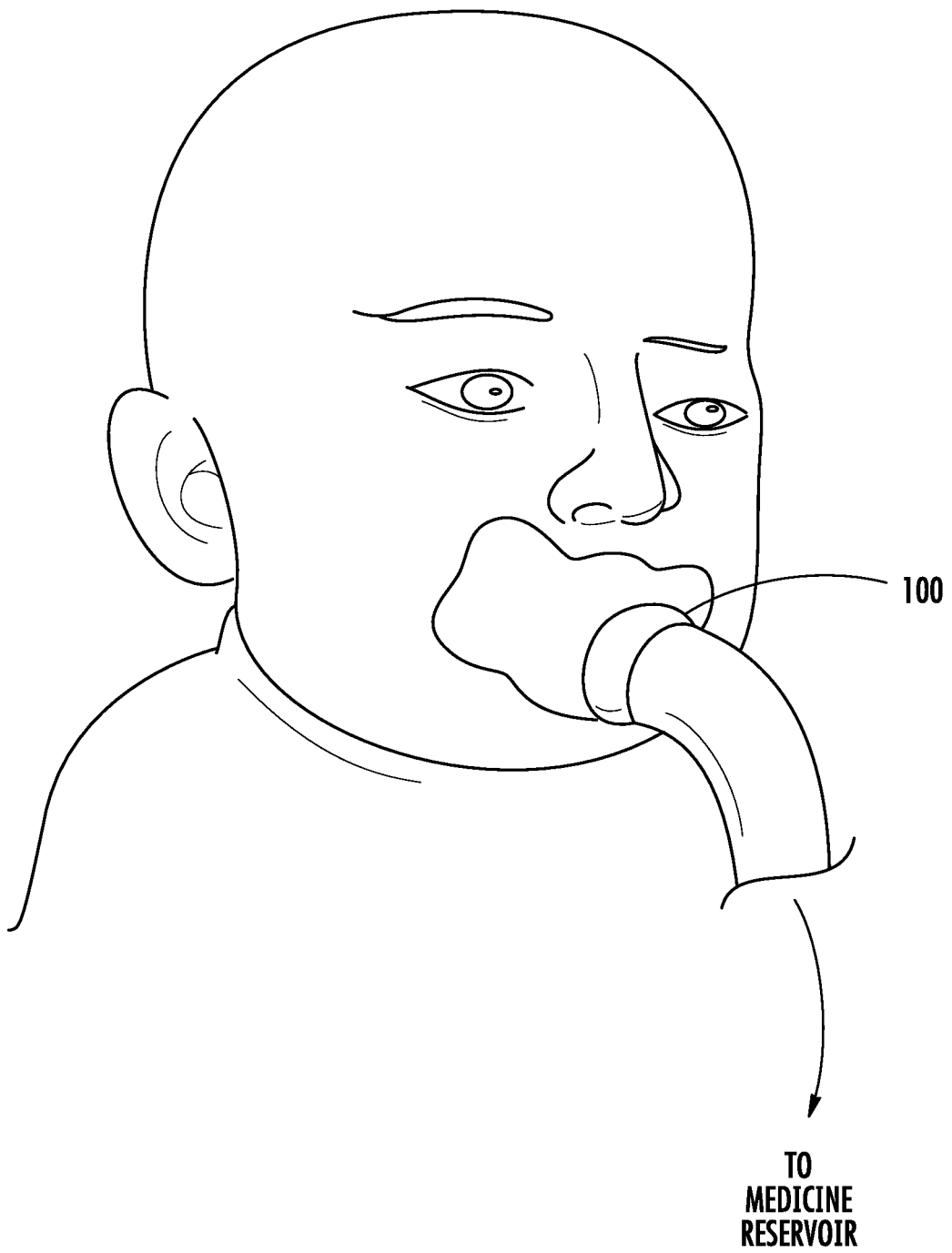
Figure 19:
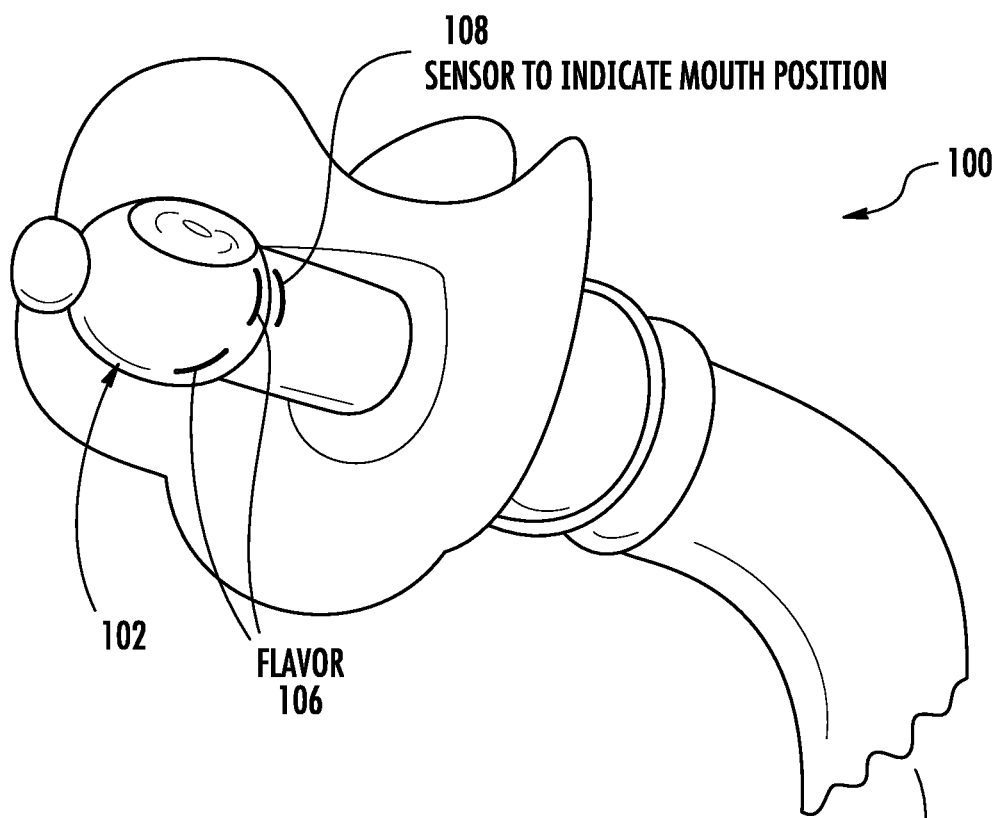

It should also be understood that new medicines can be designed by use of the venturi system. It is possible to preload the drug and form a new drug as a method. The nebulizer could operate as a trihaler or quadhaler. It can be placed in a solution in one container as a new drug and combined with a delivery system. It is possible to form the nebulizer and preload with the drug. Blow, fill and seal technology could be used to form a throw away nebulizer that is used one time. It could be filled and sealed at the manufacturing line. There could be a prefill port of any different shape or form and different types of medication delivery configurations. An example of different configurations for medicine supply as shown in FIGS. 15 and 16 of the '602 published patent application.

The use of a second nozzle can be advantageous because when condensation or agglomeration occurs, a drug will drop down through gravity feed and be redrawn to aid in mixing especially with preloaded medicine. Thus, the nebulizer shown in FIG. 1 can be formed as a sterile preloaded medicated nebulizer as a throw away device. Multiple new drugs can be developed through mixing with the nebulization and a venturi action.

It is also desirable to incorporate a flow meter function as described in the copending U.S. patent Ser. No. 12/724,785. This incorporated by reference patent application shows two types of flow meter designs that could operate as a clip-on device onto the various nebulizers disclosed and incorporated by referenced patents identified above. Other designs are in-line and are the preferred design with the nebulizer configurations shown in FIG. 1 or any pediatric nebulizers. In one desired design a spinning wheel is used instead of the designs show in the incorporated by reference application. In the embodiments described in the instant application, the nebulizer can be used to measure involuntary cough and measure the expiatory flow for the voluntary cough and what is the response. This could be beneficial with the pediatric nebulizer using the pediatric nebulizer for diagnoses. A spinning wheel for some type of spirometers could be incorporated into the nebulizers and used with the C5 stimulus, in which the involuntary cough occurs on the average of 4.8 times (average of 5 times) or 4.8 seconds on an average. The spinning wheel can calibrate a processor to measure peak flow and time over the inspiration and expiration and form a graph. It is possible to form the nebulizer where a button is pressed to activate the nebulizer, resulting in the involuntary cough. A flow sensor can be integrated with the nebulizer measures air flow at the time of the involuntary cough or at the time the button is hit. It is possible to plug the hand held device into the nebulizer as illustrated. The nebulizer device can perform the pulmonary function test (PFT) that is adequate for use with kids, such as using the lollipop nebulizer as shown in FIG. 21. It is possible to measure the velocity of the airflow and draw a graph of the inspiration and expiration over time. The system can draw loop interfaces to the processor or other PC and be compared relative to voluntary cough. During the C5 event it is possible to establish the normal versus the abnormal range.

Reference is made to the commonly assigned and incorporated by reference U.S. Patent Publication Nos. 2011/

0040157; 2011/0046653; and 2011/0040211, the disclosures which are hereby incorporated by reference in their entirety. It is possible to diagnose GERD and perform other analysis as explained in those incorporated by reference patent applications, including diagnosing stress urinary incontinence and problems with the lower esophageal sphincter.

The flow meter could be formed within an extension as a collar or molded into the nebulizer itself.

There is now described the nebulizers and flow meter sensor relative to FIGS. 23-27, similar to the description taken from the incorporated by reference Ser. No. 12/724,785 application.

FIG. 23 shows a nebulizer 204 that includes the main body 200 having an air channel section 201 that is formed by the air line intake 300 and fluid/air channel section 230 and related sections of the main body as illustrated and including a mixing chamber 330 and venturi 310 positioned to be placed within close proximity or within the patient's oral cavity in this non-limiting example and configured to receive medicine and air and mix the medicine and air within the mixing chamber and receive the air flow through the venturi and cause the medicine entering the mixing chamber to be atomized by the action of air flowing through the venturi. In this embodiment, an air flow sensor 280 is associated with the main body, and in this example at diffuser 250, and configured to measure the air flow created by the patient's one of at least inhaling and exhaling air. In this example, the air flow sensor 280 is positioned within the air channel section 330 and as illustrated at the exit side of the mixing chamber within the diffuser such that air flow is measured when the patient is at least one of inhaling and exhaling air through the diffuser in this example.

Figure 27:
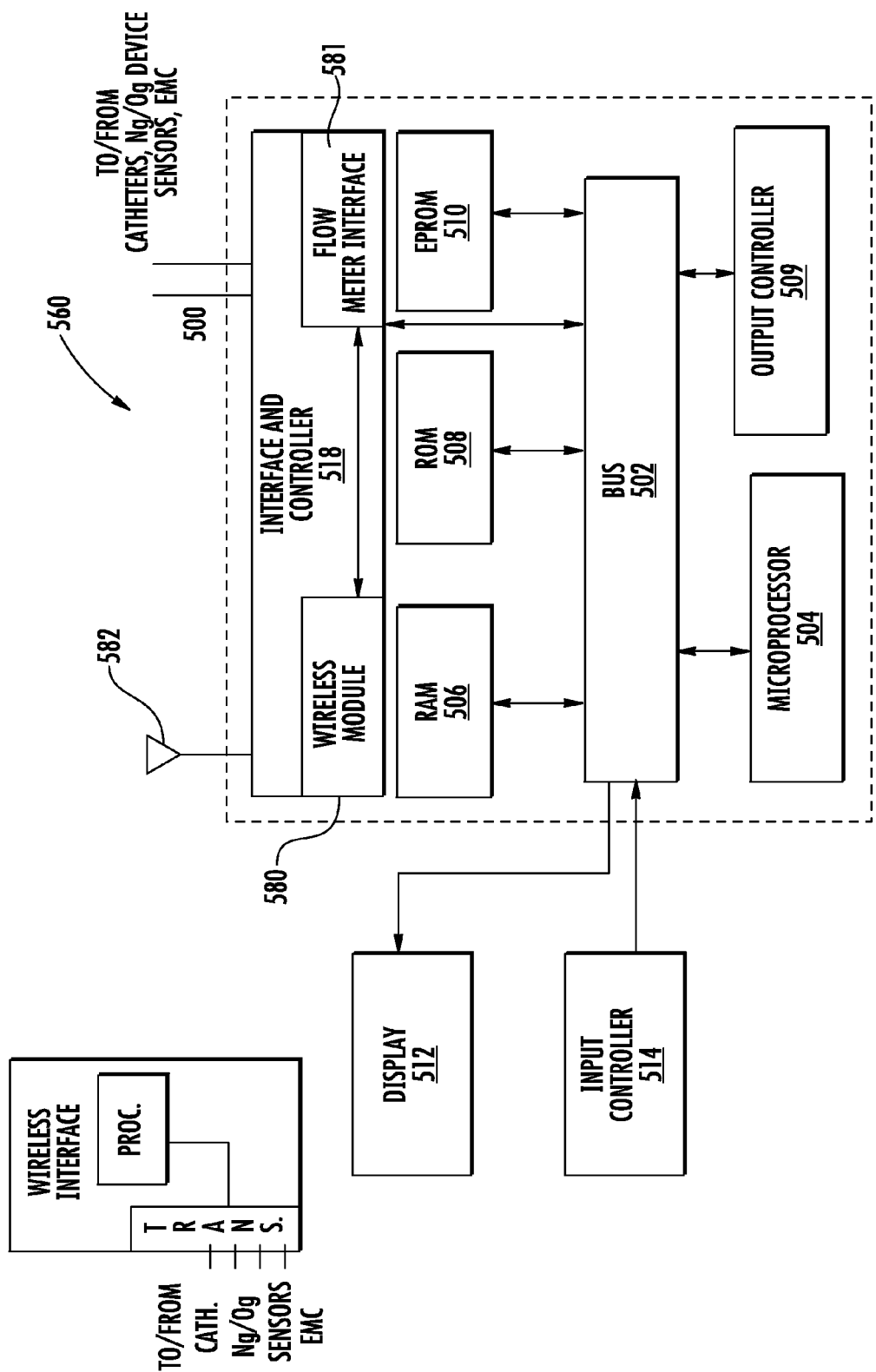

The air flow sensor 280 senses and measures the air flow and sends a signal through communications signal lines 282 (shown in FIG. 24) back to a wireless module 284 positioned in the main body 200, The wireless module 284 in this example includes a processor 286 and wireless transceiver 288 such that the signals from the air flow sensor 280 are processed and in this example wirelessly transmitted through an antenna 289 (which could be a conformal antenna positioned on the main body 200) to a handheld processing device 560 such as shown in FIG. 26 and with its processing capability illustrated in block diagram at FIG. 27. The outlet at the diffuser on the exit side of the mixing chamber in this example chamber includes an air flow metering valve 290 positioned within the air flow channel and configured to adjust the resistance to air flow to a predetermined level for respiratory exercise training and incentive spirometry use. In this example, the air flow metering valve 290 is formed as a baffle or similar mechanism that can be adjusted to vary the amount of air flow resistance. The adjustment can be indexed such that any adjustment and air flow resistance can be predetermined, for example, using a manual adjustment or servo drive (actuator) for adjusting the valve. The air flow sensor 280 in this non-limiting example is shown as paddle wheel type sensor or could be a flap with actuators, such as MEMS actuator, which inter-operate with a processor to determine air flow adjacent the air flow metering valve 290. The air flow metering valve 290 in an example includes a small drive mechanism such as an actuator attached thereto, allowing adjustments to be made based upon a signal such as from the processor 286 and feedback signal from the air flow sensor to adjust and vary the amount of resistance to air flow for respiratory exercise training and incentive spirometry use.

The valve 290 can also in one example be manually adjusted by a patient and include settings to aid in adjustment as noted before.

In a non-limiting example, the handheld processing device 560 is configured to process the measured air flow over time to determine a respiratory function of the patient. This device 560 is also configured in another example to process measured air flow over time to determine a neurological deficiency in a patient based on air flow measurements derived from an involuntary reflex cough. For example, the analysis of the voluntary cough and involuntary reflex cough test is disclosed in commonly assigned and U.S. Patent Publication Nos. 2007/0135736; 2010/0137736; 2007/0255090; 2010/0137737; 2011/0040157; 2011/0046653; and 2011/0040211, the disclosures which are hereby incorporated by reference in their entirety. These commonly assigned published patent applications set forth details of the voluntary cough testing and involuntary reflex cough testing in which the nebulizer as described in the instant application can be used to aid in the type of testing as set forth in those incorporated by reference applications. Such testing is advantageously used to diagnose stress urinary incontinence or problems in the lower-esophageal sphincter as a non-limiting example.

FIG. 25 shows a modified nebulizer such as the type disclosed in commonly assigned U.S. Publication No. 2007/0137648, the disclosure which is hereby incorporated by reference in its entirety. This application shows air curtain inlets created by air curtain conduits 404 that are used to supply a curtain of air above and below the nebulized medicine and air passing through medication conduit 400 and to enhance penetration of nebulized medicine into the airway of the patient. The air flow sensor 280 as a paddle wheel type device is positioned at the exit end of the nebulizer 204 as illustrated and in this example includes the air flow metering valve 290 as illustrated and incorporates a manual or automatic adjustment mechanism such as an actuator as may be needed.

It should be understood that different types of air flow sensors 280 can be used besides the illustrated spinning wheel configuration. As disclosed in the incorporated by reference 2010/0204602, it is possible to design the air flow sensor 280 as a mass air flow sensor that converts the amount of air drawn or expelled into and out of the nebulizer into a voltage signal. Different types of mass air flow sensors could be used such as a vane air flow meter, including using any necessary MEMS technology or using a Karmen vortex or a semiconductor based MAF sensor. It is possible to use a hot wire MAF sensor such as a thermistor, platinum hot wire or other electronic control circuit to measure temperature of incoming air, which is maintained at a constant temperature in relation to the thermistor by an electronic control circuit. As heat is lost, electronic control circuitry can compensate by sending more current through the wire. This is only one example. The wire typically will be kept cool enough such that the temperature does not impact a patient. The hot wire can be placed further into the diffuser and/or main body within the air channel. It is also possible to use an Intake Air Temperature (IAT) sensor.

Another possible air flow sensor is a vane air flow meter that includes basic measuring and compensation plates and other potentiometer circuits. In another example, the air flow sensor uses a "cold wire" system where an inductance of a tiny sensor changes with the air mass flow over that sensor as part of an oscillator circuit whose oscillation frequency changes with sensor inductance. In another example, the flow sensor is an electronic membrane placed in the air stream that has a thin film temperature sensor such as printed on an upstream side and another on the downstream side and a heater in the center of the membrane that maintains a constant temperature similar to the hot-wire. Any air flow causes the membrane to cool differently at the upstream side from the downstream side and this difference indicates the mass air flow. MEMS technology can be used such as MEMS sensors. In this type of sensor, a MEMS sensor has a silicon structure and sometimes combined with analog amplification on a microchip. It includes an analog-to-digital converter on a chip in another example and can be fused with analog amplification and the analog-to-digital converters and digital intelligence for linearization and temperature compensation. The MEMS testing in one example is used for an actuator to control the valve 290.

It should be understood that although the air flow sensor is shown located at the discharge end of the nebulizer at the diffuser on the exit side of the mixing chamber, other locations and positions for the air flow sensor or number of air flow sensor members are possible as well as the valve 290.

Figure 24:
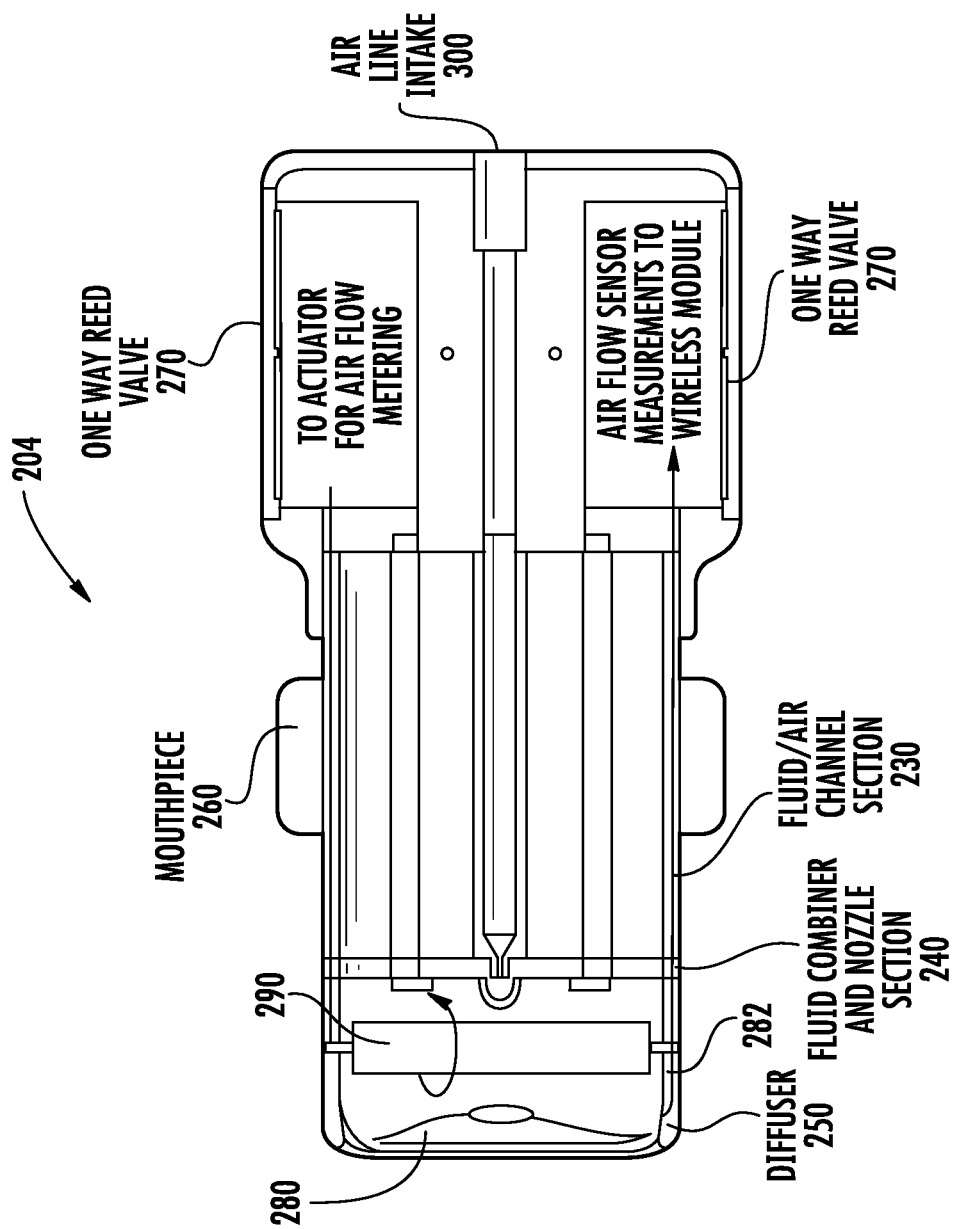
Figure 25:
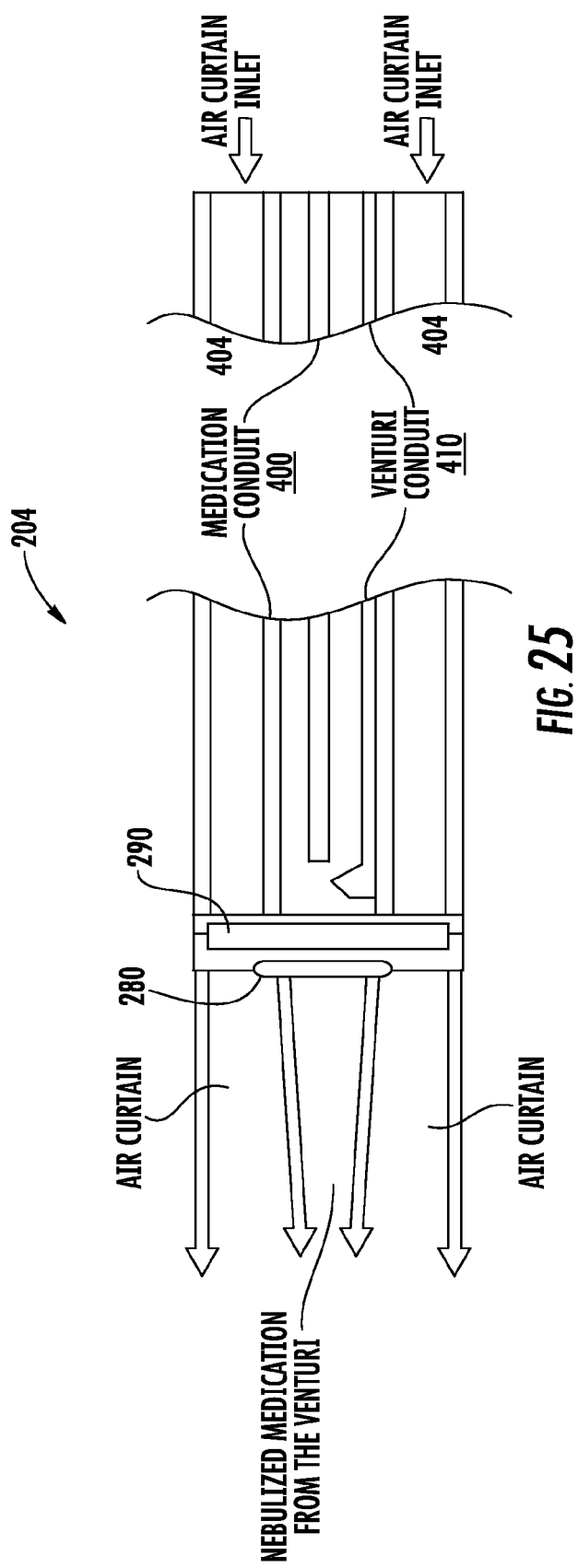

It should also be understood that the nebulizer using the waterfall chamber as described in incorporated by reference patent publications also in an example has the flow meter function as described and includes the air flow sensor and wireless module as illustrated in FIGS. 23 and 24 and can be positioned in different locations within that device. The air flow sensor can be located at the discharge end on the exit side of the rainfall chamber or other locations in which the air flow can be measured. The valve 290 is also included in another embodiment and includes an actuator in yet another embodiment.

Air flow can be measured in pounds per second (lbs./sec.) and operate for pulmonary function testing calculations and incentive spirometry use. The nebulizer in this example can work as a differential pressure transducer and connect to a pneumotachygraph (or have a self-contained chip with such function) to record the velocity of respired air. It is possible to process associated data as air flow, air pressure, air resistance, and other Pulmonary Function Testing (PFT) results for respired air and data results from voluntary cough (VC) and involuntary reflex cough testing (iRCT). The pulmonary function testing can use spirometry to assess the integrated mechanical function of the lungs, chest wall and respiratory muscles and measure the total volume of air exhaled from a full lung for total lung capacity and empty lungs as residual volume. The Forced Vital Capacity (FVC) can be measured and a forceful exhalation ($FEV_1$) can be repeated. Spirometry can be used to establish baseline lung function, evaluate dyspnia, detect pulmonary disease and monitor effects of therapies used to treat respiratory disease and evaluate respiratory impairment and evaluate the operative risk and perform surveillance for occupational-related lung disease. Pulmonary function testing can be used to determine how much air volume is moved in and out of the lungs and how fast the air in the lungs is moved in and out. This testing can determine the stiffness of the lungs and chest wall for compliance. The flow meter function using the air flow sensor and the associated air flow metering valve together with any processing capability can be used for Inspiratory Muscle Training (IMT) to provide consistent and specific pressures for inspiratory muscle strength and endurance training. The adjustable valve or other adjustable mechanism can ensure consistent resistance and be adjustable such as manually or through microprocessor control for specific pressure settings. It is possible to use the same nebulizer for exercise treatments and therapy and spirometer treatments. The handheld processing device 560 captures the data and can be marketed together with the nebulizer and any necessary catheters for reflex cough testing as a kit. The pneumotachygraph function can be placed in a single chip within the nebulizer or as a separate flow meter device explained below relative to FIG. 25 and connected to the nebulizer. Data containing air flow measurement results can be wirelessly transmitted to the handheld processing device or other processor.

The nebulizer also operates in a non-limiting example as a differential pressure transducer. If the nebulizer is to measure voluntary cough or the involuntary reflex cough, an air channel can be connected to the medicine and gas canister (for tartaric acid in one example) and measure the voluntary cough and involuntary reflex cough for in-phase duration from the time from onset to peak and expulsive phase and in-phase volume such as the duration of the glottic closure as explained in greater detail below. It is also possible to measure in-phase peak flow and the expulsive phase peak flow using such device.

A patient (or clinician or physician) can perform a medical treatment with the nebulizer. It is also possible to operate the flow meter after nebulization to determine if the patient has improved due to the use and administration of the drug such as the tartaric acid. It is possible to measure and graph results through an air flow sensor as part of the flow meter device and transfer data to the handheld device (or other processing device) and measure flow and pressure over time.

FIG. 26 is an illustration of an exemplary handheld processing device 560. More particularly, it should be understood that this handheld processing device 560 can be used by a nurse practitioner or doctor and receive input as wireless signals for flow meter testing as described above. Also, this handheld processing device 560 can incorporate the circuit and functions as disclosed in the various copending and commonly assigned applications identified above. Catheters and other inputs can be connected to this handheld processing device 560 as explained in the above-identified and incorporated by reference patent applications.

FIG. 27 is a block diagram that illustrates a computer system 500 for the handheld processing device 560. Computer system 500 includes a bus 502 or other communication mechanism for communicating information, and a processor 504 coupled with bus 502 for processing information. Computer system 500 also includes a main memory 506, such as a random access memory (RAM) or other dynamic storage device, coupled to bus 502 for storing information and instructions to be executed by processor 504. Main memory 506 also may be used for storing temporary variables or other intermediate information during execution of instructions to be executed by processor 504. Computer system 500 further includes a read only memory (ROM) 508 or other static storage device coupled to bus 502 for storing static information and instructions for processor 504.

Computer system 500 may be coupled via bus 502 to a display 512, such as a LCD, or TFT matrix, for displaying information to a computer user. An input device 514, for example buttons and/or keyboard, is coupled to bus 502 for communicating information and command selections to processor 504. Another type of user input device is cursor control, such as a mouse, a trackball, or cursor direction keys for communicating direction information and command selections to processor 504 and for controlling cursor movement on display 512. This input device typically has two degrees of freedom in two axes, a first axis (e.g., x) and a second axis (e.g., y), that allows the device to specify positions in a plane.

Computer system 500 operates in response to processor 504 executing one or more sequences of instruction. Execution of the sequences of instructions causes processor 504 to perform the process steps described herein. In alternative embodiments, hard-wired circuitry may be used in place of or in combination with software instructions to implement the invention. Thus, embodiments of the invention are not limited to any specific combination of hardware circuitry and software.

The term "computer-readable medium" as used herein refers to any medium that participates in providing instructions to processor 504 for execution. Such a medium may take many forms, including but not limited to, non-volatile media, volatile media, and transmission media. Non-volatile media includes, for example, optical or magnetic disks. Volatile media includes dynamic memory, such as main memory 506. Transmission media includes coaxial cables, copper wire and fiber optics, including the wires that comprise bus 502. Transmission media can also take the form of acoustic or light waves, such as those generated during radio wave and infrared data communications.

Common forms of computer-readable media include, for example, a floppy disk, a flexible disk, hard disk, magnetic tape, or any other magnetic medium, a CD-ROM, any other optical medium, a RAM, a PROM, and EPROM, a FLASH-EPROM, any other memory chip or cartridge, a carrier wave as described hereinafter, or any other medium from which a computer can read.

Various forms of computer readable media may be involved in carrying one or more sequences of one or more instructions to processor 504 for execution. For example, the instructions may initially be carried on a magnetic disk of a remote computer. The remote computer can load the instructions into its dynamic memory and send the instructions over a telephone line using a modem. A modem local to computer system 500 can receive the data on the telephone line and use an infrared transmitter to convert the data to an infrared signal. An infrared detector can receive the data carried in the infrared signal and appropriate circuitry can place the data on bus 502. Bus 502 carries the data to main memory 506, from which processor 504 retrieves and executes the instructions. The instructions received by main memory 506 may optionally be stored on storage device 510 either before or after execution by processor 504.

The handheld device 560 preferably uses wireless technology that could include infrared (IR), Bluetooth, or RFID technology for communicating with the wireless transceiver in the wireless module of the nebulizer or a separate wireless interface as illustrated. It can be connected directly also. The handheld processing device 560 includes a wireless module 580 that works in conjunction with the pressure transducer interface and controller 518 and the respiratory air flow sensor (flow meter) interface 581 and sends and receives readings through the antenna 582 or other system that could be used. The wireless module 580 could be located at different locations.

For purpose of technical instruction, there now follows a general description of physiology for the involuntary reflex cough test (iRCT), which activates the Nucleus Ambiguus, which is also disclosed in some of the incorporated by reference patent applications. The nebulizer with the flow sensing function is adapted for measuring both voluntary cough and involuntary reflex cough, such as explained in the incorporated by reference patent applications. The iRCT selectively activates the Medial Motor Cell Column (MMCC) of the spinal cord rather than the (Lateral) LMCC to fire muscles embryologically predetermined to be involuntary cough activated muscles in the pelvis. In the past, urologists did not selectively activate MMCC without overtly activating the LMCC. Magnetic stimulation or electrical spinal cord stimulation activate both cell columns and thus it is not possible to sort out pathology with these. Magnetic stimulation or other approaches from CNS activation set off both columns.

The pelvic muscles that typically are activated with MMCC cough activation include the lumbar-sacral L5/S1 paraspinal axial musculature, which facilitates inpatient continence screening. An example is through MMCC iRCT muscle activation, obtaining L5/S1 paraspinal firing but not L5/S1 lateral gastrocnemius activation because the gastroc muscles are limb muscles activated primarily through the LMCC.

The L-S paraspinals are easier to access with a large pad placed above the sacrum on the midline that contains active, reference and ground combined. It is not important to determine lateralization of the activity like needle EMG for radiculopathy, but only if activation occurs reflexively where the onset latency is under the pressure activation of the abdomen such as the Levator Ani. This is a poor muscle for these purposes because people train it to activate and set their pelvis if the person senses any intra-abdominal pressure elevation. Also, it is difficult to get pads to stick to that area with hair, perspiration, fungal infections or bowel/bladder incontinence present, and other factors.

Some examples have been developed and studied, including a normal CNS patient with Lumax bladder and bowel catheters and pads at L5/S1 paraspinals and a separate EMG machine and electrodes at the pelvic floor in a standard 3:00 and 9:00 o'clock set-up to demonstrate simultaneous involuntary activation with iRCT. This sets off the pelvic floor muscles. Thus, normal airway protection data is obtained and normal CNS data to L1 (where spinal cord ends). The set-up includes a complete T12 that cannot void and needs intermittent catheterization with the same set up, thus demonstrating data for normal airway but no L5/S1 EMG activation by MMCC with all the other data necessary to prove an unsafe bladder by the algorithm. A quadriplegic can demonstrate abnormal airway protection and abnormal EMG activation at both paraspinal and pelvic floor muscles with unsafe bladder measurements that follow the algorithm.

It should be understood that iRCT is an involuntary maneuver that activates embryologically predetermined muscles for airway protection and continence that travel primarily through the MMCC in the spinal cord. Different varieties of lesions are captured and determined with summated interval data approach for general screening purposes.

It is known that the laryngeal cough reflex (LCR) is a strong brainstem-mediated reflex that protects the upper airway by preventing aspiration, or the entrance of secretions, food, and/or fluid into the airway below the level of the true vocal cords (rima glottidis), through elicitation of an involuntary cough. The LCR is activated through the stimulation of cough receptors in the vestibule of the larynx. One way this is achieved is through the inhalation of chemo-stimulants, such as tartaric acid. Studies have shown that if the LCR is intact, the subject will involuntarily cough (normal LCR) upon inhaling a solution containing TA.

In one non-limiting example, the iRCT involves the inhalation of a nebulized 20% normal saline solution of L-TA (Tartaric Acid). Subjects are asked to perform 1 to 3 effective, full inhalations (about 15-20 second exposure by mouth for tidal breathing wearing a nose clip) from a standard jet nebulizer with at least 50 psi from an oxygen wall unit or tank that produces an average droplet diameter of 1 to 2 microns or less. The nebulizer output is 0.58 mL/min. The initiation of an involuntary cough reflex after any one of the inhalations is the end point of the procedure.

Nebulized TA is a chemical tussive that stimulates irritant receptors in the mucosa of the laryngeal aditus. Mild irritation of these receptors results in nerve impulses being conveyed by the internal branch of the superior laryngeal nerve (ibSLN) to bulbar centers of the brainstem. This nerve constitutes the afferent sensory component of the LCR arc. The efferent component of the LCR is mediated through the vagus, phrenic, intercostals and thoracoabdominal nerves.

Inhaled TA is selective in stimulating rapidly adapting ("irritant") receptors (RARs), in the supraglottic region. In humans, bilateral anesthesia of the ibSLN abolishes TA-induced cough and permits tidal breathing of the nebulized vapor without coughing, supporting the idea that the RARs are responsible for TA-induced cough.

The physiological response from inhalation of TA in a normal subject is abrupt, forceful coughing of short duration. Using a 20% solution of inhaled nebulized TA is a safe, reliable way to assess the sensation in the supraglottic laryngeal region and subsequently the neurologic circuitry of the LCR. In addition, the ability of the iRCT to predict the integrity of the protective LCR in subjects with stroke has been studied.

A 20% solution of TA as an aerosol causes cough by stimulating sensory nerves in and under the laryngeal epithelium. These nerves have been identified histologically, and the reflexes they cause have been identified. The sensory nerves can be stimulated by both non-isosmolar and acid solutions. Tartaric acid may act in both ways, but the balance between them is uncertain.

The nerves are stimulated by the opening of membrane channels in the nerve terminals. More than 20 categories of channels have now been identified, the opening of which will allow calcium flow into the nerve (and also sodium, with exit of potassium), with the result that an action potential is set up, which travels to the brainstem in the central nervous system (CNS), and reflexively induces cough.

Several different types of sensory nerve ending in the larynx have been identified that may mediate cough and other defensive reflexes. They have been extensively studied, mainly in experimental animals by recording the action potentials in their nerve fibers. The probable candidates for cough are the RARs or 'irritant' receptors. These are highly sensitive to mechanical stimuli, to hyperosmolar solutions, and to acids.

Once stimulated, the sensory nerves will induce a variety of defensive reflexes, which protect the lungs from invasion of harmful material. These include cough (an inspiration, followed by a forced expiration against a closed glottis, followed by opening of the glottis with an expiratory blast); the laryngeal cough expiratory reflex (LCER, a powerful expiratory effort with the glottis open); and the glottal closure reflex. In some instances a reflex apnea can be produced. The balance of these reflexes may depend on the nature and the strength of the stimulus. In the case of TA, the LCER seems to be dominant, possibly followed by glottal closure, and the pathophysiological advantage of this response in preventing aspiration is obvious.

There now follows an analysis and test results in greater detail that explain the advantageous use of the involuntary reflex cough test (iRCT) for investigating and diagnosing not only SUI, but also physiological abnormalities such as neurologic deficiencies. The nebulizer as described can be used in conjunction with testing. It should be understood that there are differences between normal and neurological patients.

The EMG from the parineal muscles respond almost simultaneously to the onset of the voluntary cough because the patient does not want to leak. With the involuntary reflex cough test, on the other hand, the fast fibers that are set off reach the abdominal muscles quickly, such as in 17 milliseconds as an example. The patient is not able to set their pelvis. In some of the graphs reflecting urodynamic testing as will be described, it is evident that the onset of the EMG activity does not happen at the same time the pressure rises. Some people that have neuropathy, for example, spinal stenosis or nerve injury (even if it is mild), have a situation that prevents the reflexes from closing before the pressure has changed to push on the bladder. It is not possible to obtain this diagnostic tool methodology unless the involuntary cough reflex test is accomplished. When the involuntary reflex cough test is accomplished, it is possible to demonstrate a latency delay and show that the pathophysiology is a neuropathic problem rather than a structural problem. It is possible to separate the pathophysiology using the involuntary reflex cough test and methodology as described.

In one example, a female patient could have a weak spinal cord and her physiology is normal. This patient may not leak during the test, but the patient cannot protect her airway. Thus, using the methodology apparatus and system associated with the involuntary reflex cough test, in accordance with non-limiting examples, it is possible not only to diagnose an unprotected airway, but also to diagnose normal bladder physiology, including the neurophysiology to the patient's sphincter closure process. This is advantageous because it is then possible to determine when someone cannot protect their airway, even though they may have a normal bladder. Conversely, there are patients with a normal airway, but cannot control their bladder. This process and system as described is able to make that diagnosis and thus the involuntary reflex cough test is an advantageous medical diagnostic tool. For example, it is possible to have a patient with a poorly functioning bladder and normal airway and use of the test allows a doctor to find lower urinary tract symptoms and neuropathology. It becomes possible to diagnose a level of lesion in a patient with a full comprehensive neurologic examination using the involuntary reflex cough test, methodology and apparatus as described.

As will be described in detail later, the various components such as the nebulizer, one or more catheters, any pads for the paraspinal muscles when EMG is used, and drug as part of the nebulizer are inserted in a kit for use at the clinic, hospital or setting. Those components can be discarded after use. The handheld device, of course, will be used again. Use of the kit provides a clinician, doctor or other medical professional the readily available diagnostic tool to determine if a patient has a questionable airway and determine bladder physiology at the same time, all with the use of the one kit.

A kit that is marketed for the iRCT diagnostic tool could include the nebulizer and its drug as TA in one example and one or more pads for the electrodes at the paraspinal and use with EMG. The pad may only be necessary for stress incontinence determinations. A catheter is included in another kit example for use in measuring airway and intra-abdominal pressure. In one non-limiting example, a pad can be placed on a catheter to determine urine leakage and aid in determining stress incontinence. Pressure data is sent to the handheld device in some examples. Obtaining any EMG values from the paraspinal in conjunction with the urology analysis is advantageous. It is possible in one example to measure pressure from a bladder catheter and determine at the same time EMG signals using the EMG electrodes at the L5/S1 in conjunction with the measured involuntary reflex cough test and urology catheter sensing. This is advantageous compared to placing electrodes at the perineal muscles on each side of the sphincter.

It has been found that EMG signals obtained from the perineal muscles have EMG activity from the non-involuntary muscles, i.e., the voluntary muscles blacking out and making analysis difficult because of the signal interference. When the electrodes are placed at the back at the L5/S1 junction, on the other hand, there is nothing else but the paraspinal muscles. It is bone below on each side at the L5/S1 junction. The electrical impulses can be obtained that determine the number of cough impulses coming down through the patient. This is accomplished even if a person has much adipose. The electrode pad used at the L5/S1 junction, in one non-limiting example, typically has an active reference and ground. A pad holds this active reference and ground and the leads as the active reference and ground are plugged into the handheld device (or wireless sensing device in another example) and transmit data to the processor. At least one catheter is also plugged into the handheld device (or wireless sensing device) and measures bladder pressures. A rectal catheter can also be used in some examples. The processor receives EMG signals and determines when the cough event is over.

The involuntary coughs are not hidden by interference when measured from the lower back at the paraspinals as described. This allows a clinician to determine coughs from the bladder when the EMG located at the L5/S1. In one aspect, the area under curve and the average pressure is determined for the cough event corresponding to the involuntary reflex cough test. When this involuntary component of the cough ends, in one example, it becomes silent EMG activity for a period of time. The pressures are at baseline for a period of time, which corresponds in one example to an inhalation. The involuntary component is over.

Sometimes with the involuntary reflex cough test, the cough occurs six times without breathing, but when the patient stops to breathe, the event is over. Using the programming applied with the processor in the handheld device, it is possible to calculate the variables inside the wave as to the involuntary cough and determine airway protection capability. Thus, it is possible to determine and measure cough by defining through appropriate data processing the involuntary cough event compared to the whole cough epoch. For example, a patient could cough ten times, but only the first four are part of the involuntary cough event. The coughs after that event are not part of the epoch.

The programming includes algorithm branches resulting in a conclusion of unsafe bladder based on the data analysis. It is possible to calculate from the waveforms information necessary for assessing airway protection ability. It should be understood that taking the EMG from the L5/S1 is also a better situation for the doctor or clinician, and the patient, since it is more acceptable in a hospital, outpatient or inpatient setting. The doctor or clinician does not have to bend down or stoop and look near the crotch area and place pads since the EMG can now be taken from the paraspinals. Also, the placement of pads and electrodes at the paraspinals is advantageous when patients are standing. If pads are placed at the perineal area, sweat and other problems could cause those pads to become loose and good signals may not be obtained. Also, it should be understood that the perineal muscles do not fire involuntarily. The sphincter may fire involuntarily, but that would create more noise as noted before. Electrodes are not placed at the vagina, but are placed at the paraspinal area instead.

This information obtained from iRct and the EMG taken at the paraspinals allows the doctor or clinician to obtain data leading directly to a diagnosis. For example, some patients that have urinary stress incontinence may have a normal airway in this analysis. It has been found by experimentation that the normal airway is about 50 centimeters water average intra-abdominal pressure. It should be understood that the vesicular pressure (bladder pressure) can track intra-abdominal pressure and terms are often similar and used together. "Bladder" or intravesicular pressure is often used to determine and equate with intra-abdominal pressure. The two are sometimes used interchangeably. Stress urinary incontinence and/or bladder physiology can be diagnosed. The system and method as described leads directly to diagnosis. Fifty centimeters average intra-abdominal pressure over time has been found to correspond to an involuntary reflex cough test normal airway. Thus, the standard deviations or other percentages from that value are used in one non-limiting example to determine an abnormal airway. In a conducted study, the actual value is determined to be about 50.6 centimeters water as compared to voluntary cough values of about 48 centimeters of water. In an outpatient setting, it is possible to have the nebulizer (and drug) and only a pad and test SUI. In hospitalized patients or inpatient settings, this combination is used to measure airway and bladder physiology and the test combination includes a catheter.

It should be understood that the involuntary cough reflex test (iRCT) gives a higher pressure average than obtained using a voluntary cough test. The involuntary cough reflex test is thus a valuable medical diagnostic tool. In one example, four variables are significant in this analysis. These variables include: (1) duration of the event; (2) average intra-abdominal pressure of the event; (3) peak intra-abdominal pressure (max) of the event; and (4) area under the curve. Using these four variables, it is possible to process the received data and obtain a specific diagnosis that could not otherwise be obtained without the use of the involuntary reflex cough test. Individual deficits in a specific variable or combination of variables are used to characterize specific diseases and problems and useful as a medical diagnostic tool.

Many modifications and other embodiments of the invention will come to the mind of one skilled in the art having the benefit of the teachings presented in the foregoing descriptions and the associated drawings. Therefore, it is understood that the invention is not to be limited to the specific embodiments disclosed, and that modifications and embodiments are intended to be included within the scope of the appended claims.

That which is claimed is:

1. A nebulizer, comprising:
   a body comprising an air channel section and a nebulizer outlet configured to be received within an oral cavity of a patient, said body formed from upper and lower portions, and a medication reservoir formed in the lower portion;
   a reservoir cover supported by the lower portion of the body and covering the medication reservoir to form an enclosed medication reservoir in which medication is contained and held;
   a nozzle assembly supported by the reservoir cover and comprising an air line having an inlet at one end and extending through the air channel section and having an outlet and a venturi nozzle at the outlet and having a venturi outlet, wherein the air line, venturi nozzle and discharge outlet are horizontally oriented when in use and the venturi nozzle is configured to be located within a patient's oral cavity when the nebulizer is in use;

a suction line extending from the medication reservoir to the venturi outlet through which medication is drawn upward when the nebulizer is oriented for use and mixed with air passing through the venturi nozzle and nebulized for discharge through the nebulizer outlet, wherein the venturi nozzle and suction line are formed together and replaceable as one unit and the venturi nozzle outputs air in a direction that is normal to the suction line;

wherein the reservoir cover includes a diffuser that extends upward during normal usage of the nebulizer and located proximal of the venturi nozzle to which nebulized medication and air from the venturi nozzle impact to aid nebulization; and wherein the diffuser includes a horizontal lock member and the outlet of the air line includes a top clip member adjacent the venturi nozzle and forms a locking slot that receives the horizontal lock member of the diffuser to snap lock the nozzle assembly and reservoir cover together.

2. The nebulizer according to claim 1, wherein the diffuser includes a vertical slot opening through which nebulized medication and gas pass.

3. The nebulizer according to claim 1, wherein said lower body portion and reservoir cover include snap fit members configured to snap fit the reservoir cover to the lower body portion.

4. The nebulizer according to claim 1, wherein the air line provides continuous pressure between the input end and outlet end of the air line and no medication is drawn upward through the suction line for nebulization and discharge through the nebulizer outlet until a predetermined negative inspiratory pressure is created from inhalation by a user to begin air flow through the venturi nozzle and medication is drawn upward through the suction line and nebulized by air flowing through the venturi nozzle to be discharged through the nebulizer outlet.

5. The nebulizer according to claim 4, wherein nebulization begins at a negative inspiratory pressure of from about $-3$ $cmH_2O$ to about $-52$ $cmH_2O$.

6. The nebulizer according to claim 1, wherein the medication reservoir is configured to be located within a patient's oral cavity when the nebulizer is in use.

7. The nebulizer according to claim 1, wherein the upper and lower portions of the body, the reservoir cover and the nozzle assembly are formed from a plastic material.

8. A nebulizer, comprising:

a body comprising an air channel section and a nebulizer outlet configured to be received within an oral cavity of a patient, said body formed from upper and lower portions, and a medication reservoir formed in the lower portion;

a reservoir cover supported by the lower portion of the body and covering the medication reservoir to form an enclosed medication reservoir in which medication is contained and held;

a nozzle assembly supported by the reservoir cover and comprising an air line having an inlet at one end and extending through the air channel section and having an outlet and a venturi nozzle at the outlet and having a venturi outlet, wherein the air line, venturi nozzle and discharge outlet are horizontally oriented when in use and the venturi nozzle is configured to be located within a patient's oral cavity when the nebulizer is in use;

a suction line extending from the medication reservoir to the venturi outlet through which medication is drawn upward when the nebulizer is oriented for use and mixed with air passing through the venturi nozzle and nebulized for discharge through the nebulizer outlet, wherein the venturi nozzle and suction line are formed together and replaceable as one unit and the venturi nozzle outputs air in a direction that is normal to the suction line;

an air flow sensor positioned within the air channel section and configured to generate signals indicative of air flow generated by a patient's involuntary cough event occurring at nebulization;

a processor configured to receive signals from the air flow sensor and to evaluate the involuntary cough event;

wherein the reservoir cover includes a diffuser that extends upward during normal use of the nebulizer and located proximal of the venturi nozzle to which nebulized medication and air from the venturi nozzle impact to aid nebulization; and wherein the diffuser includes a horizontal lock member and the outlet of the air line includes a top clip member adjacent the venturi nozzle and forms a locking slot that receives the horizontal lock member of the diffuser to snap lock the nozzle assembly and reservoir cover together.

9. The nebulizer according to claim 8, wherein the diffuser includes a vertical slot opening through which nebulized medication and gas pass.

10. The nebulizer according to claim 8, wherein said lower body portion and reservoir cover include snap fit members configured to snap fit the reservoir cover to the lower body portion.

11. The nebulizer according to claim 8, wherein the air line is configured to provide continuous pressure between the input end and outlet end of the air line and no medication is drawn upward through the suction line for nebulization and discharge through the nebulizer outlet until a predetermined negative inspiratory pressure is created from inhalation by a patient to begin air flow through the venturi nozzle and medication is drawn upward through the suction line and nebulized by air flowing through the venturi nozzle to be discharged through the nebulizer outlet.

12. The nebulizer according to claim 11, wherein nebulization begins at a negative inspiratory pressure of from about $-3$ $cmH_2O$ to about $-52$ $cmH_2O$.

13. The nebulizer according to claim 11, wherein the medication reservoir is configured to be located within a patient's oral cavity when the nebulizer is in use.

14. The nebulizer according to claim 8, wherein the upper and lower portions of the body, the reservoir cover and the nozzle assembly are formed from a plastic material.

* * * * *